(12) United States Patent
Woodcock et al.

(10) Patent No.: US 10,583,115 B2
(45) Date of Patent: Mar. 10, 2020

(54) MODULATORS OF 14-3-3 FUNCTIONALITY AND USES THEREOF

(71) Applicants: University of South Australia, Adelaide (AU); Central Adelaide Local Health Network Inc., Adelaide (AU)

(72) Inventors: Joanna Woodcock, Crafers (AU); Angel Lopez, Medindie (AU); Stuart Maxwell Pitson, Glenside (AU); Michael Susithiran Samuel, North Adelaide (AU); Carl Coolen, Salisbury South (AU)

(73) Assignees: University of South Australia, Adelaide (AU); Central Adelaide Local Health Network Inc., Adelaide (AU)

( * ) Notice: Subject to any disclaimer, the term of this patent is extended or adjusted under 35 U.S.C. 154(b) by 0 days.

(21) Appl. No.: 15/517,755

(22) PCT Filed: Oct. 8, 2015

(86) PCT No.: PCT/AU2015/000605
§ 371 (c)(1),
(2) Date: Apr. 7, 2017

(87) PCT Pub. No.: WO2016/054680
PCT Pub. Date: Apr. 14, 2016

(65) Prior Publication Data
US 2017/0312249 A1     Nov. 2, 2017

(30) Foreign Application Priority Data

Oct. 8, 2014  (AU) ................. 2014904015
Oct. 8, 2014  (AU) ................. 2014904016

(51) Int. Cl.
| | | |
|---|---|---|
| *A61K 31/395* | (2006.01) | |
| *A61K 45/06* | (2006.01) | |
| *A61K 31/40* | (2006.01) | |
| *A61K 31/452* | (2006.01) | |
| *A61K 9/00* | (2006.01) | |
| *A61K 47/10* | (2017.01) | |
| *A61K 9/06* | (2006.01) | |

(52) U.S. Cl.
CPC .......... *A61K 31/395* (2013.01); *A61K 9/0014* (2013.01); *A61K 9/06* (2013.01); *A61K 31/40* (2013.01); *A61K 31/452* (2013.01); *A61K 45/06* (2013.01); *A61K 47/10* (2013.01)

(58) Field of Classification Search
None
See application file for complete search history.

(56) References Cited

FOREIGN PATENT DOCUMENTS

| WO | WO 2005/055925 | 6/2005 |
| WO | WO 2009/067811 | 6/2009 |
| WO | WO 2011/120082 | 10/2011 |
| WO | WO 2014/118556 | 8/2014 |

OTHER PUBLICATIONS

Schultz et al., "14-3-3σ silencing during melanoma progression and its role in cell cycle control and cellular senescence", Molecular Cancer, 2009, 8:53 (13 pages).*
Shiba-Ishii et al., "High expression of stratifin is a universal abnormality during the course of malignant progression of early-stage lung adenocarcinoma", International Journal of Cancer, 2011, vol. 129, pp. 2445-2453.*
Goodman Gilman et al., Goodman and Gilman's The Pharmacological Basis of Therapeutics, Seventh Edition, 1985, p. 36.*
Phan et al., "The cell cycle regulator 14-3-3σ opposes and reverses cancer metabolic reprogramming", Nat. Commun. 6:7530 doi: 10.1038/ncomms8530 (2015).*
Pan et al., "The Potential Role of miR-451 in Cancer Diagnosis, Prognosis, and Therapy," *Mol. Cancer Ther.*, vol. 12:1153-1162, 2013.
Roberts et al., "Stratifin (14-3-3 σ) Limits Plakophilin-3 Exchange with the Desmosomal Plaque," *PLoS ONE*, vol. 8:e77012, 2013.
Woodock et al., "Destabilisation of dimeric 14-3-3 Proteins as a Novel Approach to Anti-Cancer Therapeutics," *Oncotarget*, vol. 6:14522-14536, 2015.
Zhao et al., "14-3-3 Proteins as Potential Therapeutic Targets," *Seminars in Cell & Develop. Bio.*, vol. 22:705-712, 2011.
Freeman and Morrison, "14-3-3 Proteins: Diverse Functions in Cell Proliferation and Cancer Progression," *Seminars in Cell & Developmental Biology* 22(7): 681-687, 2011.
Ganguli-Indra, G., "Protocol for Cutaneous Wound Healing Assay in a Murine Model" p. 151-159, Chapter 12 of Stem Cells and Tissue Repair, Methods in Molecular Biology series, vol. 1210, Ed. J.M. Walker, Springer Science+Business Media, New York, 2014.
Jung, "Human Tumor Xenograft Models for Preclinical Assessment of Anticancer Drug Development," *Toxicological Research* 30: 1-5, 2014.

* cited by examiner

*Primary Examiner* — Savitha M Rao
*Assistant Examiner* — Gregg Polansky
(74) *Attorney, Agent, or Firm* — Klarquist Sparkman, LLP

(57) ABSTRACT

The present disclosure relates to modulators of 14-3-3 functionality and their use in methods and compositions for preventing and/or treating various diseases, conditions and states, such as cancer and healing of wounds. Certain embodiments of the present disclosure provide a method of preventing and/or treating a disease, condition or state in a subject associated with altered 14-3-3 protein functionality and/or which would benefit from altering 14-3-3 functionality, the method comprising administering to the subject an effective amount of an agent which inhibits dimerization of the 14-3-3 protein, thereby preventing and/or treating the disease, condition or state in the subject.

7 Claims, 16 Drawing Sheets

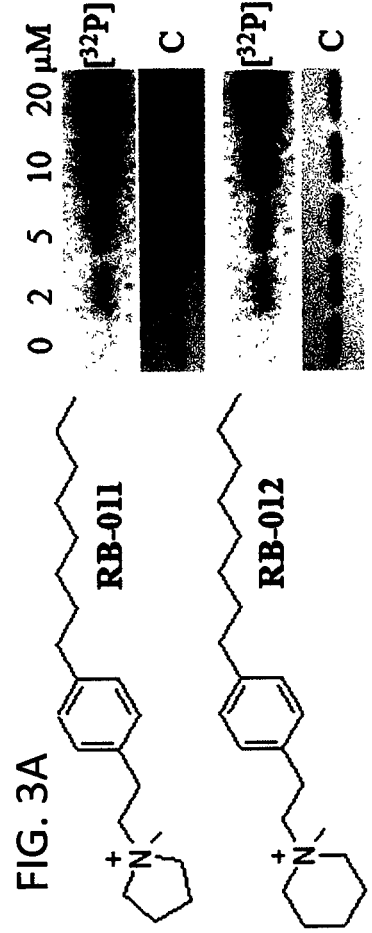
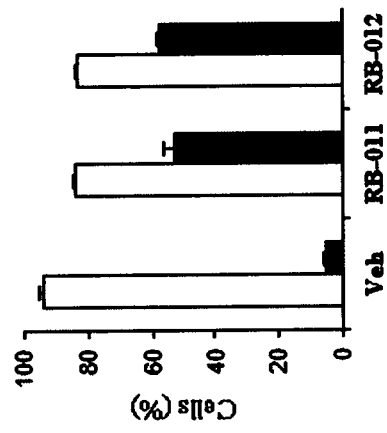
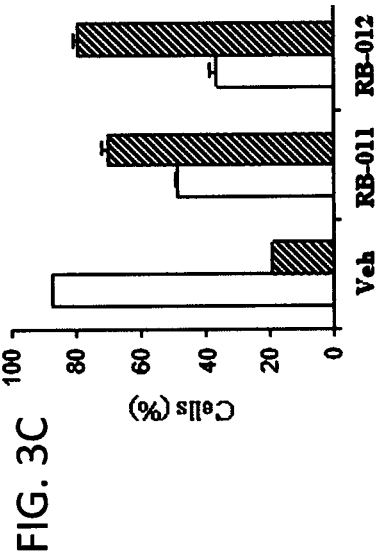
FIG. 3A
FIG. 3B
FIG. 3C

FIG. 4A
FIG. 4B
FIG. 4C
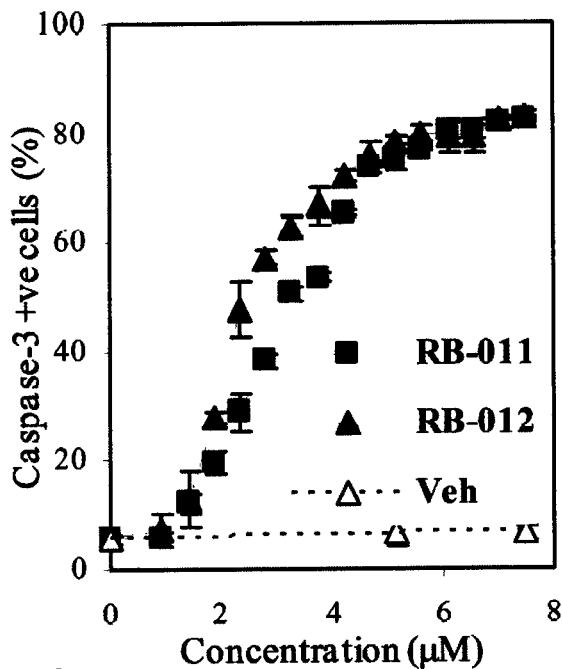
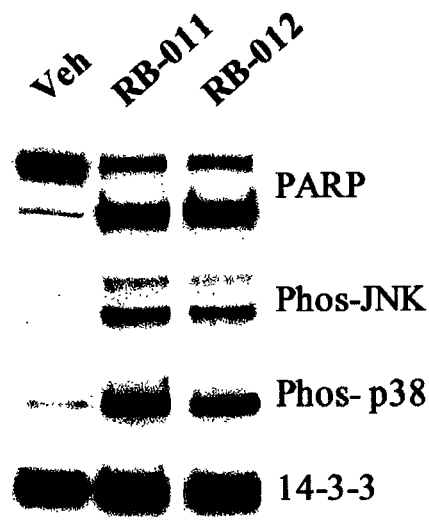
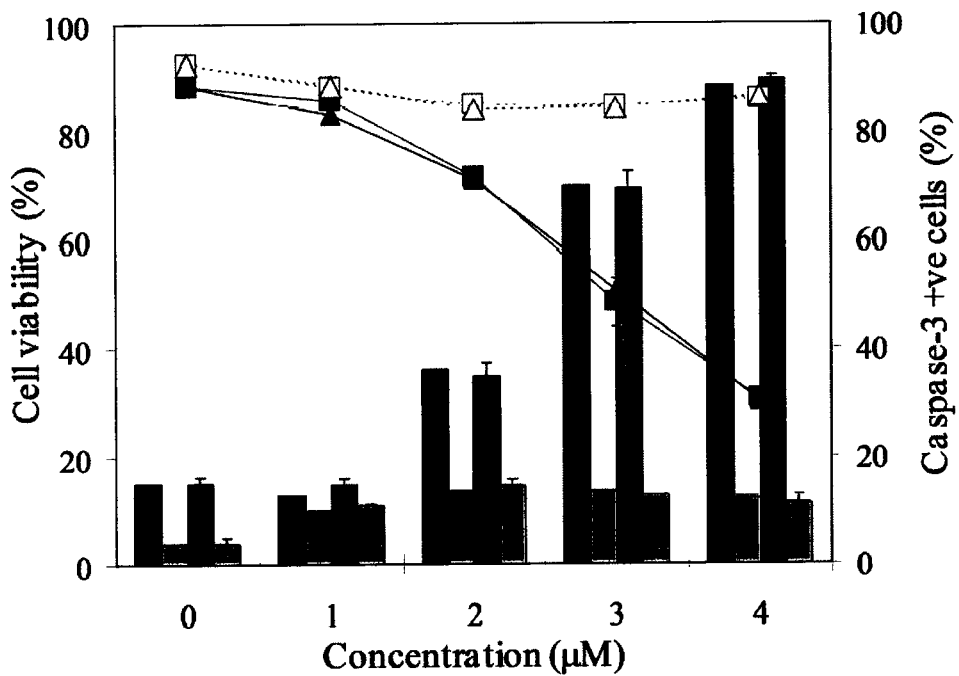

FIG. 14A
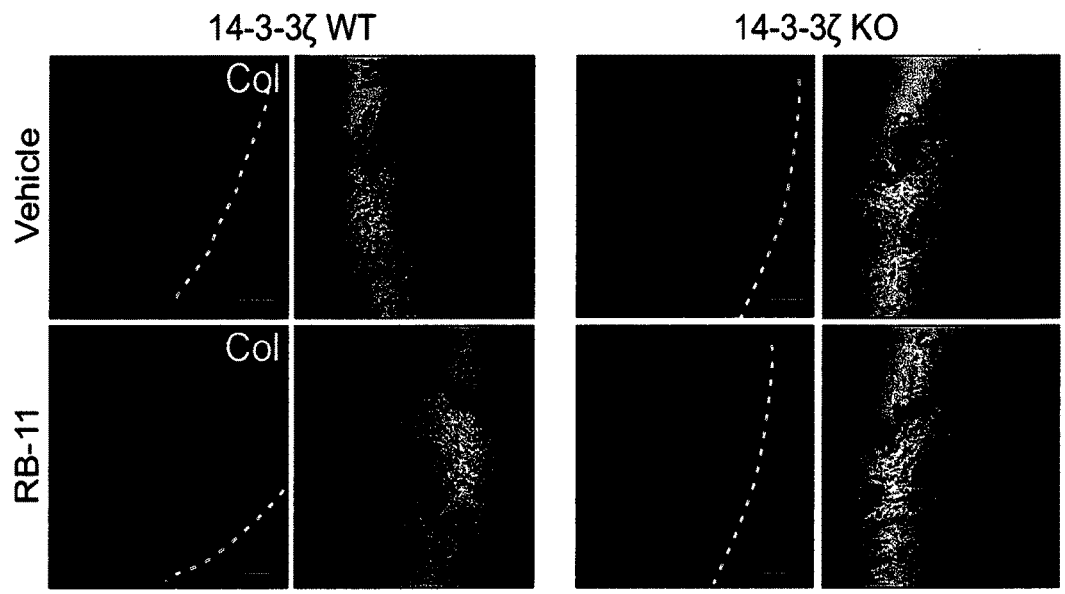
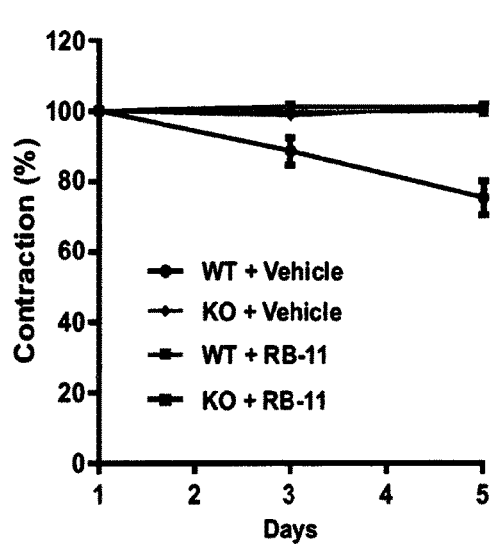
FIG. 14B
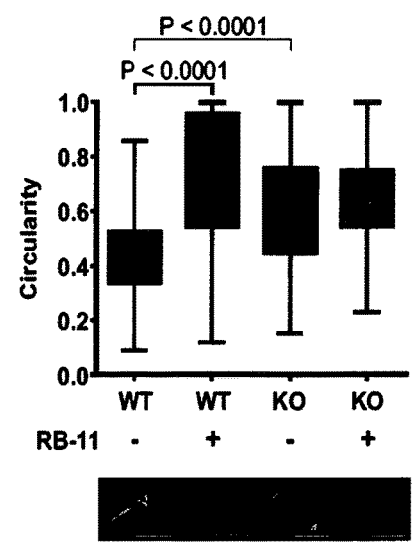
FIG. 14C

MODULATORS OF 14-3-3 FUNCTIONALITY AND USES THEREOF

PRIORITY CLAIM

This application is the U.S. National Stage of International Application No. PCT/AU2015/000605 filed Oct. 8, 2015, published in English under PCT Article 21(2), which claims priority to Australian provisional patent application number 2014904015 filed on 8 Oct. 2014 and Australian provisional patent application number 2014904016 filed on 8 Oct. 2014, the contents of which applications are hereby incorporated by reference.

FIELD

The present disclosure relates to modulators of 14-3-3 functionality and their use in methods and compositions for preventing and/or treating various diseases, conditions and states, such as cancer and healing of wounds.

BACKGROUND

The 14-3-3 proteins are a conserved family of dimeric phospho-serine binding proteins that interact and modulate the functions of multiple cellular proteins and in so doing regulate many signalling pathways. The 14-3-3 proteins are composed of two 30 kDa monomer units that are each capable of binding a phospho-serine motif via an amphipathic groove. Dimers of 14-3-3 are formed by helix 1 of one monomer interacting with helices 3 and 4 of another monomer. Functionally, 14-3-3 proteins perform multiple roles in regulating cellular protein activities and these functions of 14-3-3 are dependent on its dimeric structure.

14-3-3 proteins are an attractive target for therapeutic purposes. For example, enhanced expression of 14-3-3 proteins has been detected in a variety of disorders, including many human cancers and which correlate with more aggressive tumours and poor prognosis. Because of the biological roles of 14-3-3 proteins, there has been considerable interest in identifying agents that have the ability to modulate 14-3-3 activity, such as small molecules that function as mimics of 14-3-3 phospho-clients. However, while such small molecules have shown activity in vitro, to date they appear to have had limited therapeutic potential.

For a variety of disorders there is a continuing need to identify new possible targets for therapeutic intervention and to identify molecules that have therapeutic potential. The present disclosure relates to use of 14-3-3 proteins as a therapeutic target.

SUMMARY

Certain embodiments of the present disclosure provide a method of preventing and/or treating a disease, condition or state associated with altered 14-3-3 protein functionality and/or a method of preventing and/or treating a disease, condition or state which would benefit from altering 14-3-3 protein functionality, the method comprising administering to the subject an agent that modulates 14-3-3 protein functionality.

Certain embodiments of the present disclosure provide a method of preventing and/or treating a disease, condition or state in a subject associated with altered 14-3-3 protein functionality and/or which would benefit from altering 14-3-3 functionality, the method comprising administering to the subject an effective amount of an agent which inhibits dimerization of the 14-3-3 protein, thereby preventing and/or treating the disease, condition or state in the subject.

Certain embodiments of the present disclosure provide use of an agent in the preparation of a medicament for preventing and/or treating a disease, condition or state in a subject associated with altered 14-3-3 protein functionality, wherein the agent inhibits dimerization of the 14-3-3 protein.

Certain embodiments of the present disclosure provide a method of increasing the sensitivity of a cancer in a subject to treatment with a chemotherapeutic agent, the method comprising administering to the subject an effective amount of an agent which inhibits dimerization of the 14-3-3 protein, thereby preventing and/or treating the disease, condition or state in the subject.

Certain embodiments of the present disclosure provide a method of promoting apoptosis of a cell, the method comprising exposing the cell to an effective amount of an agent that inhibits dimerization of a 14-3-3 protein, thereby promoting apoptosis of the cell.

Certain embodiments of the present disclosure provide a method of inhibiting proliferation of a cell, the method comprising exposing the cell to an effective amount of an agent that inhibits dimerization of a 14-3-3 protein, thereby inhibiting proliferation of the cell.

Certain embodiments of the present disclosure provide an anti-cancer composition comprising a therapeutically effective amount of an agent comprising a cationic lipid comprising a heterocyclic head group and a hydrophobic tail group of at least 12 carbon atoms.

Certain embodiments of the present disclosure provide a combination product, the product comprising the following components:
  an agent that inhibits dimerization of a 14-3-3 protein; and
  an anti-cancer agent,
    wherein the components are provided in a form for separate or co-administration to a subject in need thereof.

Certain embodiments of the present disclosure provide a method of identifying an inhibitor of dimerization of a 14-3-3 protein, the method comprising:
  exposing a 14-3-3 protein to a candidate agent comprising a cationic lipid comprising a heterocyclic head group and a hydrophobic tail group of at least 12 carbon atoms;
  determining the ability of the candidate agent to inhibit dimerization of the 14-3-3 protein; and
  identifying the candidate agent as an inhibitor of dimerization of a 14-3-3 protein.

Certain embodiments of the present disclosure provide a method of modulating healing of a wound in a subject, the method comprising administering to the subject an effective amount of an agent which modulates 14-3-3 protein functionality, thereby modulating healing of the wound in the subject.

Certain embodiments of the present disclosure provide a method of promoting healing of a wound in a subject, the method comprising administering to the subject an effective amount of an agent that inhibits dimerization of a 14-3-3 protein, thereby promoting healing of the wound in the subject.

Certain embodiments of the present disclosure provide use of an agent in the preparation of a medicament for promoting healing of a wound in a subject, wherein the agent inhibits dimerization of a 14-3-3 protein.

Certain embodiments of the present disclosure provide a method of treating a subject suffering from a wound, the method comprising administering to the subject an effective amount of an agent that inhibits dimerization of a 14-3-3 protein, thereby treating the wound in the subject.

Certain embodiments of the present disclosure provide a wound healing composition, the composition comprising an agent that inhibits dimerization of a 14-3-3 protein.

Certain embodiments of the present disclosure provide a topical composition, the composition comprising an agent that inhibits dimerization of a 14-3-3 protein and a topically acceptable excipient.

Certain embodiments of the present disclosure provide a wound healing product, the product comprising a releasable agent that inhibits dimerization of a 14-3-3 protein.

Certain embodiments of the present disclosure provide a bandage or dressing comprising a releasable agent that inhibits dimerization of a 14-3-3 protein.

Certain embodiments of the present disclosure provide a method of identifying a wound healing agent, the method comprising:

determining the ability of a candidate agent to inhibit 14-3-3 dimerization; and identifying the candidate agent as a wound healing agent.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 1A. Panel of N-alkylated trimethyl-ammonium (TMA) compounds assessed for 14-3-3 modulating activity. FIG. 1B. Phosphorylation of 14-3-3 by PKA in vitro in presence or absence of TMA compounds at concentrations shown. Upper panel is [$^{32}$P]-phospho-labelled 14-3-3ζ and lower panel Coomassie stained 14-3-3 protein. FIG. 1C. Effect of TMA compounds on Jurkat cells after 20 hours treatment at the concentrations shown. Cell viability is shown in open bars and TMRE negative staining cells are shown in black bars. The error bars show the range of duplicate determinations.

FIG. 2A shows effect on in vitro phosphorylation of 14-3-3ζ (Wt and S58A) by PKA in the presence of increasing concentrations of CTAB. FIG. 2B. Quantitation of 14-3-3ζ phosphorylation with increasing CTAB concentration. FIG. 2C. Effect of 5 µM CTAB on cell viability (FS vs SS plots inset) and caspase-3 activation (histograms) in parental Jurkat cells (left panel) and Jurkat cells over-expressing Bcl-2 (right panel) after 20 hours.

FIGS. 3A-3C show the effect of various molecules on 14-3-3 phosphorylation and cell viability. FIG. 3A shows TMA-FTY hybrid RB molecules and their effect on in vitro 14-3-3 phosphorylation by PKA at the concentrations shown. The upper panel is [$^{32}$P]-phospho-labelled 14-3-3ζ ([$^{32}$P]) and the lower panel is Coomassie-stained 14-3-3ζ protein FIG. 3B shows effect of 5 µM RB molecules on viability (open bars) and caspase-3 activation (black bars) of Jurkat cells after 5 hours treatment. FIG. 3C shows effect of 5 µM RB molecules on viability (open bars) and Annexin V staining (hashed bars) of Jurkat cells after 24 hours treatment. The error bars show the range of duplicate determinations.

FIGS. 4A-4C show the effects of RB-011 and RB-012 on caspase activation and viability. FIG. 4A shows dose response of Caspase-3 activation in Jurkat cells after 5 hours treatment with RB-011 (closed squares), RB-012 (closed triangles) or vehicle (veh; open triangles). The error bars show the range of duplicate determinations. FIG. 4B shows Immunoblotting after treatment of Jurkat cells with vehicle or 7.5 µM RB-011 or RB-012. FIG. 4C shows effect of RB-011 (closed squares) and RB-012 (closed triangles) on cell viability (shown by line graph) and caspase-3 activation (histograms) in parental Jurkat cells (solid lines and block histogram) and Jurkat cells over-expressing Bcl-2 (dashed lines and hashed historanm) after 20 hours treatment. The error bars show the range of duplicate determinations.

FIG. 5A shows analysis of RB-012 induced signalling events over time by immunoblotting. FIG. 5B shows analysis of RB-012 induced apoptosis over time by immunoblotting.

FIG. 6A shows growth/survival of NSCLC cell line A549 is inhibited by RB-011 and -012 as determined by MTS assay after 48 hours treatment. Error bars represent standard error of triplicate measurements. FIG. 6B. RB-011 and RB-012 induce caspase activation in A549 cells. The error bars show the range of duplicate determinations. FIG. 6C. Effect of RB-011 and -012 on A549 colony growth in soft agar. Results are expressed relative to colony numbers in untreated controls. FIG. 6D. Growth of A549 xenograft in Balb/C nude mice is retarded by administration of RB-012. RB-012, saline or FTY720 was administered daily to mice bearing A549 tumours by intraperitoneal injection using the dosing regime shown. All experimental data are shown as the mean±SEM.

FIG. 7C shows regression analysis of median wound width reduction over time as the wound heals, in wild-type and 14-3-3ζ-deficient mice. Half times of wound healing indicated on the panel illustrate that 14-3-3ζ-deficient wounds healed more rapidly than wild-type wounds.

FIG. 14A shows dual two-photon SHG and transmission microscopy showing collagen expression (Col) around the wound margins (dotted lines) in 14-3-3ζ WT and KO skin sections treated with RB-11 or vehicle control, merged with a transmission image generated from H&E staining of the same section (Trans). Scale bars—100 µm. FIG. 14B shows the percentage contraction of collagen matrices generated in FIG. 13A as a function of time. Measurements are shown for WT cells, WT cells treated with RB-11 (10 µM), 14-3-3ζ deficient cells and 14-3-3ζ deficient cells treated with RB-11 (10 µM). Matrices were treated with 10 µm RB-11 on days 1 and 5. Error bars indicate S.E.M. N=3 collagen matrices per condition. FIG. 14C is a box and whisker plot showing circularity analysis data calculated as described in the materials and methods section, from 14-3-3ζ WT and KO dermal fibroblasts cultured in media containing RB-11 (10 µM) or vehicle within collagen matrices. Data are represented as medians with all quartiles indicated. P values were calculated by one-way ANOVA and Tukey's post-test. N=3 collagen matrices per condition. Images show single frames from live cell imaging videos of dual 2-photon GFP-fluorescence and collagen SHG analysis of GFP labelled WT and 14-3-3ζ KO dermal fibroblasts. Scale bars—100 µm.

DETAILED DESCRIPTION

Figure 1A:
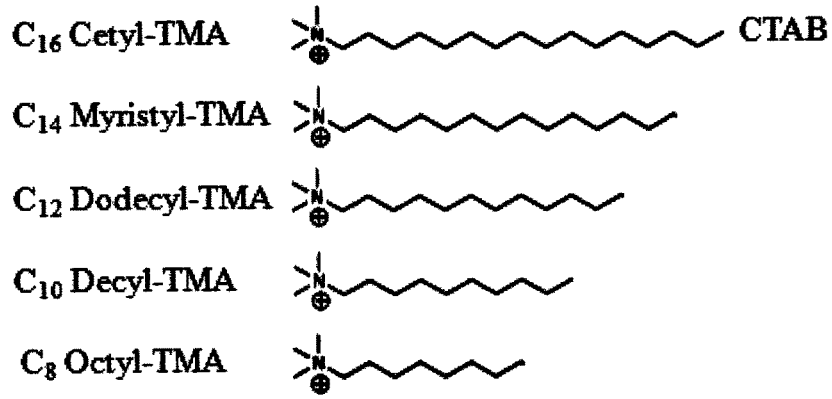
FIGS. 1A-1C show N-alkylated trimethyl-ammonium (TMA) compounds assessed for 14-3-3 modulating activity and effect on Jurkat cells.

The present disclosure relates to the recognition that modulating the activity of 14-3-3 protein may be used to prevent and/or treat certain diseases, condition or states.

The present disclosure is based, at least in part, on the determination that agents that inhibit dimerization of 14-3-3 proteins induce rapid down-regulation of proliferative and survival signalling in cells, resulting in apoptosis. As such, these agents are therapeutic candidates for preventing and/or treating diseases, conditions or states associated with altered 14-3-3 functionality. Further, cationic agents have been rationally designed that inhibit 14-3-3 dimerization and which demonstrate therapeutic potential in an in vivo model of cancer.

In addition, it has also been determined that 14-3-3ζ KO mice exhibit rapid re-epithelialization following wounding and increased collagen production and that decreased re-modeling is observed in 14-3-3 ζ deficient skin during wound healing. These studies demonstrate that modulating healing of a wound may be achieved by modulating 14-3-3 protein functionality. Further, inhibitors of 14-3-3 dimerization show improved wound healing and reduced ability to remodel a collagen plug.

Certain embodiments of the present disclosure are directed to methods and products that have one or more combinations of advantages. For example, some of the advantages of certain embodiments disclosed herein include one or more of the following: providing new methods and products for targeting 14-3-3 functionality; providing new or improved treatment of diseases, conditions or states associated with altered 14-3-3 functionality; providing new products for preventing and/or treating diseases, conditions or states associated with altered 14-3-3 functionality; providing new methods and product for preventing and/or treating using 14-3-3 as a therapeutic target; providing new cancer agents; providing cancer agents with improved efficacy for specific types of cancers; increasing the sensitivity of some cancers to treatment with other agents; providing new products for promoting apoptosis and/or inhibiting proliferation; providing new methods and products for wound healing and/or treating wounds; providing new methods of screening for candidate therapeutic agents; to address one or more problems and/or to provide one or more advantages, or to provide a commercial alternative. Other advantages of certain embodiments of the present disclosure are also disclosed herein.

Certain embodiments of the present disclosure provide a method of preventing and/or treating a disease, condition or state.

Certain embodiments of the present disclosure provide a method of preventing and/or treating a disease, condition or state associated with altered 14-3-3 protein functionality and/or a method of preventing and/or treating a disease, condition or state which would benefit from altering 14-3-3 protein functionality, the method comprising administering to the subject an agent that modulates 14-3-3 protein functionality.

In certain embodiments, the agent inhibits 14-3-3 functionality. In certain embodiments, the agent promotes 14-3-3 functionality.

The term "modulate", and variants thereof such as "modulating", refers to a promotion, inhibition and/or change of a property. In certain embodiments, the modulating comprises a promotion, increase, enhancement, or stimulation of a property. In certain embodiments, the modulating comprises an inhibition, decrease, reduction, retardation, delay or suspension of a property. Examples of a property include protein activity, localization of the mRNA and/or protein, stability of the mRNA and/or protein, expression of the mRNA and/or protein, and binding and/or association of the protein with itself and/or other an entities. Other types of properties are contemplated.

For example, an agent may change activity of a 14-3-3 protein, the agent may change localisation of a 14-3-3 protein, the agent may change the synthesis and/or degradation rates of a 14-3-3 protein, the agent may change the timing of 14-3-3 protein activity or expression, the agent may change the ability of the 14-3-3 protein to interact with itself or other species, the agent may change the chemical composition of a 14-3-3 protein, and the agent may change signalling events associated with a 14-3-3 protein. In a similar manner, the agent may also change upstream or downstream effectors of 14-3-3 functionality.

In certain embodiments, the modulating comprises a promotion, increase, enhancement, or stimulation of 14-3-3 protein functionality.

In certain embodiments, the modulating comprises an inhibition or decrease of 14-3-3 protein functionality.

In certain embodiments, the agent inhibits dimerization of a 14-3-3 protein, thereby inhibiting 14-3-3 protein functionality.

In certain embodiments, the agent is a selective inhibitor. In certain embodiments, the agent is a non-selective inhibitor. Examples of agents are as described herein.

Certain embodiments of the present disclosure provide a method of preventing and/or treating a disease, condition or state associated with altered 14-3-3 protein functionality and/or a method of preventing and/or treating a disease, condition or state which would benefit from altering 14-3-3 protein functionality, by administering to the subject an agent that modulates 14-3-3 protein functionality.

Certain embodiments of the present disclosure provide a method of preventing and/or treating a disease, condition or state in a subject associated with altered 14-3-3 protein functionality and/or which would benefit from altering 14-3-3 protein functionality, the method comprising administering to the subject an effective amount of an agent which inhibits dimerization of a 14-3-3 protein, thereby preventing and/or treating the disease, condition or state in the subject.

The term "preventing", and related terms such as "prevention" and "prevent", refer to obtaining a desired pharmacologic and/or physiological effect in terms of arresting or suppressing the appearance of one or more symptoms in the subject. The term "treatment", and related terms such as "treating" and "treat", refer to obtaining a desired pharmacologic and/or physiological effect in terms of improving the condition of the subject, ameliorating, arresting, suppressing, relieving and/or slowing the progression of one or more symptoms in the subject, a partial or complete stabilization of the subject, a regression of the one or more symptoms, or a cure of a disease, condition or state in the subject.

In certain embodiments, the disease, condition or state is associated with increased or dysregulated 14-3-3 protein expression.

In certain embodiments, the disease, condition or state is a cancer, a solid cancer, a non-solid cancer, a neoplastic disease, an inflammatory disease, condition or state, or a neurodegenerative disease, condition or state.

In certain embodiments, the disease, condition or state is a nervous system tumour, retinoblastoma, neuroblastoma, paediatric tumour, head and neck cancer, squamous cell cancer, a breast cancer, a prostate cancer, lung cancer, a neck cancer, kidney cancer, renal cell adenocarcinoma, brain cancer, lung cancer, stomach cancer, oesophagogastric cancer, hepatocellular carcinoma, pancreaticobiliary neoplasia colorectal cancer, cervical cancer, anal cancer, uterine and other reproductive tract cancer, urinary tract cancer, urinary tract cancer of the ureter and bladder, germ cell tumour, testicular germ cell tumour, ovarian germ cell tumour, ovarian cancer, ovarian epithelial cancer, carcinomas, human immunodeficiency associated malignancies, Kaposi's sarcoma, lymphoma, a blood borne cancer, leukemia, malignant melanoma, sarcoma, endocrine tumour, endocrine tumours of the thyroid gland, mesothelioma and other pleural tumour, neuroendocrine tumour, carcinoid tumours.

In certain embodiments, the cancer comprises a cancer with a poor prognosis. In certain embodiments, the cancer comprises a cancer that is resistant to treatment with an anti-cancer agent, such as a chemotherapeutic agent.

In certain embodiments, the disease, condition or state is associated with a bcr-abl oncogene.

In certain embodiments, the disease, condition or state is a non-solid cancer selected from a chronic myelogenous leukaemia, an acute lymphoblastic leukaemia, or a chronic neutrophilic leukaemia.

In certain embodiments, the chronic myelogenous leukaemia is a late form of chronic myelogenous leukaemia.

In certain embodiments, the non-solid cancer is resistant to imatinib or other protein tyrosine-kinase inhibitor against bcr-abl.

In certain embodiments, the disease, condition or state comprises rheumatoid arthritis, atherosclerosis, asthma, autoimmune disease, inflammatory bowel disease, Parkinson's disease, Alzheimer's disease, Creutzfeldt-Jakob disease and a transmissible spongiform encephalopathy. Other diseases, conditions or states are contemplated.

In certain embodiments, the subject is suffering from a disease, condition or state associated with altered 14-3-3 protein functionality. Disease, conditions and states associated with altered 14-3-3 protein functionality are as described herein.

In certain embodiments, the disease, condition or state is a disease, condition or state which would benefit from altering 14-3-3 protein functionality, such as a wound.

In certain embodiments, the subject is susceptible to a disease, condition or state associated with altered 14-3-3 protein functionality. In certain embodiments, the subject has an increased risk or likelihood of suffering from a disease, condition or state associated with altered 14-3-3 protein functionality.

In certain embodiments, the subject is suffering from, or susceptible to, a disease, condition or state associated with increased or dysregulated 14-3-3 protein functionality.

In certain embodiments, the subject is a subject with a cancer having a poor survival, a subject with a cancer having a poor prognosis, and/or a subject with a cancer that is resistant to chemotherapy.

In certain embodiments, the disease, condition or state comprises a wound. In certain embodiments, the wound is a wound in a subject suffering from, or susceptible to, diabetes.

In certain embodiments, the subject is suffering from, or susceptible to, a disease, condition or state associated with increased or dysregulated 14-3-3 protein functionality.

In certain embodiments, the subject is a human subject.

In certain embodiments, the subject is a mammalian subject, a livestock animal (such as a horse, a cow, a sheep, a goat, a pig), a domestic animal (such as a dog or a cat) and other types of animals such as monkeys, rabbits, mice and laboratory animals. Veterinary applications of the present disclosure are contemplated. Use of any of the aforementioned animals as animal models is also contemplated.

In certain embodiments, the 14-3-3 protein comprises a 14-3-3 protein selected from the group consisting of a 14-3-3ζ protein, a 14-3-3η protein, a 14-3-3γ protein, a 14-3-3ε protein, and a 14-3-3β protein.

In certain embodiments, the 14-3-3 protein comprises a 14-3-3 protein selected from the group consisting of a 14-3-3ζ protein, a 14-3-3η protein and a 14-3-3γ protein.

In certain embodiments, the 14-3-3 protein comprises a 14-3-3ζ protein.

The term "14-3-3 protein" is to be understood to include reference to all forms of protein 14-3-3. Without limiting the present invention to any one theory or mode of action, the 14-3-3 proteins are a conserved family of dimeric phosphoserine binding proteins that interact and modulate the functions of multiple cellular proteins and in so doing regulate many signalling pathways (see for example Tzivion and Avruch 2002, J. Biol. Chem. 277:3061-64; Fu et al. 2000, Ann. Rev. Pharma. Tox. 40:617-47). The term should be understood to also extend to any isoforms which arise from alternative splicing of protein 14-3-3 mRNA or allelic or polymorphic variants. Isoforms of the human protein include the β isoform (NCBI Ref. Sequence Number NM_003404.3), ε isoform (NCBI Ref. Sequence Number NM_006761.4), γ isoform (NCBI Ref. Sequence Number NM_012479.3), η isoform (NCBI Ref. Sequence Number NM_003405.3), σ isoform (NCBI Ref. Sequence Number NM_006142.3), τ isoform (NCBI Ref. Sequence Number NM._006826.2) and ζ isoform (NCBI Ref. Sequence Number NM_003406.3). The equivalent protein in other species may be determined by a known method. Methods for identifying a 14-3-3 gene or protein include, for example, nucleic acid and protein alignment programs, such as BLAST.

Examples of agents are as described herein. In certain embodiments, the agent which modulates 14-3-3 protein functionality comprises a drug, a small molecule, a protein, a polypeptide, a lipid, a carbohydrate, a nucleic acid, a DNA, a RNA, an oligonucleotide, a ribozyme, a biologic, an aptamer, a peptide, a cofactor, a ligand, a ligand mimetic, a receptor, an enzyme, a kinase, a phosphatase, a signalling molecule, a cytokine, a growth factor, a metal ion, a chelate, an antisense nucleic acid, a siRNA, a microRNA, an antibody, and an amino acid. Other types of molecules are contemplated.

In certain embodiments, the agent which modulates 14-3-3 protein functionality comprises an agent which inhibits dimerization of a 14-3-3 protein.

In certain embodiments, the agent which inhibits dimerization of the 14-3-3 protein comprises a cationic lipid.

In certain embodiments, the agent which inhibits dimerization of the 14-3-3 protein comprises a cationic lipid comprising a heterocyclic head group. Methods of synthesizing such compounds are known in the art.

In certain embodiments, the heterocyclic group comprises a three membered ring, a four membered ring, a five membered ring or a six membered ring. Other ring sizes are contemplated. In certain embodiments, the heterocyclic group comprises one heteroatom or two heteroatoms. Examples of heteroatoms comprise one or more of nitrogen, oxygen or sulphur. In certain embodiments, the heterocyclic group is a non-aromatic heterocyclic group. In certain embodiments, the heterocyclic group is an aromatic heterocyclic group.

In certain embodiments, the heterocyclic group comprises a heterocyclic ring selected from aziridine, oxirane, thiirane, azirine, oxirene, thiirene, azetidine, oxetane, thietane, azete, oxete, thiete, pyrrolidine, oxolane, thiolane, pyrrole, furan, thiophene, piperidine, oxane, thiane, pyridine, pyran, thiopyran and/or an optionally substituted form thereof. Other types of heterocyclic groups are contemplated.

In certain embodiments, the heterocyclic head group comprises a pyrrolidine group or a piperidine group.

In certain embodiments, the heterocyclic head group is a cationic head group. In certain embodiments, the heterocyclic head group comprises a quaternary amine group. In certain embodiments, the head group comprises a quaternary heterocyclic amine.

In certain embodiments, the head group comprises a quaternary pyrrolidine group or a quaternary piperidine group. In certain embodiments, the quaternary pyrrolidine group comprises a N,N-alkyl pyrrolidine. In certain embodiments, the quaternary pyrrolidine group comprises a N,N-methyl pyrrolidine. In certain embodiments, the quaternary piperidine group comprises a N,N-alkyl piperidine. In certain embodiments, the quaternary piperidine group comprises N,N-methyl piperidine.

In certain embodiments, the agent which inhibits dimerization of the 14-3-3 protein comprises a hydrophobic tail group of at least 12 carbon atoms.

In certain embodiments, the hydrophobic tail group comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, the agent which inhibits dimerization of the 14-3-3 protein comprises a hydrophobic tail group of 12 to 20 carbon atoms.

In certain embodiments, the hydrophobic tail comprises 12 to 20 carbon atoms, 13 to 20 carbon atoms, 14 to 20 carbon atoms, 15 to 20 carbon atoms, 16 to 20 carbon atoms, 17 to 20 carbon atoms, 18 to 20 carbon atoms, 19 to 20 carbon atoms, 12 to 19 carbon atoms, 13 to 19 carbon atoms, 14 to 19 carbon atoms, 15 to 19 carbon atoms, 16 to 19 carbon atoms, 17 to 19 carbon atoms, 18 to 19 carbon atoms, 12 to 18 carbon atoms. 13 to 18 carbon atoms, 14 to IS carbon atoms, 15 to 18 carbon atoms, 16 to 18 carbon atoms, 17 to 18 carbon atoms, 12 to 17 carbon atoms, 13 to 17 carbon atoms, 14 to 17 carbon atoms, 15 to 17 carbon atoms, 16 to 17 carbon atoms, 12 to 16 carbon atoms. 13 to 16 carbon atoms, 14 to 16 carbon atoms, 15 to 16 carbon atoms, 12 to 15 carbon atoms, 13 to 15 carbon atoms, 14 to 15 carbon atoms, 12 to 14 carbon atoms, 13 to 14 carbon atoms. or 12 to 13 carbon atoms.

In certain embodiments, the hydrophobic tail group comprises a (octylphenyl)alkyl group and/or a substituted derivative thereof. In certain embodiments, the hydrophobic tail group comprises a (octylphenyl)ethyl group and or a substituted derivative thereof.

In certain embodiments, the hydrophobic tail group comprises a 2-(4-octylphenyl)ethyl group and/or a substituted derivative thereof.

In certain embodiments, the agent which inhibits dimerization of the 14-3-3 protein comprises a cationic lipid comprising a heterocyclic head group and a hydrophobic tail group of at least 12 carbon atoms.

In certain embodiments, the agent comprises a cyclic compound of formula I:

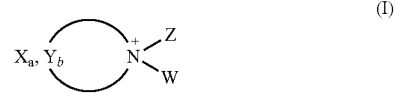

(I)

wherein:

a+b≥3;

X and Y are each independently, and in any combination or order, one of C, CH, CH$_2$, CHR$^1$, CR$^1$R$^2$, C, O, CH, O, CR$^1$, O, CHOH, CR$^1$OH, CHOR$^1$, C(OR$^1$)(OR$^2$), S, N, O, NH, NH$^+$, NR$^1$ or N(R$^1$)$^+$, and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group;

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods for synthesizing such compounds of formula I are known in the art.

In certain embodiments, the cyclic group comprises an aziridine group, an azirine group, an azetidine group, an azete group, a pyrrolidine group, a pyrrole group, a piperidine, or a pyridine group.

In certain embodiments, a+b≥4. In certain embodiments, a+b=3, 4 5, 6 or 7. In certain embodiments, a=0 and b≥3. In certain embodiments, b=0 and a≥3.

In certain embodiments, a+b=5 or 6, that is the cyclic group is a five membered ring or a six membered ring.

In certain embodiments, the cyclic group comprises one or more heteroatoms in addition to the quaternary nitrogen. Examples of heteroatoms comprise one or more of nitrogen, oxygen or sulphur.

In certain embodiments, the cyclic group is a non-aromatic cyclic group. In certain embodiments, the cyclic group is an aromatic cyclic group.

In certain embodiments, the cyclic group comprises two or more cyclic groups.

In certain embodiments, W comprises an alkyl group and/or a substituted derivative thereof. In certain embodiments, W comprises a methyl group, and/or a substituted derivative thereof In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms. In certain embodiments, Z comprises 12 to 20 carbon atoms, 13 to 20 carbon atoms, 14 to 20 carbon atoms, 15 to 20 carbon atoms, 16 to 20 carbon atoms, 17 to 20 carbon atoms, 18 to 20 carbon atoms, 19 to 20 carbon atoms, 12 to 19 carbon atoms, 13 to 19 carbon atoms, 14 to 19 carbon atoms, 15 to 19 carbon atoms, 16 to 19 carbon atoms, 17 to 19 carbon atoms, 18 to 19 carbon atoms, 12 to 18 carbon atoms, 13 to 18 carbon atoms, 14 to 18 carbon atoms, 15 to 18 carbon atoms, 16 to 18 carbon atoms, 17 to 18 carbon atoms, 12 to 17 carbon atoms, 13 to 17 carbon atoms, 14 to 17 carbon atoms, 15 to 17 carbon atoms, 16 to 17 carbon atoms, 12 to 16 carbon atoms, 13 to 16 carbon atoms, 14 to 16 carbon atoms, 15 to 16 carbon atoms, 12 to 15 carbon atoms, 13 to 15 carbon atoms, 14 to 15 carbon atoms, 12 to 14 carbon atoms, 13 to 14 carbon atoms, or 12 to 13 carbon atoms.

In certain embodiments, Z comprises an octylphenyl group and/or a substituted derivative thereof. In certain embodiments, Z comprises an (octylphenyl)alkyl group, and/or a substituted derivative thereof. In certain embodiments, Z comprises an (octylphenyl)ethyl group and/or a substituted derivative thereof.

In certain embodiments, Z comprises a 2-(4-octylphenyl) ethyl group and/or a substituted derivative thereof In certain embodiments, the agent comprises a compound of the following formula:

(II)

wherein,

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods of synthesizing compounds of formula II are known in the art.

W groups are as described herein. In certain embodiments, W comprises an alkyl group and/or a substituted derivative thereof. In certain embodiments, W comprises a methyl group and/or a substituted derivative thereof.

Z groups are as described herein. In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms.

In certain embodiments, Z comprises a 2-(4-octylphenyl) ethyl group and/or a substituted derivative thereof, In certain embodiments, the agent comprises a compound of the following formula:

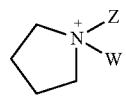

(III)

wherein,
W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;
Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods of synthesizing compounds of formula III are known in the art.

W groups are as described herein. In certain embodiments, W comprises an alkyl group or a substituted derivative thereof. In certain embodiments, W comprises a methyl group or a substituted derivative thereof.

Z groups are as described herein. In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms.

In certain embodiments, Z comprises a 2-(4-octylphenyl) ethyl group.

In certain embodiments, the agent does not comprise a phosphorylatable group.

In certain embodiments, the agent does not comprise a hydroxyl group.

In certain embodiments, the agent does not have substantial immunosuppressant activity.

In certain embodiments, the agent comprises a compound of the following formula IV:

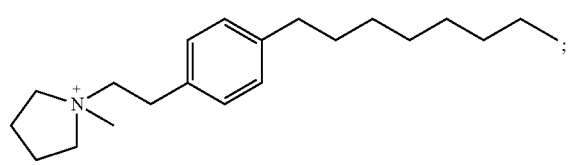

(IV)

RB-011 and/or a pharmaceutically acceptable salt or solvate thereof. Synthesis of a compound of formula IV may be achieved by a method known in the art, for example as described in D. J. Baek et al. (2013) Chem. Commun. (Camb). 49(21):2136-8. doi: 10.1039/c3cc00181d.

In certain embodiments, the agent comprises a compound of the following formula V:

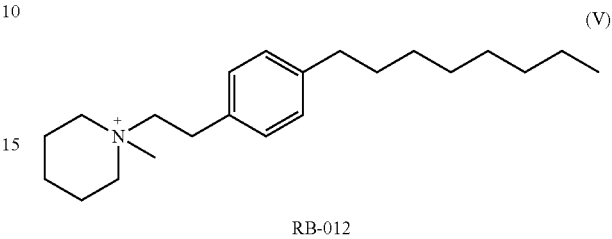

(V)

RB-012 and/or a pharmaceutically acceptable salt or solvate thereof. Synthesis of a compound of formula V may be achieved by a method known in the art, for example as described in D. J. Baek et al. (2013) Chem. Commun. (Camb). 49(21):2136-8. doi: 10.1039/c3cc00181d.

The term "agent" refers to a broad range of molecules, complexes, assemblies or aggregates. Examples of agents include a drug, a small molecule, a protein, a polypeptide, a lipid, a carbohydrate, a saccharide, an oligosaccharide, a polysaccharide, a nucleic acid, an oligonucleotide, a ribozyme, a biologic, an aptamer, a peptide, a cofactor, a ligand, a ligand mimetic, a receptor, an enzyme, a kinase, a phosphatase, a cytokine, a growth factor, a metal ion, a chelate, an antisense nucleic acid, a microRNA, a siRNA, an antibody or antigen binding part thereof, an antibody mimetic, an amino acid and/or combinations of the aforementioned. Other types of agents are contemplated.

In certain embodiments, the agent is administered to the subject at a concentration of 0.5-50 mg/kg body weight.

In certain embodiments, the agent is administered to the subject at a concentration of 0.1-100 mg/kg body weight. In certain embodiments, the agent is administered to the subject at a concentration of 0.5-50 mg/kg body weight.

In certain embodiments, the agent induces down-regulation of Raf-MAPK and/or PI3K-Akt signalling in susceptible cells.

In certain embodiments, the disease, condition or state is a cancer and the method further comprises administration of an anti-cancer agent.

Examples of anti-cancer agents include alkylating agents (such as cisplatin, carboplatin, oxaliplatin, mechlorethamine, cyclophosphamide, chlorambucil, and ifosfamide), anti-metabolites (such as azathioprine and mercaptopurine), plant alkaloids and terpenoids (such as vincristine, vinblastine, vinorelbine and vindesine), cell cycle inhibitors (such as podophyllotoxin), taxanes (such as paclitaxel), topoisomerase inhibitors (such as camptothecins, irinotecan and topotecan, amsacrine, etoposide, etoposide phosphate, and teniposide), cytotoxic antibiotics (such as actinomycin, doxorubicin, daunorubicin, valrubicin, idarubicin, epirubicin, bleomycin, plicamycin and mitomycin).

In certain embodiments, the anti-cancer agent comprises a chemotherapeutic agent.

In certain embodiments, the method further comprises screening the subject and using the screening to inform as to the details of administration of the agent.

In certain embodiments, the method further comprises screening the subject for altered expression or activity of a microRNA involved in regulation of a 14-3-3 protein and administering the agent to the subject on the basis of decreased expression or activity of the microRNA. In certain embodiments, the microRNA comprises miR-451 (miRBase Accession Number: MI0001729). In certain embodiments, the micoRNA comprises one or more of miR-7, 22, 27a, 375 and 451. In certain embodiments, the micoRNA comprises a miR-451.

The term "therapeutically effective amount" as used herein refers to that amount of an agent that is sufficient to effect prevention and/or treatment, when administered to a subject. The therapeutically effective amount will vary depending upon a number of factors, including for example the specific activity of the agent being used, the severity of the disease, condition or state in the subject, the age, physical condition, existence of other disease states, and nutritional status of the subject. Examples of therapeutic amounts are as described herein.

In certain embodiments, the agent is administered to the subject to produce a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater.

In certain embodiments, the agent is administered to the subject in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg; 1 mg/kg to 10 mg/kg; and 10 mg/kg to 100 mg/kg body weight. The dose and frequency of administration may be determined by one of skill in the art.

The agent may be administered to the subject in a suitable form. In this regard, the terms "administering" includes administering the agent, or administering a prodrug of the agent, or a derivative that will form a therapeutically effective amount of the agent within the body of the subject. The terms include routes of administration that are systemic (e.g., via injection such as intravenous injection, orally in a tablet, pill, capsule, or other dosage form useful for systemic administration of pharmaceuticals), and topical (e.g., creams, solutions, and the like, including solutions such as mouthwashes, for topical oral administration).

In certain embodiments, the agent is administered orally. In certain embodiments, the agent is administered intravenously. In certain embodiments, the agent is administered via injection such as intravenous injection. In certain embodiments, the agent is administered by nebulized administration, by aerosolized administration or by being instilled into the lung. In certain embodiments, the agent is administered topically.

The agent may be administered alone or may be delivered in a mixture with other therapeutic compounds and/or compounds that enhance, stabilise or maintain the activity of the agent In certain embodiments, an administration vehicle (e.g., pill, tablet, implant, injectable solution, etc.) would contain both the agent and additional compound(s).

The methods may also include combination therapy. In this regard, the subject is treated or given another drug or treatment modality in conjunction with the agent as described herein. This combination therapy can be sequential therapy where the subject is treated first with one and then the other, or the two or more treatment modalities are given simultaneously.

"Co-administering" or "co-administration" refers to the administration of two or more therapeutics together at one time. The two or more therapeutics can be co-formulated into a single dosage form or "combined dosage unit", or formulated separately and subsequently combined into a combined dosage unit, typically for intravenous administration or oral administration.

When administered to a subject the therapeutically effective dosage may vary depending upon the particular agent utilized, the mode of administration, the condition, and severity thereof, as well as the various physical factors related to the subject being treated. As discussed herein, suitable daily doses range from 1 µg/kg to 100 mg/kg. The daily dosages are expected to vary with route of administration, and the nature of the agent administered. In certain embodiments the methods comprise administering to the subject escalating doses of agent and/or repeated doses. In certain embodiments, the agent is administered orally. In certain embodiments, the agent is administered via injection, such as intravenous injection. In certain embodiments, the agent is administered parenterally. In certain embodiments, the agent is administered by direct introduction to the lungs, such as by aerosol administration, by nebulized administration, and by being instilled into the lung. In certain embodiments, the agent is administered by implant. In certain embodiments, the agent is administered by subcutaneous injection, intraarticularly, rectally, intranasally, intraocularly, vaginally, or transdermally. In certain embodiments, the agent is administered topically. In certain embodiments, the agent is administered by ex vivo treatment of the relevant cells, tissue or organ, followed by reintroduction into the subject.

In certain embodiments, the agent may be used in a medicament or a pharmaceutical composition. In certain embodiments, the agent may be used in a medicament or a pharmaceutical composition for use in the methods of the present disclosure as described herein. Formulations are known and described in, for example, Remington's Pharmaceutical Sciences, 17th ed., Mack Publishing Company, Easton, Pa., 1985, which is incorporated herein by reference in its entirety.

Certain embodiments of the present disclosure provide use of an agent in the preparation of a medicament or a composition, wherein the agent inhibits 14-3-3 functionality.

Certain embodiments of the present disclosure provide use of an agent in the preparation of a medicament for preventing and/or treating a disease, condition or state in a subject associated with altered 14-3-3 protein functionality and/or which would benefit from altering 14-3-3 protein functionality, wherein the agent inhibits dimerization of the 14-3-3 protein.

Agents are as described herein. Diseases, conditions and states are as described herein.

In certain embodiments, the agent comprises a cationic lipid comprising a heterocyclic head group and a hydrophobic tail group of at least 12 carbon atoms.

In certain embodiments, the agent comprises a cyclic compound of formula I:

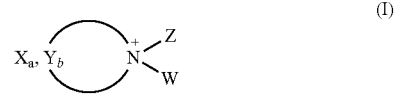

wherein;

a+b≥3;

X and Y are each independently, and in any combination or order, one of C, CH, CH$_2$, CHR$^1$, CR$^1$R$^2$, C, O, CH, O, CR$^1$, O, CHOH, CR$^1$OH, CHOR$^1$, C(OR$^1$)(OR$^2$), S, O, N, NH, NH$^+$, NR$^1$ or N(R$^1$), and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group;

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

In certain embodiments, the agent comprises a compound of the following formula IV:

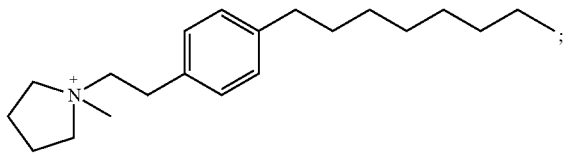

RB-011

(IV)

and/or a pharmaceutically acceptable salt or solvate thereof.

In certain embodiments, the agent comprises a compound of the following formula V:

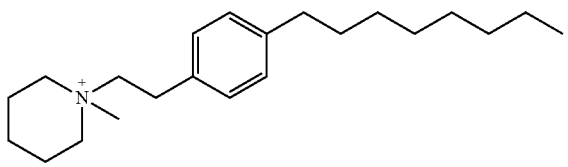

RB-012

(V)

and/or a pharmaceutically acceptable salt or solvate thereof.

Certain embodiments of the present disclosure provide a medicament or a composition, such as a therapeutic or pharmaceutical composition, comprising an agent as described herein.

Certain embodiments of the present disclosure provide a medicament or a composition comprising an agent which inhibits 14-3-3 functionality. Examples of agents are as described herein.

Certain embodiments of the present disclosure provide a medicament or a composition comprising an agent which inhibits dimerization of the 14-3-3 protein.

Certain embodiments of the present disclosure provide a medicament or a composition comprising an agent which comprises a cationic lipid comprising a heterocyclic head group and a hydrophobic tail group of at least 12 carbon atoms.

Certain embodiments of the present disclosure provide a medicament or a composition comprising an agent which comprises a cyclic compound of formula I:

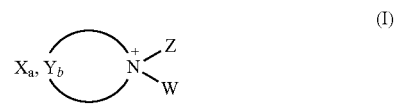

(I)

wherein:

a+b≥3;

and Y are each independently, and in any combination or order, one of C, CH, CH$_2$, CHR$^1$, CR$^1$R$^2$, C, O, CH, O, CR$^1$O, CHOH, CR$^1$OH, CHOH, C(OR$^1$)(OR$^2$), S, O, N, NH, NH$^+$, NR$^1$ or N(R$^1$), and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group;

W is H, optionally substituted alkyl, optionally substituted alkenyl, optionally substituted alkenyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkenyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Certain embodiments of the present disclosure provide a medicament or a composition comprising an agent which comprises a compound of the following formula IV:

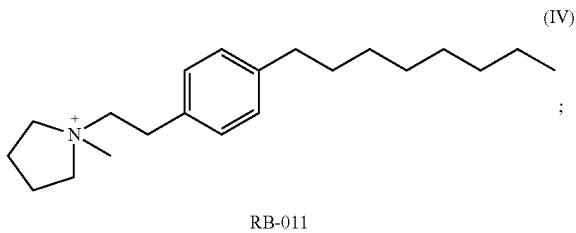

RB-011 and/or a pharmaceutically acceptable salt or solvate thereof.

Certain embodiments of the present disclosure provide a medicament or a composition comprising an agent which comprises a compound of the following formula V:

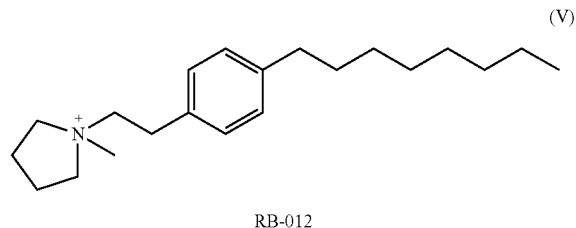

RB-012 and/or a pharmaceutically acceptable salt or solvate thereof.

In certain embodiments, the composition comprises an anti-cancer composition.

In certain embodiments, the agent is present in a medicament or a composition so as to produce a concentration of the agent in the subject of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the agent in a medicament or a is present so as to provide an amount of agent for administration to the subject in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg; 1 mg/kg to 10 mg/kg; and 10 mg/kg to 100 mg/kg body weight. Other amounts are contemplated.

In certain embodiments, the medicament or composition comprises an amount of the agent for administration from one of the following selected ranges: 1 µg to 1000 mg; 1 µg to 100 mg; 1 µg to 1 mg; 1 µg to 100 µs; 1 µg to 10 µg; 10 µg to 100 mg; 10 µg to 1000 mg; 10 µg to 100 mg; 10 µg to 10 mg; 10 µg to 1 mg; 10 µg to 100 µg; 100 µg to 1000 mg; 100 µg to 100 mg; 100 µg to 10 mg; 100 µg to 1 mg; 1 mg to 1000 mg; 1 mg to 100 mg; 1 mg to 10 mg; 10 mg to 1000 mg; and 10 mg to 100 mg. Other amounts are contemplated.

In certain embodiments, the medicament or composition is suitable for delivery to the subject by one or more of intravenous administration, intratracheal administration, by nebulized administration, by aerosolized administration, by instillation into the lung, by oral administration, by topical administration, by parenteral administration, by implant, by subcutaneous injection, intraarticularly, rectally, intranasally, intraocularly, vaginally, or transdermally.

In certain embodiments, the agent is provided in an acceptable carrier suitable for administration. Carriers may be chosen based on the route of administration as described herein, the location of the target issue, the agent being delivered, the time course of delivery, etc. The term "acceptable carrier" refers to a substantially inert solid, semi-solid or liquid filler, diluent, encapsulating material or formulation auxiliary of any type. An example of an acceptable carrier is physiological saline. Other physiologically acceptable carriers and their formulations are known in the art. Some examples of materials which can serve as carriers include, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminium hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present.

In certain embodiments, the agent may be administered or present in a medicament or a composition as a pharmaceutically acceptable salt. The term "pharmaceutically acceptable salt" refers to acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

In certain embodiments, the compositions or medicaments comprise other therapeutic compounds and/or compounds that enhance, stabilise or maintain the activity of the active.

Oral formulations for use containing an agent as described herein may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminium silicate, and triethanolamine. Oral formulations may utilize standard delay or time-release formulations to alter the absorption of the peptides. The oral formulation may also consist of administering the active ingredient in water or a fruit juice, containing appropriate solubilizers or emulsifiers as needed.

In certain embodiments, it may be desirable to administer the agent directly to the airways in the form of an aerosol. Formulations for the administration of aerosol forms are known.

In certain embodiments, it may be desirable to administer the agent parenterally (such as directly into the joint space) or intraperitoneally. For example, solutions or suspensions of these compounds in a non-ionised form or as a pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations typically contain a preservative to prevent the growth of microorganisms.

In certain embodiments, it may be desirable to administer the agent by injection. Pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol and liquid polyethylene glycol), suitable mixtures thereof, and vegetable oils.

In certain embodiments, it may be desirable to administer the agent intravenously. Compositions containing the agent described herein suitable for intravenous administration may be formulated by a skilled person.

In certain embodiments, it may be desirable to administer the agent transdermally. Transdermal administrations are understood to include all administrations across the surface of the body and the inner linings of bodily passages including epithelial and mucosal tissues. Such administrations may be carried out using the inhibitor as described herein, or pharmaceutically acceptable salts thereof, in lotions, creams, foams, patches, suspensions, solutions, and suppositories (rectal and vaginal).

Transdermal administration may also be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient.

In certain embodiments, it may be desirable to administer the agent by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, it may be desirable to administer the agent topically. Examples of topical administration include administration using a gel, an ointment, a cream, a lotion, a foam, an emulsion, a suspension, a spray, an aerosol, a solution, a liquid, a powder, a semi-solid, a gel, a jelly, a suppository; a solid, an ointment, a paste, a tincture, a linament, a patch, or release from a bandage, gauze or dressing.

Additional numerous various excipients, dosage forms, dispersing agents and the like that are suitable for use in connection with the administration of the inhibitor and/or the formulation into medicaments or pharmaceutical compositions.

Formulations are known and described in, for example, Remington's Pharmaceutical Sciences, 17th ed., Mack Publishing Company, Easton, Pa., 1985, which is incorporated herein by reference in its entirety.

Certain embodiments of the present disclosure provide a method of preventing and/or treating a disease, condition or state in a subject as described herein by administering to the subject a medicament or a composition as described herein.

Certain embodiments of the present disclosure provide a method of preventing and/or treating a disease, condition or state in a subject associated with altered 14-3-3 protein functionality and/or which would benefit from altering 14-3-3 protein functionality, the method comprising administering to the subject an effective amount of medicament or a composition as described herein, thereby preventing and/or treating the disease, condition or state in the subject.

Certain embodiments of the present composition provide an anti-cancer composition comprising a therapeutically effective amount of an agent as described herein.

Examples of cancers are as described herein.

Certain embodiments of the present composition provide an anti-cancer composition comprising a therapeutically effective amount of an agent which inhibits 14-3-3 protein functionality. Examples of compositions are as described herein.

Certain embodiments of the present composition provide an anti-cancer composition comprising a therapeutically effective amount of an agent which inhibits dimerization of a 14-3-3 protein.

Certain embodiments of the present composition provide an anti-cancer composition comprising a therapeutically effective amount of an agent comprising a cationic lipid comprising a heterocyclic head group and a hydrophobic tail group of at least 12 carbon atoms.

Certain embodiments of the present disclosure provide an anti-cancer composition comprising an agent which comprises a cyclic compound of formula I:

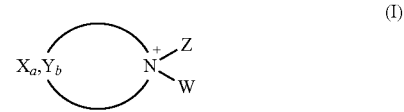

(I)

wherein;

a+b≥3;

X and Y are each independently, and in any combination or order. one of C, CH, CH$_2$, CHR$^1$, CR$^1$R$^2$, C, O, CH, O, CR$^1$, O, CHOH, CR$^1$OH, CHOH$^1$, C(OR$^1$)(OR$^2$), S, O, N, NH, NH$^+$, NR$^1$ or N(R$^1$), and R$^1$ and R$^2$ are each independently is an optionally substituted alkyl, optionally substituted alkenyl, optionally substituted optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group;

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Certain embodiments of the present disclosure provide an anti-cancer composition comprising an agent which comprises a compound of the following formula IV:

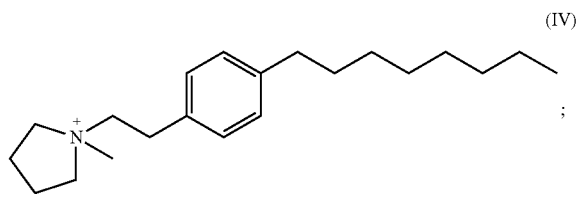

(IV)

RB-011 and/or a pharmaceutically acceptable salt or solvate thereof.

Certain embodiments of the present disclosure provide an anti-cancer composition comprising an agent which comprises a compound of the following formula V:

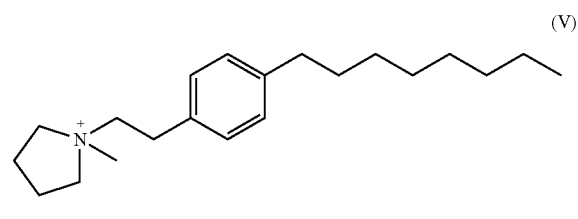

(V)

RB-012 and/or a pharmaceutically acceptable salt or solvate thereof.

Certain embodiments of the present disclosure provide a method of preventing and/or treating a cancer in a subject associated with altered 14-3-3 protein functionality, the method comprising administering to the subject an effective amount of an anti-cancer composition as described herein.

Certain embodiments of the present disclosure provide a combination product comprising an agent as described herein and one or more other compounds.

Certain embodiments of the present disclosure provide a combination product, the product comprising the following components:

an agent as described herein; and an anti-cancer agent;

wherein the components are provided in a form for separate or co-administration to a subject in need thereof.

Certain embodiments of the present disclosure provide a combination product, the product comprising the following components:

an agent which inhibits dimerization of a 14-3-3 protein; and an anti-cancer agent;

wherein the components are provided in a form for separate or co-administration to a subject in need thereof.

Certain embodiments of the present disclosure provide a combination product, the product comprising the following components:

an agent comprising a cationic lipid comprising a heterocyclic head group and a hydrophobic tail group of at least 12 carbon atoms; and an anti-cancer agent, wherein the components are provided in a form for separate or co-administration to a subject in need thereof.

Certain embodiments of the present disclosure provide a method of increasing the sensitivity of a cancer in a subject to treatment with an anti-cancer agent.

Certain embodiments of the present disclosure provide a method of increasing the sensitivity of a cancer in a subject to treatment with a chemotherapeutic agent.

Certain embodiments of the present disclosure provide a method of increasing the sensitivity of a cancer in a subject to treatment with an anti-cancer agent, the method comprising administering to the subject an inhibitor of 14-3-3 protein functionality, thereby increasing the sensitivity of the cancer to treatment with the anti-cancer agent.

Certain embodiments of the present disclosure provide a method of increasing the sensitivity of a cancer in a subject to treatment with an anti-cancer agent, the method comprising administering to the subject an effective amount of an agent which inhibits dimerization of the 14-3-3 protein, thereby increasing the sensitivity of the cancer to treatment with the anti-cancer agent.

Certain embodiments of the present disclosure provide a method of increasing the sensitivity of a cancer in a subject to treatment with a chemotherapeutic agent, the method comprising administering to the subject an effective amount of an agent which inhibits dimerization of the 14-3-3 protein, thereby increasing the sensitivity of the cancer to treatment with the chemotherapeutic agent.

Examples of agents are as described herein. Methods for determining the sensitivity of a cancer to a therapeutic agent are known in the art.

Examples of cancers are as described herein.

Certain embodiments of the present disclosure provide a method of promoting or increasing apoptosis of a cell by exposing the cell to an agent as described herein.

Certain embodiments of the present disclosure provide a method of promoting apoptosis of a cell, the method comprising exposing the cell to an effective amount of an agent that inhibits dimerization of a 14-3-3 protein, thereby promoting apoptosis of the cell.

Methods for assessing apoptosis are known in the art.

In certain embodiments, the apoptosis comprises mitochondrial-mediated apoptosis.

In certain embodiments, the agent comprises a cationic lipid comprising a heterocyclic head group and a hydrophobic tail group of at least 12 carbon atoms.

In certain embodiments, the agent comprises a cyclic compound of formula I:

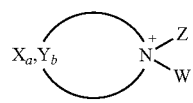

(I)

wherein;

$a+b \geq 3$;

X and Y are each independently, and in any combination or order, one of C, CH, CH$_2$, CHR$^1$, CR$^1$R$^2$, C, O, CH, O, CR$^1$, O, CHOH, CR$^1$OH, CHOR$^1$, C(OR$^1$)(OR$^2$), S, O, N, NH, NH$^+$, or NR$^1$ or N(R$^1$), and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group:

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy. optionally substituted arylalkoxy, optionally substituted heteroarylalkoxy, or a combination of any of the aforementioned:

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

In certain embodiments, the agent comprises a compound of the following formula IV:

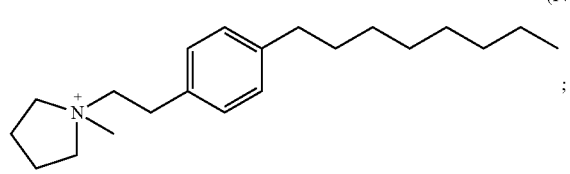

(IV)

RB-011 and/or a pharmaceutically acceptable salt or solvate thereof.

In certain embodiments, the agent comprises a compound of the following formula V:

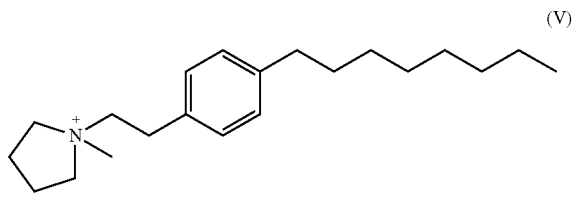

(V)

RB-012 and/or a pharmaceutically acceptable salt or solvate thereof.

In certain embodiments, the agent induces rapid down-regulation of Raf-MAPK and/or PI3K-Akt signalling in the cell.

The term "exposing", and related terms such as "expose" and "exposure", refers to directly and/or indirectly contacting and/or treating a species (for example a cancerous cell) with the agent. The term "effective amount" as used herein refers to that amount of the agent that when exposed to a cell or another species is sufficient to illicit the desired response or outcome. The effective amount will vary depending upon a number of factors, including for example the specific activity of the agent being used and the cell type.

In certain embodiments, the cell is associated with a disease, condition or state is a cancer, a solid cancer, a non-solid cancer, a neoplastic disease, an inflammatory disease, condition or state, or a neurodegenerative disease, condition or state.

In certain embodiments, the cell is a cancerous cell, a pre-cancerous cell, a cell from a primary tumour, a cell from a secondary tumour or a metastatic cell.

Examples of cancerous cells include cancerous cells from cancers as described herein. In certain embodiments, the cancerous cell is a solid cancer cell. In certain embodiments, the cancerous cell is a non-solid cancer cell. In certain embodiments, the cancerous cell is a carcinoma cell. In certain embodiments, the cancerous cell is a sarcoma cell. In certain embodiments, the cancerous cell is a lymphoma cell. In certain embodiments, the cancer cell is a germ cell cancerous cell. In certain embodiments, the cancerous cell is a blastoma cell. In certain embodiments, the cancerous cell is a haematological cancerous cell.

In certain embodiments, the cancerous cell is a melanoma cell, a cancerous breast cell, a cancerous prostate cell, a cancerous ovarian cell, a cancerous lung cell, a cancerous colorectal cell, a cancerous gastric cell, a cancerous pancreatic cell, a cancerous bladder cell, a cancerous oesophageal cell, a cancerous urothelial cell, a cancerous non-small cell lung cell, a cancerous head and neck cell, a cancerous ovarian cell, a cancerous testicular cell, a cancerous uterine cell, a cancerous liver cell, a cancerous renal cell, a cancerous stomach cell, a cancerous brain cell, a malignant myeloma cell, a cancerous blood borne cell, a cancerous CML cell, a cancerous AML cell, or a cell from a lymphoproliferative tumour.

In certain embodiments, the cell is a cell associated with a disease, condition or state as described herein.

In certain embodiments, the cell comprises one or more cells in vivo. For one or more cells in vivo, the agent may be administered to a subject to expose cells to the agent, or another compound may be administered to a subject that results in the production of the agent in the subject, thereby exposing cells in vivo to an inhibitor.

In certain embodiments, the cell comprises one or more cells ex vivo. For example, one or more cells may be removed from a subject and contacted directly or indirectly with the agent, and cells then introduced back into the same or another subject to effect exposure to the agent. For example, a cancerous cell may exposed to an inhibitor ex vivo, and subsequently be introduced into a subject.

In certain embodiments, the cell comprises one or more cells in vitro. Cells in vitro include one or more isolated cells (eg isolated by flow cytometry), one or more cells in tissue culture. Other types of in vitro settings are contemplated.

In certain embodiments, a cell is exposed to a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the cell comprises increased or dysregulated 14-3-3 protein expression.

In certain embodiments, the cell comprises a bcr-abl oncogene.

In certain embodiments, the cell is a cancerous cell from a chronic myelogenous leukaemia, an acute lymphoblastic leukaemia, or a chronic neutrophilic leukaemia.

In certain embodiments, the cell is a cancerous cell from a late form of chronic myelogenous leukaemia.

Certain embodiments of the present disclosure provide a method of inhibiting proliferation of a cell by exposing the cell to an agent as described herein.

Certain embodiments of the present disclosure provide a method of inhibiting proliferation of a cell, the method comprising exposing the cell to an effective amount of an agent that inhibits dimerization of a 14-3-3 protein, thereby inhibiting proliferation of the cell.

Methods for assessing cell proliferation are known in the art.

In certain embodiments, the agent comprises a cationic lipid comprising a heterocyclic head group and a hydrophobic tail group of at least 12 carbon atoms.

In certain embodiments, the agent comprises a cyclic compound of formula I:

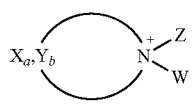

(I)

wherein:

$a+b \geq 3$;

X and Y are each independently, and in any combination or order, one of C, CH, CH$_2$, CHR$^1$, CR$^1$R$^2$, C, O, CH, O, CR$^1$O, CHOH, CR$^1$OH, CHOH, C(OR$^1$)(OR$^2$), S, O, N, NH, NH$^+$, NR$^1$ or N(R$^1$), and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group;

W is H, optionally substituted alkyl, optionally substituted alkenyl, optionally substituted alkenyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned. and/or a pharmaceutically acceptable salt or solvate thereof.

In certain embodiments, the agent comprises a compound of the following formula IV:

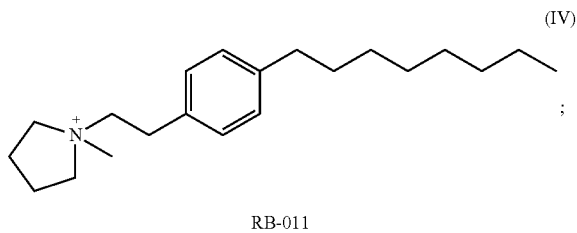

RB-011 and/or a pharmaceutically acceptable salt or solvate thereof.

In certain embodiments, the agent comprises a compound of the following formula V:

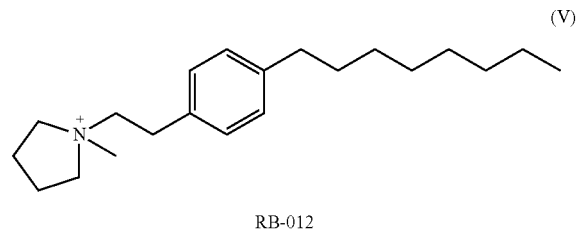

RB-012 and/or a pharmaceutically acceptable salt or solvate thereof.

In certain embodiments, the agent induces down-regulation of Raf-MAPK and/or PI3K-Akt signalling in the cell.

In certain embodiments, the cell is associated with a disease, condition or state is a cancer, a solid cancer, a non-solid cancer, a neoplastic disease, an inflammatory disease, condition or state, or a neurodegenerative disease, condition or state.

In certain embodiments, the cell is a cancerous cell, a pre-cancerous cell, a cell from a primary tumour, a cell from a secondary tumour or a metastatic cell.

Examples of cancerous cells include cancerous cells from cancers as described herein. In certain embodiments, the cancerous cell is a solid cancer cell. In certain embodiments, the cancerous cell is a non-solid cancer cell. In certain embodiments, the cancerous cell is a carcinoma cell. In certain embodiments, the cancerous cell is a sarcoma cell. In certain embodiments, the cancerous cell is a lymphoma cell. In certain embodiments, the cancer cell is a germ cell cancerous cell. In certain embodiments, the cancerous cell is a blastoma cell. In certain embodiments, the cancerous cell is a haematological cancerous cell.

In certain embodiments, the cancerous cell is a melanoma cell, a cancerous breast cell, a cancerous prostate cell, a cancerous ovarian cell, a cancerous lung cell, a cancerous colorectal cell, a cancerous gastric cell, a cancerous pancreatic cell, a cancerous bladder cell, a cancerous oesophageal cell, a cancerous urothelial cell, a cancerous non-small cell lung cell, a cancerous head and neck cell, a cancerous ovarian cell, a cancerous testicular cell, a cancerous uterine cell, a cancerous liver cell, a cancerous renal cell, a cancerous stomach cell, a cancerous brain cell, a malignant myeloma cell, a blood borne cancerous cell, a cancerous CML cell, a cancerous AML cell, or a cell from a lymphoproliferative tumour.

In certain embodiments, the cell is a cell associated with a disease, condition or state as described herein.

In certain embodiments, the cell comprises one or more cells in vivo. For one or more cells in vivo, the agent may be administered to a subject to expose cells to the agent, or another compound may be administered to a subject that results in the production of the agent in the subject, thereby exposing cells in vivo to an inhibitor.

In certain embodiments, the cell comprises one or more cells ex vivo. For example, one or more cells may be removed from a subject and contacted directly or indirectly with the agent, and cells then introduced back into the same or another subject to effect exposure to the agent. For example, a cancerous cell may exposed to an inhibitor ex vivo, and subsequently be introduced into a subject.

In certain embodiments, the cell comprises one or more cells in vitro. Cells in vitro include one or more isolated cells (eg isolated by flow cytometry), one or more cells in tissue culture. Other types of in vitro settings are contemplated.

In certain embodiments, a cell is exposed to a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the cell comprises increased or dysregulated 14-3-3 protein expression.

In certain embodiments, the cell comprises a bcr-abl oncogene.

In certain embodiments, the cell is a cancerous cell from a chronic myelogenous leukaemia, an acute lymphoblastic leukaemia, or a chronic neutrophilic leukaemia.

In certain embodiments, the cell is a cancerous cell from a late form of chronic myelogenous leukaemia.

Certain embodiments of the present disclosure provide a method of inhibiting dimerization of a 14-3-3 protein by exposing the protein to an agent as described herein.

Certain embodiments of the present disclosure provide a method of inhibiting dimerization of a 14-3-3 protein, the method comprising exposing the 14-3-3 protein to an effective amount of an agent comprising a cationic lipid comprising a heterocyclic head group and a hydrophobic tail group of at least 12 carbon atoms.

Methods for assessing dimerization of proteins are known in the art.

14-3-3 proteins are as described herein. In certain embodiments, the 14-3-3 protein comprises a 14-3-3ζ protein.

In certain embodiments, the agent comprises a cyclic compound of formula I:

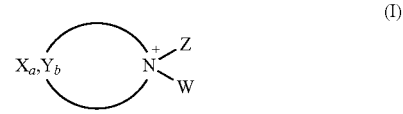

wherein;

$a+b \geq 3$;

X and Y are each independently, and in any combination or order, one of C, CH, CH$_2$, CHR$^1$, CR$^1$R$^2$, C, O, CH, O, CR$^1$, O, CHOH, CR$^1$OH, CHOR$^1$, C(OR$^1$)(OR$^2$), S, O, N, NH, NH$^+$, NR$^1$ or N(R$^1$), and R$^1$ and R$^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R$^1$ and R$^2$ form part of a cyclic or heterocyclic group:

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy. optionally substituted arylalkoxy, optionally substituted heteroarylalkoxy, or a combination of any of the aforementioned:

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and or a pharmaceutically acceptable salt or solvate thereof.

In certain embodiments, the agent comprises a compound of the following formula IV:

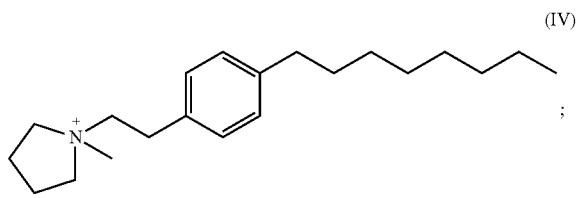

RB-011 and/or a pharmaceutically acceptable salt or solvate thereof.

In certain embodiments, the agent comprises a compound of the following formula V:

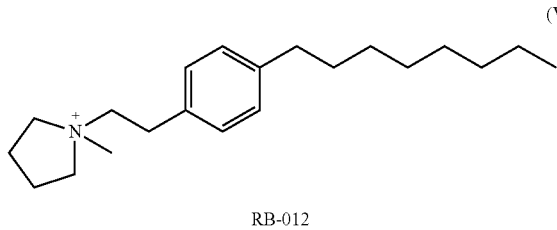

RB-012 and/or a pharmaceutically acceptable salt or solvate thereof.

In certain embodiments, the 14-3-3 protein is in vivo. In certain embodiments, the 14-3-3 protein is present in a cell in vitro.

In certain embodiments, the 14-3-3 protein is in vitro. For example, use of the agents as described herein as research reagents is also contemplated.

In certain embodiments, the 14-3-3 protein is present in a cell associated with a disease, condition or state is a cancer, a solid cancer, a non-solid cancer, a neoplastic disease, an inflammatory disease, condition or state, or a neurodegenerative disease, condition or state. Examples are described herein.

In certain embodiments, the cell is a cancerous cell, a pre-cancerous cell, a cell from a primary tumour, a cell from a secondary tumour or a metastatic cell. Examples of cancerous cells are described herein.

In certain embodiments, the 14-3-3 protein is exposed to a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the 14-3-3 protein is present in a cell with increased or dysregulated 14-3-3 protein expression.

In certain embodiments, the 14-3-3 protein is present in a cell comprising a bcr-abl oncogene.

In certain embodiments, the 14-3-3 protein is present in a cell from a chronic myelogenous leukaemia, an acute lymphoblastic leukaemia, or a chronic neutrophilic leukaemia.

In certain embodiments, the 14-3-3 protein is present in a cell from a late form of chronic myelogenous leukaemia.

In certain embodiments, the method is used to modulate Raf-MAPK signalling, PI3K-AKT signalling, to modulate apoptosis, to modulate cell viability, and/or to modulate cell proliferation.

In certain embodiments, the method is used to decrease Raf-MAPK signalling and/or decrease PI3K-AKT signalling.

In certain embodiments, the method is used to promote apoptosis, to reduce cell viability, and/or to reduce cell proliferation.

Certain embodiments of the present disclosure provide a method of promoting phosphoylation of a 14-3-3 protein by exposing the protein to an agent as described herein.

Certain embodiments of the present disclosure provide a method of promoting phosphoylation of a 14-3-3 protein, the method comprising exposing the 14-3-3 protein to an effective amount of an agent which inhibits dimerization of a 14-3-3 protein. Examples of agents are as described herein.

Certain embodiments of the present disclosure provide a method of promoting phoshoylation of a 14-3-3 protein, the method comprising exposing the 14-3-3 protein to an effective amount of an agent comprising a cationic lipid comprising a heterocyclic head group and a hydrophobic tail group of at least 12 carbon atoms.

Methods for assessing phosphoylation of proteins are known in the art.

14-3-3 proteins are as described herein. In certain embodiments, the 14-3-3 protein comprises a 14-3-3ζ protein.

In certain embodiments, the agent comprises a cyclic compound of formula I:

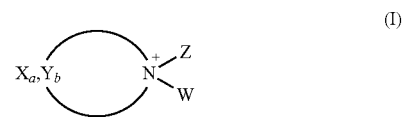

wherein:

$a+b \geq 3$;

X and Y are each independently, and in any combination or order, one of C, CH, $CH_2$, $CHR^1$, $CR^1R^2$, C, O, CH, O, $CR^1$, O, CHOH, $CR^1OH$, $CHOR^1$, $C(OR^1)(OR^2)$, S, O, N, NH, $NH^+$, $NR^1$ or $N(R^1)$, and $R^1$ and $R^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or $R^1$ and $R^2$ form part of a cyclic or heterocyclic group:

W is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

In certain embodiments, the agent comprises a compound of the following formula IV:

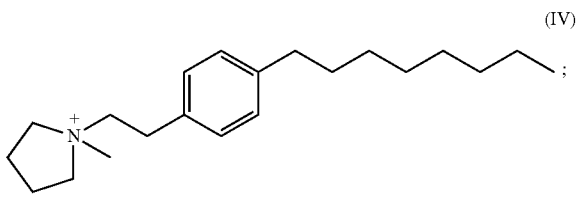

RB-011 and/or a pharmaceutically acceptable salt or solvate thereof.

In certain embodiments, the agent comprises a compound of the following formula V:

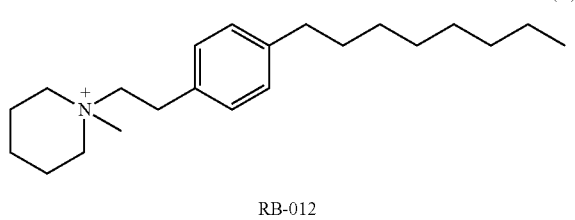

(V)

RB-012 and/or a pharmaceutically acceptable salt or solvate thereof.

In certain embodiments, the 14-3-3 protein is in vivo. In certain embodiments, the 14-3-3 protein is present in a cell in vitro.

In certain embodiments, the 14-3-3 protein is in vitro. For example, use of the agents as described herein as research reagents is also contemplated.

In certain embodiments, the 14-3-3 protein is present in a cell associated with a disease, condition or state is a cancer, a solid cancer, a non-solid cancer, a neoplastic disease, an inflammatory disease, condition or state, or a neurodegenerative disease, condition or state. Examples are described herein.

In certain embodiments, the cell is a cancerous cell, a pre-cancerous cell, a cell from a primary tumour, a cell from a secondary tumour or a metastatic cell. Examples of cancerous cells are described herein.

In certain embodiments, the 14-3-3 protein is exposed to a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the 14-3-3 protein is present in a cell with increased or dysregulated 14-3-3 protein expression.

In certain embodiments, the 14-3-3 protein is present in a cell comprising a bcr-abl oncogene.

In certain embodiments, the 14-3-3 protein is present in a cell from a chronic myelogenous leukaemia, an acute lymphoblastic leukaemia, or a chronic neutrophilic leukaemia.

In certain embodiments, the 14-3-3 protein is present in a cell from a late form of chronic myelogenous leukaemia.

In certain embodiments, the method is used to modulate Raf-MAPK signalling, PI3K-AKT signalling, to inhibit 14-3-3 dimerization, to modulate apoptosis, to modulate cell viability, and/or to modulate cell proliferation.

In certain embodiments, the method is used to decrease Raf-MAPK signalling and/or decrease PI3K-AKT signalling.

Certain embodiments of the present disclosure provide a method of identifying an inhibitor of 14-3-3 protein dimerization. Such inhibitors have therapeutic potential as described herein.

14-3-3 proteins are as described herein.

Certain embodiments of the present disclosure provide a method of identifying an inhibitor of dimerization of a 14-3-3 protein, the method comprising:
 exposing a 14-3-3 protein to a candidate agent comprising a cationic lipid comprising a heterocyclic head group and a hydrophobic tail group of at least 12 carbon atoms;
 determining the ability of the candidate agent to inhibit dimerization of the 14-3-3 protein; and
 identifying the candidate agent as an inhibitor of dimerization of a 14-3-3 protein.

Certain embodiments of the present disclosure provide a method of identifying an inhibitor of dimerization of a 14-3-3 protein, the method comprising:
 exposing a 14-3-3 protein to an agent as described herein;
 determining the ability of the agent to inhibit dimerization of the 14-3-3 protein; and
 identifying the agent as an inhibitor of dimerization of a 14-3-3 protein.

Methods for determining the ability of a candidate agent to inhibit dimerization of a 14-3-3 protein are known in the art.

14-3-3 proteins are as described herein. In certain embodiments, the 14-3-3 protein comprises a 14-3-3ζ protein.

In certain embodiments, the candidate agent induces down-regulation of Raf-MAPK and/or PI3K-Akt signalling.

In certain embodiments, the method is used to identify an anti-cancer agent. Examples of cancers are as described herein.

Certain embodiments of the present disclosure provide an agent identified using the methods as described herein. In certain embodiments, the agent comprises an anti-cancer agent.

Examples of test/candidate agents include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, an enzyme, a kinase, a phosphatase, a cytokine, a growth factor, a metal ion, a chelate, an antisense nucleic acid, an antisense RNA, a microRNA, a siRNA, an antibody or antigen binding part thereof. Other types of agents are contemplated.

Certain embodiments of the present disclosure provide a method of identifying an agent for the prevention and/or treatment of a disease, condition or state associated with altered 14-3-3 protein functionality.

Certain embodiments of the present disclosure provide a method of identifying an agent for the prevention and/or treatment of a disease, condition or state associated with altered 14-3-3 protein functionality, the method comprising:
 determining the ability of an agent as described to inhibit dimerization of a 14-3-3 protein; and
 identifying the agent as an agent for the prevention and/or treatment of a disease, condition or state associated with altered 14-3-3 protein functionality.

Certain embodiments of the present disclosure provide a method of identifying an agent for the prevention and/or treatment of a disease, condition or state associated with altered 14-3-3 protein functionality, the method comprising:
 determining the ability of a candidate agent comprising a cationic lipid comprising a heterocyclic head group and a hydrophobic tail group of at least 12 carbon atoms to inhibit dimerization of a 14-3-3 protein; and
 identifying the candidate agent as an agent for the prevention and/or treatment of a disease, condition or state associated with altered 14-3-3 protein functionality.

Methods for determining the ability of a candidate agent to inhibit dimerization of a 14-3-3 protein are known in the art.

14-3-3 proteins are as described herein. In certain embodiments, the 14-3-3 protein comprises a 14-3-3ζ protein.

In certain embodiments, the candidate agent induces down-regulation of Raf-MAPK and/or PI3K-Akt signalling.

Methods for determining the ability of a candidate/test agent to prevent and/or treat a disease, condition or state associated with altered 14-3-3 protein functionality are known in the art. Such methods typically utilise testing the agent in a suitable animal model.

In certain embodiments, the disease, condition or state comprises a cancer. Cancers are as described herein.

Certain embodiments of the present disclosure provide an agent identified using the methods as described herein. In certain embodiments, the agent comprises an anti-cancer agent.

Certain embodiments of the present disclosure provide a method of screening agents using a method as described herein.

Certain embodiments of the present disclosure provide a method of modulating healing of a wound in a subject.

Certain embodiments of the present disclosure provide a method of modulating healing of a wound in a subject, the method comprising modulating 14-3-3 protein functionality in the subject and thereby modulating healing of the wound in the subject.

As used herein, the term "wound" includes an injury to a tissue, including for example, open wounds, delayed or difficult to heal wounds, and chronic wounds. Examples of wounds may include both open and closed wounds. The term "wound" also includes, for example, injuries to the skin and subcutaneous tissue and injuries initiated in different ways and with varying characteristics.

In certain embodiments, the wound is an external wound. In certain embodiments, the wound is an open wound. In certain embodiments, the wound is a chronic wound. In certain embodiments, the wound is a chronic wound or an ulcer.

For external wounds, typically these wounds are classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds wherein bones are exposed (e.g., a bony pressure point such as the greater trochanter or the sacrum).

14-3-3 proteins are as described herein. In certain embodiments, the 14-3-3 protein comprises a 14-3-3 protein selected from the group consisting of a 14-3-3ζ protein, a 14-3-3η protein, a 14-3-3γ protein, a 14-3-3ε protein, and a 14-3-3β protein.

In certain embodiments, the 14-3-3 protein comprises a 14-3-3ζ protein.

In certain embodiments, the modulating comprises a promotion, increase, enhancement, or stimulation of 14-3-3 protein functionality. In certain embodiments, the modulating comprises an inhibition or decrease of 14-3-3 protein functionality.

In certain embodiments, the modulating of healing of a wound comprises promoting healing of a wound. Methods for assessing wound healing are known in the art.

In certain embodiments, healing of a wound is promoted by inhibiting 14-3-3 protein functionality.

Certain embodiments of the present disclosure provide a method of promoting healing of a wound in a subject, the method comprising administering to the subject an effective amount of an agent which inhibits 14-3-3 protein functionality, thereby promoting healing of the wound in the subject.

In certain embodiments, the modulating of healing of a wound comprises inhibiting or delaying healing of a wound.

In certain embodiments, the subject is suffering from a wound. In certain embodiments, the subject is suffering from an open wound. In certain embodiments, the subject is suffering from a chronic wound. In certain embodiments, the subject is susceptible to developing a chronic wound or an ulcer. In certain embodiments, the subject is suffering from, or susceptible, to diabetes.

Examples of subjects are as described herein. In certain embodiments, the subject is a human or animal subject. In certain embodiments, the subject is a human subject.

Methods for administration of an agent are as described herein.

Certain embodiments of the present disclosure provide a method of treating a subject suffering from a wound.

Certain embodiments of the present disclosure provide a method of treating a subject suffering from a wound, the method comprising administering to the subject an effective amount of an agent which inhibits 14-3-3 protein functionality, thereby treating the wound in the subject.

In certain embodiments, the inhibiting of 14-3-3 functionality comprises a gene knock out and/or a gene knock down. Methods for producing a gene knockout or a gene knock down are known. For example, gene knock outs are as described in "Gene Knockout Protocols" (2001), edited by Martin J. Tymms, Ismail Kola, Human Press Inc. Gene knock downs are as described in "Regulation of Gene Expression by Small RNAs" (2009) edited by Rajesh K. Gaur, John J. Rossi, CRC Press.

In certain embodiment, the gene knock out is a homozygous gene knock out. In certain embodiments, the gene knock out is a heterozygous gene knock out.

In certain embodiments, a gene knock out and/or the gene knock down comprises a knock out and/or a knock down of a 14-3-3 gene. In certain embodiments, a gene knock out and/or the gene knock down comprises a knock out and/or a knock down of a gene that regulates the expression of a 14-3-3 gene. The knock out and/or a knock down of other genes is contemplated.

In certain embodiments, the subject comprises a gene knock out and/or a gene knock down. In certain embodiments, the subject comprises a homozygous gene knock out or a homozygous gene down. In certain embodiments, the subject comprises a heterozygous gene knock out or a knock down In certain embodiments, the modulating of 14-3-3 functionality comprises exposing the subject to an agent that modulates 14-3-3 functionality. The term "exposing", and related terms such as "expose" and "exposure", refers to directly and/or indirectly contacting and/or treating a biological system with an agent In certain embodiments, the modulating of 14-3-3 functionality comprises administering to the subject an agent that modulates 14-3-3 functionality.

Certain embodiments of the present disclosure provide a method of modulating healing of a wound in a subject, the method comprising administering to the subject an effective amount of an agent which modulates 14-3-3 protein functionality, thereby modulating healing of the wound in the subject.

For example, the agent may change activity of a 14-3-3 protein, the agent may change localisation of a 14-3-3 protein, the agent may change the synthesis and/or degradation rates of a 14-3-3 protein, the agent may change the timing of 14-3-3 protein activity or expression, the agent may change the ability of the 14-3-3 protein to interact with itself or other species, the agent may change the chemical composition of a 14-3-3 protein, and the agent may change signalling events associated with a 14-3-3 protein. In a similar manner, the agent may also change upstream or downstream effectors of 14-3-3 functionality.

In certain embodiments, the agent promotes 14-3-3 protein functionality.

In certain embodiments, the agent inhibits 14-3-3 protein functionality.

Certain embodiments of the present disclosure provide a method of promoting healing of a wound in a subject, the method comprising administering to the subject an effective amount of an agent which inhibits 14-3-3 protein functionality, thereby promoting healing of the wound in the subject.

In certain embodiments, the agent which modulates 14-3-3 protein functionality comprises a drug, a small molecule, a protein, a polypeptide, a lipid, a carbohydrate, a nucleic acid, a DNA, a RNA, an oligonucleotide, a ribozyme, a biologic, an aptamer, a peptide, a cofactor, a ligand, a ligand mimetic, a receptor, an enzyme, a kinase, a phosphatase, a signalling molecule, a cytokine, a growth factor, a metal ion, a chelate, an antisense nucleic acid, a siRNA, a microRNA, an antibody, and an amino acid. Other types of molecules are contemplated.

In certain embodiments, the agent does not comprise a phosphorylatable group. In certain embodiments, the agent does not comprise a hydroxyl group.

The term "nucleic acid" as used herein refers to an oligonucleotide or a polynucleotide and includes for example DNA, RNA, DNA/RNA, a variant or DNA and/or RNA (for example a variant of the sugar-phosphate backbone and/or a variant of one or more bases, such as methylation), and may be single stranded, double stranded, non-methylated, methylated or other forms thereof. In certain embodiments, the nucleic acid is a non-naturally occurring nucleic acid, a naturally occurring nucleic acid, a nucleic acid of genomic origin, a mitochondrial nucleic acid, a nucleic acid of cDNA origin (derived from a mRNA), a nucleic acid derived from a virus, a nucleic acid of synthetic origin, a single stranded DNA, a double stranded DNA, an analogue of DNA and/or RNA, and/or a derivative, fragment and/or combination of any of the aforementioned. Examples of derivatives also include nucleic acids that have a blocking group at the 5' and/or 3' ends for example to improve stability, and/or nucleic acids fused to other molecules. Other types of nucleic acids are contemplated. Methods for producing nucleic acids are known and include for example nucleic acids produced by recombinant DNA technology or nucleic acids produced by chemical synthesis. Methods for use of nucleic acids to express proteins or polypeptides are known in the art.

In certain embodiments, the agent is an antisense nucleic acid, such as an antisense RNA. In certain embodiments, the agent is a small interfering RNA. In certain embodiments, the agent is a microRNA. Methods for producing and delivering antisense nucleic acids, microRNAs and siRNAs are known. For example, therapeutic nucleic acids for treating cancer are described in "Nucleic Acid Therapeutics in Cancer" 2004 ed. Alan M. Gewirtz, Humana Press Inc.

In certain embodiments, the agent inhibits 14-3-3 protein functionality. In certain embodiments, the inhibiting of 14-3-3 functionality comprises exposing the subject to an agent that inhibits 14-3-3 functionality.

In certain embodiments, the agent comprises a selective inhibitor. In certain embodiments, the agent comprises a non-selective inhibitor.

In certain embodiments, the agent inhibits dimerization of a 14-3-3 protein.

In certain embodiments, the agent promotes phosphorylation of a 14-3-3 protein.

In certain embodiments, the agent which inhibits dimerization of the 14-3-3 protein comprises a cationic lipid. In certain embodiments, the agent comprises a cationic lipid.

In certain embodiments, the agent which inhibits dimerization of the 14-3-3 protein comprises a cationic lipid comprising a heterocyclic head group. Methods of synthesizing such compounds are known in the art.

In certain embodiments, the heterocyclic group comprises a three membered ring, a four membered ring, a five membered ring or a six membered ring. Other ring sizes are contemplated. In certain embodiments, the heterocyclic group comprises one heteroatom or two heteroatoms. Examples of heteroatoms comprise one or more of nitrogen, oxygen or sulphur. In certain embodiments, the heterocyclic group is a non-aromatic heterocyclic group. In certain embodiments, the heterocyclic group is an aromatic heterocyclic group.

In certain embodiments, the heterocyclic group comprises a heterocyclic ring selected from aziridine, oxirane, thiirane, azirine, oxirene, thiirene, azetidine, oxetane, thietane, azete, oxete, thiete, pyrrolidine, oxolane, thiolane, pyrrole, furan, thiophene, piperidine, oxane, thiane, pyridine, pyran, thiopyran and/or an optionally substituted form thereof. Other types of heterocyclic groups are contemplated.

In certain embodiments, the heterocyclic head group comprises a pyrrolidine group or a piperidine group.

In certain embodiments, the heterocyclic head group is a cationic head group. In certain embodiments, the heterocyclic head group comprises a quaternary amine group. In certain embodiments, the head group comprises a quaternary heterocyclic amine.

In certain embodiments, the head group comprises a quaternary pyrrolidine group or a quaternary piperidine group. In certain embodiments, the quaternary pyrrolidine group comprises a N,N-alkyl pyrrolidine. In certain embodiments, the quaternary pyrrolidine group comprises a N,N-methyl pyrrolidine. In certain embodiments, the quaternary piperidine group comprises a N,N-alkyl piperidine. In certain embodiments, the quaternary piperidine group comprises N,N-methyl piperidine.

In certain embodiments, the agent which inhibits dimerization of the 14-3-3 protein comprises a hydrophobic tail group of at least 12 carbon atoms. In certain embodiments, the cationic lipid comprises a heterocyclic head group and a hydrophobic tail group of at least 12 carbon atoms.

In certain embodiments, the hydrophobic tail group comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, the agent which inhibits dimerization of the 14-3-3 protein comprises a hydrophobic tail group of 12 to 20 carbon atoms.

In certain embodiments, the hydrophobic tail comprises 12 to 20 carbon atoms. 13 to 20 carbon atoms, 14 to 20 carbon atoms, 15 to 20 carbon atoms, 16 to 20 carbon atoms. 17 to 20 carbon atoms, 18 to 20 carbon atoms, 19 to 20 carbon atoms, 12 to 19 carbon atoms, 13 to 19 carbon atoms, 14 to 19 carbon atoms, 15 to 18 carbon atoms, 16 to 19 carbon atoms, 17 to 19 carbon atoms, 18 to 19 carbon atoms, 12 to 18 carbon atoms. 13 to 18 carbon atoms, 14 to 18 carbon atoms, 15 to 18 carbon atoms, 16 to 18 carbon atoms, 17 to 18 carbon atoms, 12 to 17 carbon atoms, 13 to 17 carbon atoms, 14 to 17 carbon atoms, 15 to 17 carbon atoms, 16 to 17 carbon atoms, 12 to 16 carbon atoms. 13 to 16 carbon atoms, 14 to 16 carbon atoms, 15 to 16 carbon atoms, 12 to 15 carbon atoms, 13 to 15 carbon atoms, 14 to 15 carbon atoms, 12 to 14 carbon atoms, 13 to 14 carbon atoms. or 12 to 13 carbon atoms.

In certain embodiments, the hydrophobic tail group comprises a octylphenyl)alkyl group and/or a substituted derivative thereof. In certain embodiments, the hydrophobic tail group comprises a (octylphenyl)ethyl group and or a substituted derivative thereof.

In certain embodiments, the hydrophobic tail group comprises a 2-(4-octylphenyl)ethyl group and/or a substituted derivative thereof.

In certain embodiments, the agent which inhibits dimerization of the 14-3-3 protein comprises a cationic lipid comprising a heterocyclic head group and a hydrophobic tail group of at least 12 carbon atoms.

In certain embodiments, the agent comprises a cyclic compound of formula I:

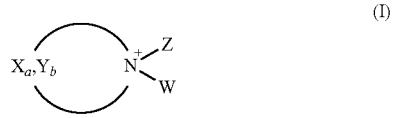

(I)

wherein;

$a+b \geq 3$;

X and Y are each independently, and in any combination or order, one of C, CH, $CH_2$, $CHR^1$, $CR^1R^2$, C=O, CH=O, $CR^1$=O, CHOH, $CR^1OH$, $CHOR^1$, $C(OR^1)(OR^2)$, S, N, O, NH, $NH^+$, $NR^1$ or $N(R^1)^+$, and $R^1$ and $R^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or $R^1$ and $R^2$ form part of a cyclic or heterocyclic group;

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods for synthesing such compounds of formula I are known in the art.

In certain embodiments, the cyclic group comprises an aziridine group, an azirine group, an azetidine group, an azete group, a pyrrolidine group, a pyrrole group, a piperidine, or a pyridine group.

In certain embodiments, $a+b \geq 4$. In certain embodiments, $a+b=3$, 4 5, 6 or 7. In certain embodiments, a=0 and $b \geq 3$. In certain embodiments, b=0 and $a \geq 3$.

In certain embodiments, a+b=5 or 6, that is the cyclic group is a five membered ring or a six membered ring.

In certain embodiments, the cyclic group comprises one or more heteroatoms in addition to the quaternary nitrogen. Examples of heteroatoms comprise one or more of nitrogen, oxygen or sulphur.

In certain embodiments, the cyclic group is a non-aromatic cyclic group. In certain embodiments, the cyclic group is an aromatic cyclic group.

In certain embodiments, the cyclic group comprises two or more cyclic groups.

In certain embodiments, W comprises an alkyl group and/or a substituted derivative thereof. In certain embodiments, W comprises a methyl group, and/or a substituted derivative thereof In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms. In certain embodiments, Z comprises 12 to 20 carbon atoms, 13 to 20 carbon atoms, 14 to 20 carbon atoms, 15 to 20 carbon atoms, 16 to 20 carbon atoms, 17 to 20 carbon atoms, 18 to 20 carbon atoms, 19 to 20 carbon atoms, 12 to 19 carbon atoms, 13 to 19 carbon atoms, 14 to 19 carbon atoms, 15 to 19 carbon atoms, 16 to 19 carbon atoms, 17 to 19 carbon atoms, 18 to 19 carbon atoms, 12 to 18 carbon atoms, 13 to 18 carbon atoms, 14 to 18 carbon atoms, 15 to 18 carbon atoms, 16 to 18 carbon atoms, 17 to 18 carbon atoms, 12 to 17 carbon atoms, 13 to 17 carbon atoms, 14 to 17 carbon atoms, 15 to 17 carbon atoms, 16 to 17 carbon atoms, 12 to 16 carbon atoms, 13 to 16 carbon atoms, 14 to 16 carbon atoms, 15 to 16 carbon atoms, 12 to 15 carbon atoms, 13 to 15 carbon atoms, 14 to 15 carbon atoms, 12 to 14 carbon atoms, 13 to 14 carbon atoms, or 12 to 13 carbon atoms.

In certain embodiments, Z comprises an octylphenyl group and/or a substituted derivative thereof. In certain embodiments, Z comprises an (octylphenyl)alkyl group, and/or a substituted derivative thereof. In certain embodiments, Z comprises an (octylphenyl)ethyl group and/or a substituted derivative thereof.

In certain embodiments, Z comprises a 2-(4-octylphenyl) ethyl group and/or a substituted derivative thereof In certain embodiments, the agent comprises a compound of the following formula:

(II)

wherein,
W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods of synthesizing compounds of formula II are known in the art.

W groups are as described herein. In certain embodiments, W comprises an alkyl group and/or a substituted derivative thereof. In certain embodiments, W comprises a methyl group and/or a substituted derivative thereof.

Z groups are as described herein. In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms.

In certain embodiments, Z comprises a 2-(4-octylphenyl)ethyl group and/or a substituted derivative thereof.

In certain embodiments, the agent comprises a compound of the following formula:

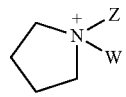

(III)

wherein,

W is H, optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Methods of synthesizing compounds of formula III are known in the art.

W groups are as described herein. In certain embodiments, W comprises an alkyl group or a substituted derivative thereof. In certain embodiments, W comprises a methyl group or a substituted derivative thereof.

Z groups are as described herein. In certain embodiments, Z comprises a group comprising at least 12 carbon atoms.

In certain embodiments, Z comprises at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, or at least 20 carbon atoms.

In certain embodiments, Z comprises a group of 12 to 20 carbon atoms.

In certain embodiments, Z comprises a 2-(4-octylphenyl)ethyl group.

In certain embodiments, the agent does not comprise a phosphorylatable group.

In certain embodiments, the agent does not comprise a hydroxyl group.

In certain embodiments, the agent does not have substantial immunosuppressant activity.

In certain embodiments, the agent comprises a compound of the following formula IV:

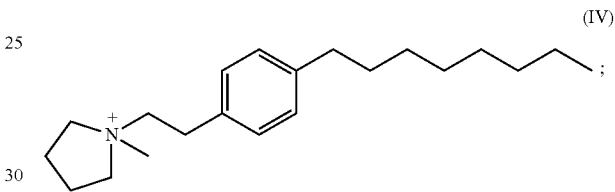

RB-011

(IV)

and/or a pharmaceutically acceptable salt or solvate thereof. Synthesis of a compound of formula IV may be achieved by a method known in the art, for example as described in D. J. Baek et al. (2013) Chem. Commun. (Camb). 49(21):2136-8. doi: 10.1039/c3cc00181d.

In certain embodiments, the agent comprises a compound of the following formula V:

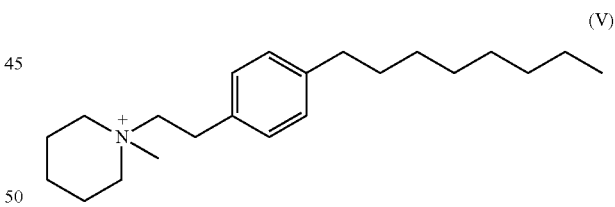

RB-012

(V)

and/or a pharmaceutically acceptable salt or solvate thereof. Synthesis of a compound of formula V may be achieved by a method known in the art, for example as described in D. J. Baek et al. (2013) Chem. Commun. (Camb). 49(21):2136-8. doi: 10.1039/c3cc00181d.

In certain embodiments, the agent comprises an antibody and/or an antigen binding fragment thereof.

The term "antibody" is to be understood to mean an immunoglobulin molecule with the ability to bind an antigenic region of another molecule, and includes monoclonal antibodies, polyclonal antibodies, multivalent antibodies, chimeric antibodies, multispecific antibodies, diabodies and fragments of an immunoglobulin molecule or combinations thereof that have the ability to bind to the antigenic region of another molecule with the desired affinity including a Fab, Fab', F(ab')2, Fv, a single-chain antibody (scFv) or a polypeptide that contains at least a portion of an immunoglobulin (or a variant of an immunoglobulin) that is sufficient to confer specific antigen binding, such as a molecule including one or more CDRs.

In this regard, an immunoglobulin is a tetrameric molecule, each tetramer being composed of two identical pairs of polypeptide chains, each pair having one light chain and one heavy chain. The amino-terminal portion of each chain includes a variable region of about 100 to 110 or more amino acids that is primarily responsible for antigen recognition. The carboxy-terminal portion of each chain defines a constant region primarily responsible for effector function. Human light chains are classified as κ and λ light chains. Heavy chains are classified as μ, Δ, γ, α, or ε and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site, with the result that an intact immunoglobulin has two binding sites. The variable regions further include hypervariable regions that are directly involved in formation of the antigen binding site. These hypervariable regions are usually referred to as Complementarity Determining Regions (CDR). The intervening segments are referred to as Framework Regions (FR). In both light and heavy chains there are three CDRs (CDR-I to CDR-3) and four FRs (FR-I to FR-4).

In certain embodiments, the agent comprises a neutralising antibody. In certain embodiments, the agent comprises an antagonist antibody. In certain embodiments, the agent comprises an antibody that inhibits dimerization of a 14-3-3 protein.

In certain embodiments, the antigen-binding fragment comprises a Fab, Fab', F(ab')2, Fd, Fv, a single-chain antibody (scFv), a chimeric antibody, a diabody or a polypeptide that contains at least a portion of an immunoglobulin that is sufficient to confer specific antigen binding.

A Fab fragment is a monovalent fragment consisting of the VL, VH, CL and CH I domains. A F(ab')$_2$ fragment is a bivalent fragment including two Fab fragments linked by a disulphide bridge at the hinge region. A Fd fragment consists of the VH and CH I domains. A Fv fragment consists of the VL and VH domains of a single arm of an antibody. A dAb consists of a VH domain. A single chain antibody (scFv) is an antibody in which VL and VH regions are paired to form a monovalent molecule via a synthetic linker that enable them to be made as a single protein chain. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

Antibody fragments that contain specific binding sites may be generated by a known method. Methods for producing antigen-binding fragments or portions of antibodies are known in the art, for example as described in "Antibody Engineering: Methods and Protocols" (2004) ed. by B. K. C. Lo Humana Press, herein incorporated by reference; and "Antibody Engineering: A Practical Approach" (1996) ed. by J. McCafferty, H. R. Hoogenboom and D J. Chriswell Oxford University Press, herein incorporated by reference. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries may be constructed to allow rapid and easy identification of monoclonal Fab fragments with the desired specificity, as described for example in Huse, W. D. et al. (1989) Science 254: 1275-1281, herein incorporated by reference.

Antibodies may be generated using known methods. For the production of antibodies, various hosts including goats, rabbits, rats, mice, humans, and others, may be immunized by injection with an appropriate antigen. Depending on the host species, various adjuvants may be used to increase an immunological response.

In certain embodiments, the antibody is a polyclonal antibody. A polyclonal antibody is a mixture of antibodies having different antigen specificities. Methods for producing and isolating polyclonal antibodies are known. In general, polyclonal antibodies are produced from B-lymphocytes. Typically polyclonal antibodies are obtained directly from an immunized subject, such as an immunized animal.

In certain embodiments, the antibody is a monoclonal antibody. Monoclonal antibodies may be prepared using a technique that provides for the production of antibody molecules by continuous isolated cells in culture. These include, but are not limited to, the hybridoma technique, the human B-cell hybridoma technique, and the EBV-hybridoma technique. Methods for the preparation of monoclonal antibodies include for example Kohler et al. (1975) Nature 256:495-497, herein incorporated by reference; Kozbor et al. (1985) J. Immunol. Methods 81:31-42, herein incorporated by reference; Cote et al. (1983) Proc. Natl. Acad. ScL 80:2026-2030, herein incorporated by reference; and Cole et al. (1984) Mol. Cell Biol. 62: 109-120, herein incorporated by reference.

In certain embodiments, the antibody and/or an antigen binding fragment thereof comprises an isolated antibody. Methods for producing and isolating polyclonal and monoclonal antibodies are known.

In certain embodiments, the antibody has an isotype selected from the group consisting of IgG1, IgG2a, IgG2b, IgG3, IgM and IgA.

In certain embodiments, the antibody and/or an antigen binding fragment thereof is a mouse antibody and/or an antigen binding fragment thereof, a human antibody and/or an antigen binding fragment thereof, or a humanized antibody and/or an antigen binding fragment thereof.

Humanized antibodies, or antibodies adapted for non-rejection by other mammals, may be produced by a suitable method known in the art, including for example resurfacing or CDR grafting. In resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host are known, for example as described in U.S. Pat. No. 5,639,641. Humanized forms of the antibodies may also be made by CDR grafting, by substituting the complementarity determining regions of, for example, a mouse antibody, into a human framework domain.

Methods for humanizing antibodies are known. For example, the antibody may be generated as described in U.S. Pat. No. 6,180,370, herein incorporated by reference; WO 92/22653, herein incorporated by reference; Wright et al. (1992) Critical Rev. in Immunol. 12(3,4): 125-168, herein incorporated by reference; and Gu et al. (1997) Thrombosis and Hematocyst 77(4):755-759), herein incorporated by reference.

Humanized antibodies typically have constant regions and variable regions other than the complementarity determining regions (CDRs) derived substantially or exclusively from a human antibody and CDRs derived substantially or exclusively from the non-human antibody of interest.

Techniques developed for the production of "chimeric antibodies", for example the splicing of mouse antibody genes to human antibody genes to obtain a molecule with appropriate antigen specificity and biological activity, may be performed by a suitable method. For example, chimeric antibodies may be produced as described in Morrison, S. L. et al. (1984) Proc. Natl. Acad. Sci 81:6851-6855; Neuberger, M. S. et al. (1984) Nature 312:604-608; and Takeda, S. et al. (1985) Nature 314:452-454.

Immunoassays may be used for screening to identify antibodies and/or antigen binding fragments thereof having the desired specificity.

Antibody molecules and antigen binding fragments thereof may also be produced recombinantly by methods known in the art, for example by expression in *E. coli* expression systems. For example, a method for the production of recombinant antibodies is as described in U.S. Pat. No. 4,816,567, herein incorporated by reference. Antigen binding fragments may also be produced by phage display technologies or using peptide libraries, which are known.

Methods for formulating and administering antibodies, and/or antigen binding fragments, are known in the art and include for example "Handbook of Therapeutic Antibodies" ed. S. Dubel (2007) Wiley-VCH.

In certain embodiments, the administration of an agent as described herein to a subject utilises a therapeutically effective amount of the agent.

The term "therapeutically effective amount" as used herein refers to that amount of an agent that is sufficient to effect prevention and/or treatment, when administered to a subject. The therapeutically effective amount will vary depending upon a number of factors, including for example the specific activity of the agent being used, the type and severity of the wound being treated, the age, physical condition, existence of other disease states, and nutritional status of the subject. Examples of therapeutic amounts are as described herein.

The agent may be administered to the subject in a suitable form. In this regard, the terms "administering" includes administering the agent, or administering a prodrug of the agent, or a derivative that will form a therapeutically effective amount of the agent within the body of the subject. The terms include routes of administration that are systemic (e.g., via injection such as intravenous injection, orally in a tablet, pill, capsule, or other dosage form useful for systemic administration of pharmaceuticals), and topical (e.g., creams, solutions, and the like, including solutions such as mouthwashes, for topical oral administration). Examples of administration are as described herein.

In certain embodiments, the administration of the agent comprises topical administration. In certain embodiments, the administration of the agent comprises topical administration to the wound.

In certain embodiments, the amount of agent administered topically is in an amount ranging from one of the following selected ranges: 1 µg to 100 mg; 1 µg to 10 mg; 1 µg to 1 mg; 1 µg to 100 µg; 1 µg to 10 µg; 10 µg to 100 mg; 10 µg to 10 mg; 10 µg to 1 mg; 10 µg to 100 µg; 100 µg to 100 mg; 100 µg to 10 mg; 100 µg to 1 mg; 1 mg to 10 mg; and 10 mg to 100 mg. The dose and frequency of administration may be determined by one of skill in the art.

In certain embodiments, the topical administration comprises delivery of the agent by way of a gel, an ointment, a cream, a lotion, a foam, an emulsion, a suspension, a spray, an aerosol, a solution, a liquid, a powder, a semi-solid, a gel, a jelly, a suppository; a solid, an ointment, a paste, a tincture, a linament, a patch, or release from a bandage, gauze or dressing.

Powders typically utilize small particle sizes which have a large surface area per unit weight.

Aerosols are systems that depend on the power of compressed or liquefied gas to expel the contents from the container. The propellants are responsible for developing the proper pressure within the container, and expel the product when the valve is opened and aids in the atomization or foam production of the products. Typically aerosols utilize hydrocarbon (eg propane, butane, and isobutene) and compressed gases such as nitrogen, carbon dioxide, and nitrous oxide.

Plasters are products that are made of materials that adhere to the skin and intended to bring an agent into close contact with the skin. Plasters having therapeutic agents provide a form of transdermal delivery of the agent.

Lotions are typically clear/semi-clear solutions. Lotions typically contain 25-50% alcohol and may also contain an antiseptic, an emollient, and a haemostypic substance. They may also contain one or more of extract of witchhazel, menthol, glycerin, boric acid, alum, potassium oxyquinoline sulphate and chloroform.

Liniments typically have a similar composition to lotions but are rubbed when applied.

Solutions are liquid preparations of soluble chemicals dissolved in solvents such as water, alcohol, or propylene glycol.

Ointments are semi-solid preparation intended for external application, which are often based on petrolatum. An ointment typically does not contain sufficient water to separate into a second phase at room temperature. Water-soluble ointments may be formulated for example with polyethylene glycol.

Ointment bases include hydrocarbon bases, absorption bases, water-removable bases, and water-soluble bases.

Hydrocarbon bases include Petrolatum USP, White petrolatum USP, Yellow petrolatum, USP, White petrolatum, USP. Absorption bases include those that permit the incorporation of aqueous solutions resulting in the formation of water-in-oil emulsions such as Hydrophilic Petrolatum and those that are water-in-oil emulsions (syn: emulsion bases) and permit the incorporation of additional quantities of aqueous solutions, such as Lanolin. Water-removable Bases are oil-in-water emulsions resembling creams in appearance and include Hydrophilic Ointment, USP. Water-soluble bases do not contain oleaginous components and include Polyethylene Glycol Ointment, NF.

Creams are medicaments dissolved or suspended in water removable or emollient bases. Creams are typically classified as water-in-oil or oil-in-water. Examples of cream bases include (i) an oleaginous phase including Spermaceti (eg 12.5%), White wax (eg 12.0%), Almond oil (eg 55.6%) and an aqueous phase including Sodium borate (eg 0.5%) and Purified water, USP (eg 16.5%); (ii) an Oleaginous phase including Steryl alcohol (eg 15%), beeswax (eg 8%) Sorbitan monooleate (eg 1.25%) and an aqueous phase including Sorbitol solution, 70% USP (eg 7.5%), Polysorbate 80 (eg 3.75%), Methyl paraben (eg 0.025%) Purified water, qs (eg 100%); (iii) an Oleaginous phase including Stearic acid (eg 13%), Stearyl alcohol (eg 1%), Cetyl alcohol (eg 1%) and an aqueous phase including Glycerin (eg 10%), Methyl paraben (eg 0.1%), Propyl paraben (eg 0.05%), Potassium hydroxide (eg 0.9%) Purified water, qs 100%.

Pastes are ointments into which a high percentage of insoluble solids have been added, typically up to 50% by weight. Ingredients such as starch, zinc oxide, calcium carbonate, and talc are used as the solid phase.

Gels are semisolid systems made up of dispersions of small or large molecules in an aqueous liquid vehicle rendering jelly-like through the addition of gelling agent. Gelling agents include synthetic macromolecules such as Carbomer 934, Cellulose derivatives auch as Carboxymethylcellulose and Hydroxypropylmethyl-cellulose.

Jellies are water-soluble bases prepared from natural gums such as tragacanth, pectin, alginate, and boroglycerin or from synthetic derivatives of natural substances such as methylcellulose and carboxymethylcellulose.

Emulsions are two-phase preparations in which one phase (the dispersed or internal phase) is finely dispersed in the other (continuous or external phase). The dispersed phase can have either a hydrophobic-based (oil-in-water), or be aqueous based (water-in-oil). Because there are two incompatible phases in close conjunction, the physical stabilizing system. Typically, the stabilizing system comprises surfactant (ionic or nonionic), polymers (nonionic polymers, polyelectrolytes, or biopolymers), or mixtures of these. Emulsions include Water-in-oil emulsion, Oil-in-water emulsion, Water-in-oil-in-water emulsion and Oil-in-water-in-oil emulsions.

Hydrophobic vehicles for topical administration include such as liquid petrolatum (mineral oil, liquid paraffin, paraffin oil), white petrolatum (petroleum jelly, vaseline), yellow petrolatum (petroleum jelly), squalane (perhydrosqualene, spinacane), silicones such as liquid polydimethylsiloxanes (dimethicone, silastic, medical grade silicone oil), alcohols such as lauryl alcohols (1-dodecanol, dodecyl alcohols), myristyl alcohols (tetradecanol, tetradecyl alcohols), cetyl alcohols (hexadecanol, ethal, palmityl alcohols), stearyl alcohols (stenol, cetosteryl alcohols), oleyl alcohols (ocenol), sterols; sterol esters Lanolin (hydrous wool fat, lanum), anhydrous lanolin (wool fat, anhydrous lanum, agnin), semi synthetic lanolin, carboxylic acids such as lauric acid, myristic acid, palmitic acid, stearic acid, oleic acid, esters, polyesters, cholesterol esters (stearate), ethylene glycol monoesters, propylene glycol monoesters, glyceryl monoesters, glyceryl monostearate, sorbitol monoesters, sorbitain monoesters, sorbitol diesters, sorbitan polyesters (spans, arlacels), glyceryl tristearate, lard, almond oil, corn oil, caster oil, cottonseed oil, olive oil, soyabean oil, hydrogenated oils, sulfated oils, isopropyl myristate, isopropyl palmitate, ethers; polyethers polyethylene-polypropylene glycols (pluronics).

Water-miscible vehicles include polyols; polyglycols, propylene glycol (1,2-propanediol), glycerin (glycerol), liquid polyethylene glycol, solid polyethylene glycol (hard macrogol, carbowax), 1,2, Phenols-hexanetriol, sorbitol solution 70%, esters; polyesters, polyoxyethylene sorbitain monoesters (stearate-tweens), polyoxy ethylene sorbitan polyesters (tweens), ethers, polyethers, polyethylene glycol monocetyl ether (cetomacrogol 1000), polyethylene-polypropylene glycols (pluronics)

Structural matrix formers including hydrocarbons, white petrolatum (petroleum jelly, vaseline), yellow petrolatum (petroleum jelly), paraffin (paraffin wax, hard paraffin), microcrystalline wax, ceresin (mineral wax, purified ozokerite), silicones, fumed silica (cab-O-sil), bentonite (colloidal aluminum silicate), veegum (colloidal magnesium aluminum silicate), polyols, polyglycols, solid polyethylene glycol (hard macrogol, carbowax), alcohols, cetyl alcohols (hexadecanol, ethal, palmityl alcohols), stearyl alcohols (stenol, cetosteryl alcohols), sterols sterol esters, cholesterol (cholesterin), lanolin (hydrous wool fat, lanum), anhydrous lanolin (wool fat, anhydrous lanum, agnin), semi synthetic lanolin, carboxylic acids, lauric acid, myristic acid, palmitic acid, stearic acid, oleic acid, esters, polyesters, bees wax, white bees wax (bleached bees wax), carnauba wax, myricin, cholesterol esters (stearate), polyoxyethylene sorbitain, monoesters (stearate-tweens), lard, hydrogenated oils.

Suspending, jelling, or viscosity inducing agents include silicones, fumed silica (cab-O-sil), bentonite (colloidal aluminium silicate), veegum (colloidal magnesium aluminium silicate), polycarboxylates; polysulfates; polysaccharides, aAgar, alginates, carragen, acacia, tragacanth, methylcellulose, carboxy methylcellulose, hydroxy ethyl cellulose, carboxy vinyl polymer, gelatin, pectin, xanthan, polyacrylic acid.

Water-in-oil emulsifiers include sterols, sterol esters, cholesterol (cholesterin) lanolin (hydrous wool fat, lanum), anhydrous lanolin (wool fat, anhydrous lanum, agnin), semi synthetic lanolin, carboxylic acids, $Na^+$, $K^+$ ethanolamin salts of lauric acid, myristic acid, palmitic acid, stearic acid, oleic acid, ethers, polyethers, polyethylene-polypropylene glycols (pluronics). Oil-in-water (o/w) emulsifier include esters, polyesters, polyoxyethylene sorbitain monoesters (stearate-tweens), polyoxy ethylene esters (stearate-polyethylene glycol monoesters, Myrj), olyoxy ethylene sorbitan polyesters (tweens), ethers, polyethers, polyethylene glycol monocetyl ether (cetomacrogol 1000), and polyethylene-polypropylene glycols (pluronics).

Antimicrobials includes benzalkonium chloride, benzoic acid, benzyl alcohol, bronopol, chlorhexidine, chlorocresol, imidazolidinyl urea, paraben esters, phenol, phenoxyethanol, potassium sorbate, sorbic acid. Antioxidants include a-Tocopherol, ascorbic acid, ascorbyl palmitate, butylated hydroxyanisole, sodium ascorbate, sodium metabisulfite. Chelating agents include citric acid and edetic acid.

Buffers include citric acid and salts, phosphoric acid and salts, $H_3PO_4/NaH_2PO_4$, glycine, acetic acid, triethanolamine and boric acid.

Humectants include glycerin (glycerol), propylene glycol (E 1520), glyceryl triacetate (E1518), sorbitol (E420), xylitol and maltitol (E965), polydextrose (E1200), quillaia (E999), lactic acid, urea, and lithium chloride.

In certain embodiments, the agent is administered to the subject to produce a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater.

In certain embodiments, the agent is administered to the subject in an amount ranging from one of the following selected ranges: 1 μg/kg to 100 mg/kg; 1 μg/kg to 10 mg/kg; 1 μg/kg to 1 mg/kg; 1 μg/kg to 100 μg/kg; 1 μg/kg to 10 μg/kg; 10 μg/kg to 100 mg/kg; 10 μg/kg to 10 mg/kg; 10 μg/kg to 1 mg/kg; 10 μg/kg to 100 μg/kg; 100 μg/kg to 100 mg/kg; 100 μg/kg to 10 mg/kg; 100 μg/kg to 1 mg/kg; 1 mg/kg to 10 mg/kg; and 10 mg/kg to 100 mg/kg body weight. The dose and frequency of administration may be determined by one of skill in the art.

In certain embodiments, the agent is administered orally. In certain embodiments, the agent is administered intravenously. In certain embodiments, the agent is administered via injection such as intravenous injection. In certain embodiments, the agent is administered by nebulized administration, by aerosolized administration or by being instilled into the lung.

The agent may be administered alone or may be delivered in a mixture with other therapeutic compounds and/or compounds that enhance, stabilise or maintain the activity of the agent.

In certain embodiments, the administration comprises administration of an anti-bacterial agent.

In certain embodiments, an administration vehicle is utilised such as pill, a tablet, an implant, an injectable solution and would contain both the agent and additional compound(s).

The method may also include combination therapy. In this regard, the subject is treated or given another drug or treatment modality in conjunction with the agent as described herein. This combination therapy can be sequential therapy where the subject is treated first with one and then the other, or the two or more treatment modalities are given simultaneously.

When administered to a subject the therapeutically effective dosage may vary depending upon the particular agent utilized, the mode of administration, the condition, and severity thereof, as well as the various physical factors related to the subject being treated. As discussed herein, suitable daily doses range from 1 μg/kg to 100 mg/kg. The daily dosages are expected to vary with route of administration, and the nature of the agent administered. In certain embodiments the methods comprise administering to the subject escalating doses of agent and/or repeated doses. In certain embodiments, the agent is administered orally. In certain embodiments, the agent is administered via injection, such as intravenous injection. In certain embodiments, the agent is administered parenterally. In certain embodiments, the agent is administered by direct introduction to the lungs, such as by aerosol administration, by nebulized administration, and by being instilled into the lung. In certain embodiments, the agent is administered by implant. In certain embodiments, the agent is administered by subcutaneous injection, intraarticularly, rectally, intranasally, intraocularly, vaginally, or transdermally. In certain embodiments, the agent is administered by ex vivo treatment of the relevant cells, tissue or organ, followed by reintroduction into the subject.

Certain embodiments of the present disclosure provide a method of modulating epithelialization of a wound.

In certain embodiments, the epithelialization is promoted. In certain embodiments, the epithelialization is promoted by inhibiting 14-3-3 functionality.

Certain embodiments of the present disclosure provide a method of promoting re-epithelialization of a wound in a subject, the method comprising administering to the subject an effective amount of an agent which inhibits 14-3-3 protein functionality, thereby promoting re-epithelialization of the wound in the subject.

Methods for assessing epithelialization are known in the art. Agents, and methods for administering agents, are as described herein.

Certain embodiments of the present disclosure provide a method of modulating cellular collagen production in a wound.

In certain embodiments, the cellular collagen production is promoted. In certain embodiments, the cellular collagen production is promoted by inhibiting 14-3-3 functionality.

Certain embodiments of the present disclosure provide a method of promoting cellular collagen production in a wound, the method comprising exposing the wound to an effective amount of an agent which inhibits 14-3-3 protein functionality, thereby promoting cellular collagen production in the wound. Examples of agents are as described herein.

Methods for assessing cellular collagen production are known in the art. Agents, and methods for administering agents, are as described herein.

Certain embodiments of the present disclosure provide a method for modulating remodelling of a wound.

In certain embodiments, the re-modelling is inhibited. In certain embodiments, the remodelling is inhibited by inhibiting 14-3-3 functionality.

Certain embodiments of the present disclosure provide a method of inhibiting remodelling of a wound, the method comprising exposing the wound to an effective amount of an agent which inhibits 14-3-3 protein functionality, thereby inhibiting re-modelling of the wound.

Methods for assessing cellular collagen production are known in the art. Agents, and methods for administering agents, are as described herein.

In certain embodiments, the agent as described herein may be used in a medicament or a therapeutic or pharmaceutical composition. In certain embodiments. the agent may be used in a medicament or a therapeutic or pharmaceutical composition for use in the methods of the present disclosure as described herein. Formulations are known and described in. for example. Remington's Pharmaceutical Sciences. 17th ed. Mack Publishing Company. Easton. Pa., 1985. which is incorporated herein by reference in its entirety.

Certain embodiments of the present disclosure provide use of an agent in the preparation of a medicament for modulating healing of a wound in a subject, wherein the agent modulates 14-3-3 protein functionality.

Certain embodiments of the present disclosure provide use of an agent in the preparation of a medicament for promoting healing of a wound in a subject. wherein the agent inhibits 14-3-3 protein functionality.

Examples of agents are as described herein.

In certain embodiments, the agent inhibits 14-3-3 protein dimerization.

In certain embodiments, the agent comprises a cationic lipid comprising a heterocyclic head group and a hydrophobic tail group of at least 12 carbon atoms.

In certain embodiments, the agent comprises a cyclic compound of formula I:

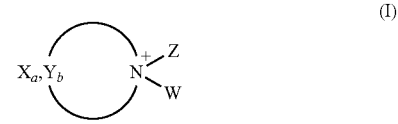

wherein;

$a+b \geq 3$;

X and Y are each independently, and in any combination or order. one of C, CH, $CH_2$, $CHR^1$, $CR^2R^2$, C=O, CH=O, $CR^1$=O, CHOH, $CR^1OH$, $CHOR^1$, $C(OR^1)(OR^2)$, S, O, N, NH, $NH^+$, $NR^1$ or $N(R^1)$, and $R^1$ and $R^2$ are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R¹ and R² form part of a cyclic or heterocyclic group:

W is H, optionally substituted alkyl, optionally substituted alkenyl, optionally substituted alkynyl, optionally substituted aryl, optionally substituted heteroalkyl. optionally substituted heterocycle, optionally substituted heteroaryl, optionally substituted alkoxy, optionally substituted aryloxy, optionally substituted heteroaryloxy. optionally substituted arylalkoxy, optionally substituted heteroarylalkoxy, or a combination of any of the aforementioned;

Z comprises at least 12 carbon atoms and is optionally substituted alkyl, optionally substituted alkenyl, optionally substituted alkynyl, optionally substituted aryl optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and or a pharmaceutically acceptable salt or solvate thereof.

In certain embodiments, the agent comprises a compound of the following formula IV:

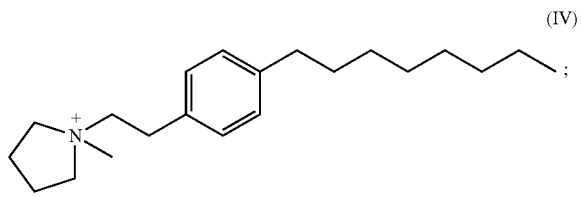

RB-011 and or a pharmaceutically acceptable salt or solvate thereof.

In certain embodiments, the agent comprises a compound of the following formula V;

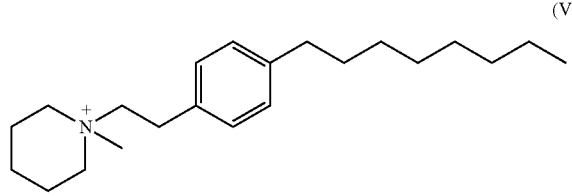

RB-012 and/or a pharmaceutically acceptable salt or solvate thereof.

Certain embodiments of the present disclosure provide a medicament or a composition comprising an agent as described herein.

Certain embodiments of the present disclosure provide a medicament or a composition comprising an agent which comprises a cationic lipid comprising a heterocyclic head group and a hydrophobic tail group of at least 12 carbon atoms.

Certain embodiments of the present disclosure provide a medicament or a composition comprising an agent which comprises a cyclic compound of formula I:

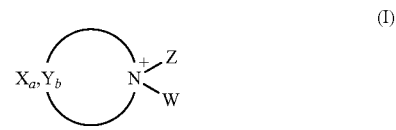

(I)

wherein;

$a+b\geq3$;

X and Y are each independently, and in any combination or order, one of C, CH, CH₂, CHR¹, CR¹R², C=O, CH=O, CR¹=O, CHOH, CR¹OH, CHOR¹, C(OR¹)(OR²), S, O, N, NH, NH⁺, NR¹ or N(R¹)⁺, and R¹ and R² are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R¹ and R² form part of a cyclic or heterocyclic group:

W is H, optionally substituted alkyl, optionally substituted alkenyl, optionally substituted alkynyl, optionally substituted aryl, optionally substituted heteroalkyl. optionally substituted heterocycle, optionally substituted heteroaryl, optionally substituted alkoxy, optionally substituted aryloxy, optionally substituted heteroaryloxy. optionally substituted arylalkoxy, optionally substituted heteroarylalkoxy, or a combination of any of the aforementioned:

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

Certain embodiments of the present disclosure provide a medicament or a composition comprising a compound of the following formula IV:

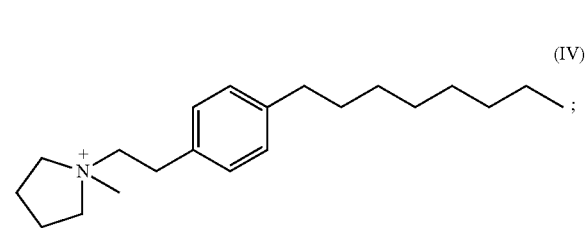

RB-011 and or a pharmaceutically acceptable salt or solvate thereof.

Certain embodiments of the present disclosure provide a medicament or a composition comprising an agent which comprises a compound of the following formula V:

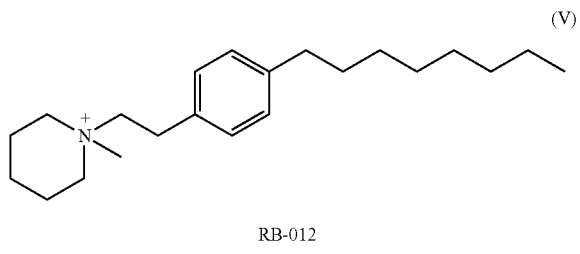

(V)

RB-012 and or a pharmaceutically acceptable salt or solvate thereof.

In certain embodiments, the composition comprises a wound healing composition.

Certain embodiments of the present disclosure provide a wound healing composition, the composition comprising in inhibitor of 14-3-3 protein functionality.

In certain embodiments, the agent is present in a medicament or a pharmaceutical composition so as to produce a concentration of the agent in the subject of 0.1 nM or greater, 0.5 nM or greater, 1 nM or greater, 5 nM or greater, 10 nM or greater, 50 nM or greater, 100 nM or greater, 500 nM or greater. 1 uM or greater, 5 uM or greater, 10 uM or greater, 100 uM or greater, 500 uM or greater, 1 mM or greater, or 10 mM or greater. Other concentrations are contemplated.

In certain embodiments, the agent in a medicament or a pharmaceutical is present so as to provide an amount of agent for administration to the subject in an amount ranging from one of the following selected ranges: 1 µg, kg to 100 mg/kg: 1 µg/kg to 10 mg/kg, 1 µg/kg to 1 mg/kg; 1 µg/kg to 100 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg; 1 mg/kg to 10 mg/kg; and 10 mg/kg to 100 mg/kg body weight. Other amounts are contemplated.

In certain embodiments, the medicament or pharmaceutical composition comprises an amount of the agent for administration from one of the following selected ranges: 1 µg to 1000 mg; 1 µg to 100 mg; 1 µg to 1 mg; 1 µg to 100 µg to 10 µg; 10 µg to 100 mg; 10 µg to 1000 mg; 10 µg, to 100 mg; 10 µg to 10 µg; 10 µg to 1 mg; 10 µg to 100 µg; 100 µg to 1000 mg; 100 µg to 100 mg; 100 µg to 10 mg; 100 µg to 1 mg; 1 mg to 1000 mg; 1 mg to 100 mg; 1 mg to 10 mg; 10 mg to 1000 mg; and 10 mg to 100 mg. Other amounts are contemplated.

In certain embodiments, the medicament or pharmaceutical composition is suitable for topical delivery to the subject. Topical formulations are as described herein.

Certain embodiments of the present disclosure provide a topical composition, the composition comprising a 14-3-3 inhibitor and a topically acceptable excipient.

Topically acceptable excipients are as described herein. 14-3-3 inhibitors are as described herein.

For example, a topical cream formulation may be prepared by mixing aqueous hypoallergenic sorbolene cream (cetomacrogel cream without glycerol) with an agent as described herein at a concentration of 10-1000 µg/ml and the cream may be applied daily to an open wound and the treatment continued for 8-10 days until wound healing is evident.

In certain embodiments, the medicament or composition is suitable for delivery to the subject by one or more of intravenous administration, intratracheal administration, by nebulized administration, by aerosolized administration, by instillation into the lung, by oral administration, by parenteral administration, by implant, by subcutaneous injection, intraarticularly, rectally, intranasally, intraocularly, vaginally, or transdermally.

In certain embodiments, the agent is provided in a pharmaceutically acceptable carrier suitable for administration. Carriers may be chosen based on the route of administration as described herein, the location of the target issue, the agent being delivered, the time course of delivery, etc. The term "pharmaceutically acceptable carrier" refers to a substantially inert solid, semi-solid or liquid filler, diluent, encapsulating material or formulation auxiliary of any type. An example of a pharmaceutically acceptable carrier is physiological saline. Other physiologically acceptable carriers and their formulations are known in the art. Some examples of materials which can serve as pharmaceutically acceptable carriers include, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminium hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present.

In certain embodiments, the agent may be administered or present in a medicament or a composition as a pharmaceutically acceptable salt. The term "pharmaceutically acceptable salt" refers to acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

In certain embodiments, the composition or medicament comprises other therapeutic compounds and/or compounds that enhance, stabilise or maintain the activity of the active.

Oral formulations for use containing an agent as described herein may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminium silicate, and triethanolamine. Oral formulations may utilize standard delay or time-release formulations to alter the absorption of the peptides. The oral formulation may also consist of administering the active ingredient in water or a fruit juice, containing appropriate solubilizers or emulsifiers as needed.

In certain embodiments, it may be desirable to administer the agent directly to the airways in the form of an aerosol. Formulations for the administration of aerosol forms are known.

In certain embodiments, it may be desirable to administer the agent parenterally (such as directly into the joint space) or intraperitoneally. For example, solutions or suspensions of these compounds in a non-ionised form or as a pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations typically contain a preservative to prevent the growth of microorganisms.

In certain embodiments, it may be desirable to administer the agent by injection. Pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol and liquid polyethylene glycol), suitable mixtures thereof, and vegetable oils.

In certain embodiments, it may be desirable to administer the agent intravenously. Compositions containing the agent described herein suitable for intravenous administration may be formulated by a skilled person.

In certain embodiments, it may be desirable to administer the agent transdermally. Transdermal administrations are understood to include all administrations across the surface of the body and the inner linings of bodily passages including epithelial and mucosal tissues. Such administrations may be carried out using the inhibitor as described herein, or pharmaceutically acceptable salts thereof, in lotions, creams, foams, patches, suspensions, solutions, and suppositories (rectal and vaginal).

Transdermal administration may also be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient.

In certain embodiments, it may be desirable to administer the agent by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

Additional numerous various excipients, dosage forms, dispersing agents and the like that are suitable for use in connection with the administration of the inhibitor and/or the formulation into medicaments or pharmaceutical compositions.

Formulations are known and described in, for example, Remington's Pharmaceutical Sciences, 17th ed., Mack Publishing Company, Easton, Pa., 1985, which is incorporated herein by reference in its entirety.

Certain embodiments of the present disclosure provide a method of promoting healing of a wound by administering to the subject an effective amount of an agent as described herein.

Certain embodiments of the present disclosure provide a method of promoting healing of a wound in a subject, the method comprising administering to the subject an effective amount of a composition or medicament as described herein.

Certain embodiments of the present disclosure provide a method of treating a subject suffering a wound, the method comprising administering to the subject an effective amount of composition or medicament as described herein.

Certain embodiments of the present disclosure provide a wound healing product, the product comprising a releasable 14-3-3 inhibitor. Examples of inhibitors of 14-3-3 are as described herein.

In certain embodiments, the product comprises a bandage or dressing. Methods for incorporating agents into products for topical release or transdermal administration are known in the art, for example as described in Boateng J. S. et al (2008) "Wound healing dressings and drug delivery systems: a review" J. Pharm Sci. 97(8): 2892-2923 and "Delivery System Handbook for Personal Care and Cosmetic Products: Technology" (2005) by Meyer Rosen, published William Andrew Inc, Norwich N.Y.

Certain embodiment of the present disclosure a bandage or dressing comprising a releasable 14-3-3 inhibitor.

Certain embodiments of the present disclosure provide a method of treating a wound in a subject, the method comprising, applying to the wound a topical composition as described herein. a wound healing product as described herein. or a bandage or dressing as described herein.

Certain embodiments of the present disclosure provide a method of modulating proliferation and/or migration of a cell associated with healing a wound, the method comprising exposing the cell to an agent as described herein.

Certain embodiments of the present disclosure provide a method of promoting proliferation and/or migration of a cell associated with healing a wound. the method comprising exposing the cell to an agent that inhibits 14-3-3 functionality.

Methods for proliferation and or migration of cells are known in the art. Examples of agents are as described herein.

In certain embodiments, the agent comprises a cationic lipid comprising a heterocyclic head group and a hydrophobic tail group of at least 12 carbon atoms.

In certain embodiments, the agent comprises a cyclic compound of formula I:

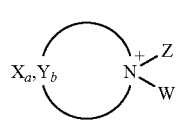

wherein, $a+b \geq 3$;

X and Y are each independently, and in any combination or order, one of C, CH, C H CHR¹, CR¹R², C, O, CH, O, CR¹, O, CHOH, CR¹OH, CHOR¹, C(OR¹)(OR²), S, O, N, NH, NH⁺, NR¹ or N(R¹)⁺, and R¹ and R² are each independently is an optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or R¹ and R² form part of a cyclic or heterocyclic group:

W is H optionally substituted alkyl, optionally substituted alkenyl, optionally substituted alkenyl, optionally substituted aryl, optionally substituted heteroalkyl. optionally substituted heterocycle, optionally substituted heteroaryl, optionally substituted alkoxy, optionally substituted aryloxy, optionally substituted heteroaryloxy. optionally substituted arylalkoxy, optionally substituted heteroarylalkoxy, or a combination of any of the aforementioned:

Z comprises at least 12 carbon atoms and is optionally substituted alkyl, optionally substituted alkenyl, optionally substituted alkynyl, optionally substituted aryl, optionally substituted heteroalkyl, optionally substituted heterocycle, optionally substituted heteroaryl, optionally substituted alkoxy, optionally substituted aryloxy, optionally substituted heteroaryloxy, optionally substituted arylalkoxy, optionally substituted heteroarylalkoxy, or any combination of the aforementioned; and/or a pharmaceutically acceptable salt or solvate thereof.

In certain embodiments, the went comprises a compound of the following formula IV:

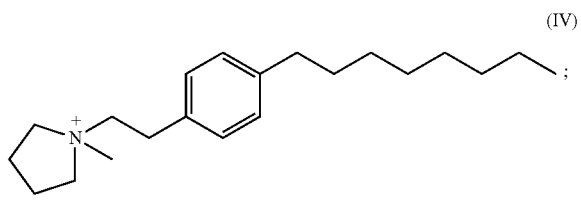

RB-011 and or a pharmaceutically acceptable salt or solvate thereof.

In certain embodiments, the agent comprises a compound of the following formula V:

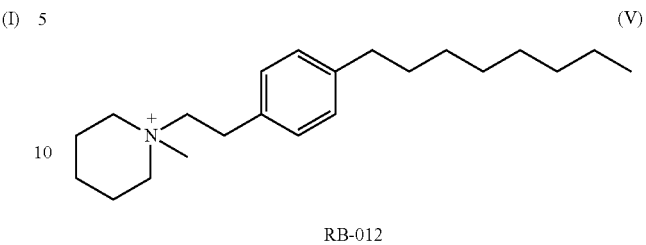

RB-012 and or a pharmaceutically acceptable salt or solvate thereof.

The term "exposing", and related terms such as "expose" and "exposure", refers to directly and or indirectly contacting and or treating a species (for example a cancerous cell) with the agent. The term "effective amount" as used herein refers to that amount of the agent that when exposed to a cell or another species is sufficient to illicit the desired response or outcome. The effective amount will vary depending upon a number of factors, including for example the specific activity of the agent being used and the cell type.

In certain embodiments, the cell comprises one or more cells associated with a wound.

In certain embodiments, the cell comprises a fibroblast cell.

In certain embodiments, the cell comprises one or more cells in vivo. For one or more cells in vivo, the agent may be administered to a subject to expose cells to the agent, or another compound may be administered to a subject that results in the production of the agent in the subject, thereby exposing cells in vivo to an inhibitor.

In certain embodiments, the cell comprises one or more cells ex vivo. For example, one or more cells may be removed from a subject and contacted directly or indirectly with the agent, and cells then introduced back into the same or another subject to effect exposure to the agent. For example a cancerous cell may exposed to an inhibitor ex vivo, and subsequently be introduced into a subject.

In certain embodiments, the cell comprises one or more cells in vitro. Cells in vitro include one or more isolated cells r one or more cells in culture. Other types of in vitro settings are contemplated.

In certain embodiments, a cell is exposed to a concentration of the agent of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. Other concentrations are contemplated.

In certain embodiments, the cell comprises one or more cells associated with a wound.

Certain embodiments of the present disclosure provide a method of identifying a wound healing agent.

Certain embodiments of the present disclosure provide a method of identifying a wound healing agent, the method comprising:

determining the ability of a candidate agent to inhibit 14-3-3 protein functionality; and identifying the candidate agent as a wound healing agent.

Such agents have therapeutic potential as described herein.

14-3-3 proteins are as described herein. In certain embodiments, the 14-3-3 protein comprises a 14-3-3ζ protein.

Certain embodiments of the present disclosure provide an agent identified using the methods as described herein.

Examples of test/candidate agents include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, an enzyme, a kinase, a phosphatase, a cytokine, a growth factor, a metal ion, a chelate, an antisense nucleic acid, an antisense RNA, a microRNA, a siRNA, an antibody or antigen binding part thereof. Other types of agents are contemplated.

Methods for determining the ability of a candidate/test agent to inhibit 14-3-3 protein functionality are known in the art. Such methods may utilise testing the agent in a suitable animal model.

Certain embodiments of the present disclosure provide a method of screening agents using a method as described herein.

Standard techniques may be used for recombinant DNA technology, oligonucleotide synthesis, antibody production, peptide synthesis, tissue culture and transfection. Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), herein incorporated by reference.

The present disclosure is further described by the following examples. It is to be understood that the following description is for the purpose of describing particular embodiments only and is not intended to be limiting with respect to the above description.

Example 1—Materials and Methods

Materials and Methods (i) Compounds

Trimethyl ammonium (TMA) compounds were purchased from Sigma. RB compounds were generated as mesylate salts; RB-011 and -012 were synthesized as described in D. J. Baek et al. (2013) Chem. Commun. (Camb). 49(21):2136-8. doi: 10.1039/c3cc00181d.

All compounds were dissolved in 100% ethanol and diluted into assay such that final ethanol concentration was 0.1% (v/v) or less. For studies with RB compounds, sodium mesylate was also added to vehicle treatment at the relevant concentration.

(ii) 14-3-3 Phosphorylation Assay

Substrate 14-3-3 (0.5 µg of purified recombinant 14-3-3) was added to 15 µl reaction mixture comprising 0.2 U of the PKA catalytic subunit, in the presence or absence of compounds (delivered in 0.1% v/v ethanol) in PKA reaction buffer (10 mM Tris-HCl pH 7.4, 15 mM $MgCl_2$, 3 mM DTT) containing 25 µM ATP and 0.3 µCi [$^{32}$P] 7-ATP). Reactions were incubated at 37° C. for 15 min. After incubation, reactions were separated on 12.5% SDS-PAGE, coomassie stained and 14-3-3 phosphorylation analysed by autoradiography.

(iii) Cell Lines and Culture

Jurkat cells were obtained from the ATCC and A549 cell lines from ECACC. Jurkat cells were routinely cultured in RPMI with 10% FBS and A549 cells in DMEM with 10% FBS at 37° C. with 5% $CO_2$ Jurkat Bcl-2 cells were generated by lentiviral transduction using a third generation lentiviral construct, as described previously (10) containing a Bcl-2α-IRES-IL2Rα encoding cassette. Transduced cells were FACS sorted for expression of IL2Rα using anti-CD25-PE (BD Pharmingen #555433) to enrich for Bcl-2 over-expressing cells and protein expression was further confirmed by immunoblotting with anti-Bcl-2 antibody (#610538; BD Transduction Laboratories, data not shown).

(iv) Apoptosis Assays; TMRE, Caspase 3 and Annexin V

Jurkat cells were routinely set up in apoptosis assays at $2 \times 10^5$/ml in RPMI with 0.5% FBS. After treatment, cells were stained either with 200 nM TMRE, 5 µl/ml NucView™ (Biotium), or Annexin V-FITC (Roche) for 15 mins prior to analysis by flow cytometry. Forward- and side-scatter properties were used to exclude debris and a 'viable' gate corresponding to the intact, PI negative cell population was used for fluorescence analysis. For A549, cells at 90% confluency were treated with RB compounds for 48 hrs in DMEM with 0.5% FBS. After treatment, cells were released with trypsin and then stained with NucView™ prior to analysis by flow cytometry.

(v) Assessment of A549 Cell Viability by MTS Assay

A549 cells (2500/well) were plated in 96 well trays in DMEM with 0.5% FBS and cultured at 37° C. with 5% $CO_2$ overnight. The following day RB compounds were added and cells incubated for a further 48 hours prior to removal of the medium and replacement with MTS reagent diluted 1:6 in Dulbecco's PBS. The cells were incubated at 37° C. for a further 4 hours and the conversion of MTS to the coloured formazan compound determined by measurement of absorbance at 490 nM.

(vi) A549 Colony Assay

A549 cells (7500) were plated in 0.33% low-melting point agarose in DMEM with 10% FBS with and without RB compounds over a 0.5% low-melting point agarose base. Cells were incubated at 37° C. with 5% $CO_2$ for 14 days and then colonies were photographed and analysed using Image J.

(vi) Immunoblotting

Jurkat cells were treated at $5 \times 10^5$/ml in RPMI with 0.5% FBS as detailed. Cells were harvested by centrifugation at 1500 g for 5 mins and washed with PBS prior to lysis in NP40 lysis buffer (10 mM Tris-HCl pH7.4, 137 mM NaCl, 10% glycerol, 1% NP40, protease inhibitor (Roche), 4 mM NaF, 2 mM Na-vanadate, 10 mM β-glycerophosphate, 1 mM Na-pyrophosphate, 1 mM Na-molybdate) for 30 minutes on ice with vortexing. The lysates were clarified at 13,000 rpm for 15 minutes at 4° C. and protein concentration determined using BCA assay (Pierce). 30-40 µg of lysate were run on to Criterion-XT 4-12% Bis-Tris gels (Bio-Rad), followed by transfer onto nitrocellulose. The filters were blocked for 30 minutes at room temperature in TNT buffer (10 mM Tris-HCl pH8, 150 mM NaCl, 0.05% Tween-20) containing blocking buffer (Roche), prior to incubation with antibodies over night. Antibodies used were from Cell Signalling; Phospho-p38 MAPK(#4571), Phospho-SAPK/JNK(81E11), Phospho-p44/42 MAP kinase (#9101), Phospho-AKT S473 (#9271), p44/42 MAP kinase (#9102), AKT (#9272), BID (#2002), caspase-3 (#9602), PARP (#9542), and Santa Cruz Biotechnology; pan 14-3-3 K19 (sc-629). Following antibody binding, filters were washed in TNT for 1 hr at room temperature, incubated with 1/12,500 anti-rabbit or anti-mouse HRP secondary antibody (Pierce) for 1 hr at room temperature and finally washed for 1 hr with TNT before incubation with Clarity western ECL reagent (Bio-Rad). Filters were exposed on a LAS 4000 imager. Blots were analysed using Multi-gauge/Colony software FUJI FILM).

(vii) Xenograft Studies

All experimental procedures involving animals were conducted in accordance with the NHMRC Australian Code for the Care and Use of Animals for Scientific Purposes and with approval by the institutional animal ethics committee. BALB/c nude mice (Nu/Nu, female, 5-6 weeks old) were purchased from the Animal Resources Centre (Perth, Wash.) and maintained under pathogen-free conditions. A549 cells (5×106) in 100 µl PBS were injected subcutaneously into the flanks of the mice and the resulting tumour were measured using digital callipers. The tumour volume was calculated using the following formula: Volume=(larger diameter)× (small diameter)2/2. Once the tumours had reached 100 mm3, mice were divided into groups of 9 and each group administered either RB-012 in saline, FTY720 in saline or saline alone by intraperitoneal injection daily. Initially RB-12 and FTY720 were administered at 2 mg/kg for two days and then the dose was increased to 5 mg/kg for two weeks after which RB-012 was increased to 10 mg/kg but FTY720 maintained at 5 mg/kg. During this dosing regime tumours were monitored twice a week. Differences between samples were analysed using 2 way Anova and statistical significance was accepted at $P<0.05$.

Example 2—N-Alkyl Trimethylammonium Compounds Render 14-3-3 Dimer Interface Susceptible to Phosphorylation by Dimer Disruption and Induce Mitochondrial Apoptosis To assess the structure-activity of agents capable of rendering 14-3-3 phosphorylatable, we assessed other non-sphingoid cationic lipids and in particular, quaternary ammonium compounds for effects on 14-3-3 phosphorylatability. In our in vitro system using recombinant 14-3-3 and PKA catalytic subunit, we found that N-alkyl trimethyl ammonium molecules (TMA) with alkyl chains of 12 carbons or longer were effective at rendering 14-3-3 phosphorylatable, whereas molecules with shorter alkyl chains were ineffective (FIGS. 1A & B).

Figure 1B:
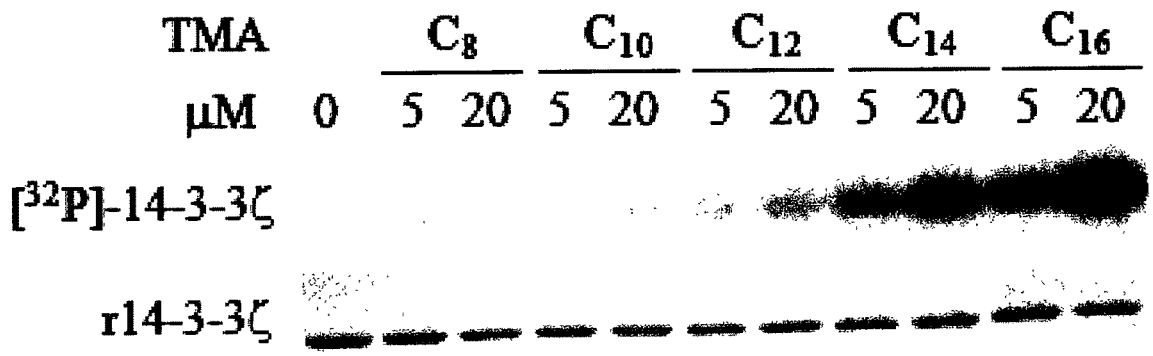
Figure 1C:
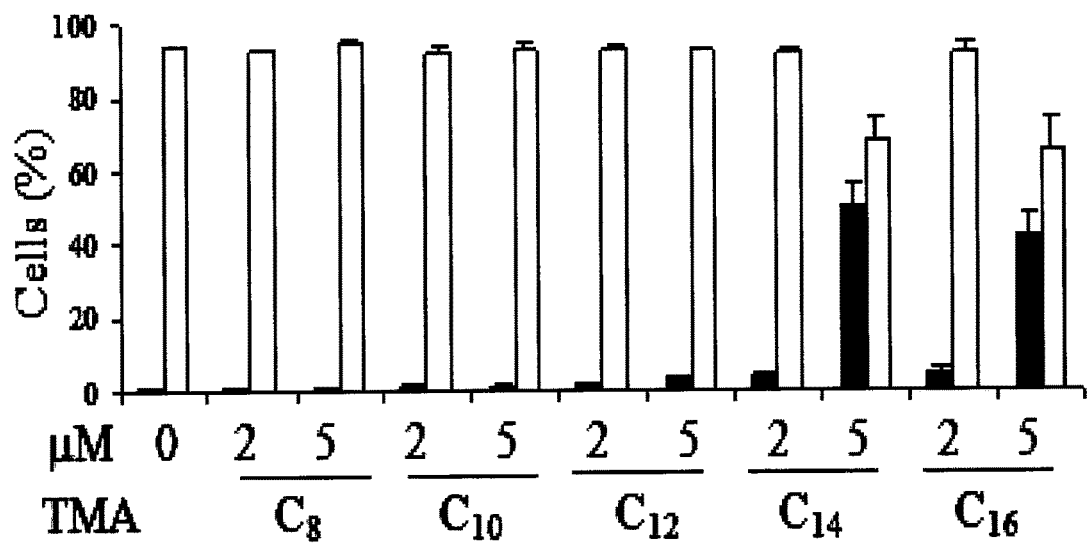

We tested whether the N-alkyl trimethylammonium series could induce cell death of Jurkat cells. Cell death was assessed by flow cytometry after 20 hours of treatment by analysis of viable cells together with tetramethylrhodamine ethyl ester (TMRE) staining to monitor mitochondrial permeability transition (($\Delta\Psi_M$), commonly associated with the commitment to apoptosis (FIG. 1C). The ability of the N-alkyl TMA molecules to induce mitochondrial permeability transition was entirely consistent with their ability to render 14-3-3 monomeric and phosphorylatable, suggesting that like sphingosine, these longer TMA molecules interfere with dimeric 14-3-3 protein functions in cells, upstream of mitochondrial permeabilisation and result in commitment to apoptosis.

Figure 2A:
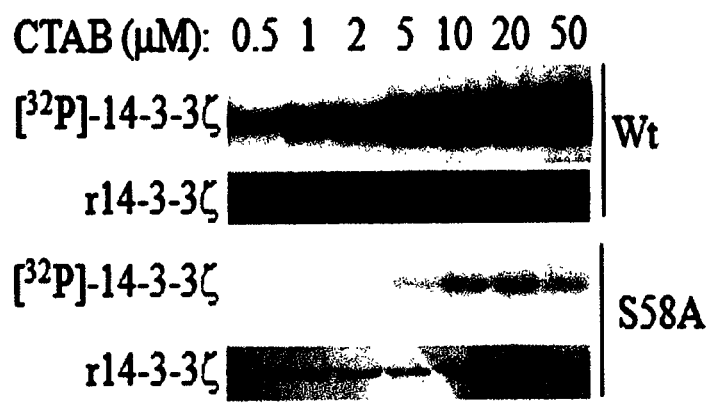
FIGS. 2A-2C show the effect CTAB ($C_{16}$-TMA) on 14-3-3 phosphorylation and cell viability.
Figure 2B:
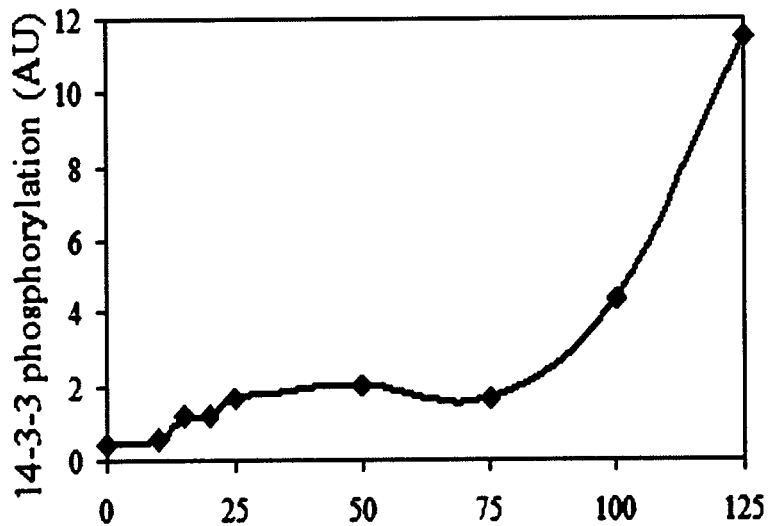

Using S58A recombinant 14-3-3 protein we confirmed that Ser58 in the dimer interface of 14-3-3ζ was the only phosphorylation site revealed by $C_{16}$-TMA, (cetyltrimethylammonium bromide, also known as CTAB) (FIG. 2A) and observed dose-dependent increase in 14-3-3 phosphorylation with increasing CTAB concentration. At high concentration, long chain N-alkylated TMA molecules have detergent properties. Therefore we assessed CTAB's effect on 14-3-3 phosphorylation more closely to assess whether non-specific denaturation of 14-3-3 was occurring. In dose-response studies we found that CTAB was able to induce 14-3-3 phosphorylation at low micromolar concentrations, plateauing above 25 µM (FIG. 2B). The reported critical micelle concentration for CTAB is 0.92 mM, thus these results are consistent with CTAB binding to discrete high affinity binding sites in 14-3-3 at concentrations well below it's CMC whereas at concentrations above 75 µM, the phosphorylation of 14-3-3 increased dramatically (FIG. 2B), potentially indicating more non-specific effects of generalised protein denaturation. Similar results have been observed with the binding of the related $C_{14}$-TMA compound to BSA.

To demonstrate that the TMA-induced mitochondrial permeability transition is associated with apoptosis, we confirmed the ability of CTAB to induce caspase-3 activation in Jurkat cells (FIG. 2D), a characteristic marker of apoptosis. Furthermore we demonstrated that, as with FTY720, Bcl-2-over-expressing Jurkat cells were protected from CTAB-induced cell death, indicating that the CTAB-induced apoptosis is mediated by the mitochondria (FIG. 2D). Thus, together these data suggest that at concentrations well below CMC, TMA molecules are able to bind and alter 14-3-3 proteins in cells, leading to disruption of 14-3-3 dimers and thus induce mitochondrial apoptosis.

Example 3—Novel Sphingomimetics Render 14-3-3 Dimers Susceptible to Phosphorylation and Cause Mitochondrial Apoptosis Our results with long chain TMA molecules and other sphingo-mimetics, suggest that basic lipid-like molecules bind discrete sites in 14-3-3 dimers, causing disruption of the dimer interface and thereby allowing kinases access to the Ser58 phosphorylation site. In order to generate more 14-3-3-selective agents we generated two derivatives, denoted RB-011 and RB-012 (FIG. 3A) for testing. These analogues lack hydroxyl sites for phosphorylation and therefore cannot be converted to phospho-species with immune suppressant characteristics.

Initially we tested the RB compounds in our in vitro 14-3-3 phosphorylation assay. We found the compounds were capable of rendering 14-3-3 phosphorylatable in a dose dependent manner (FIG. 3A). We then assessed the RB compounds ability to induce cell death of Jurkat cells. RB-011 and -012 were readily able to activate apoptosis at 5 µM, as determined by caspase-3 activation within 5 hours (FIG. 3B), and Annexin V presentation and loss of viability at 24 hours (FIG. 3C), consistent with these two eliciting disruption of 14-3-3 dimers.

The effect of RB-011 and -012 on cells was characterised more closely. We determined the $ED_{50}$ for apoptosis induction in Jurkat cells by assessing the initial activation of caspase-3 at 5 hours, before any loss of cell viability. RB-011 was slightly more potent than RB-012 at initiating apoptosis with an ED50 of 2 µM compared with 3 µM for RB-011 (FIG. 4A). Biochemical characterisation of RB-treated Jurkat cells revealed that after 4 hours of treatment PARP cleavage had occurred, consistent with the commitment to apoptosis (FIG. 4B, upper panel). Using phospho-specific antibodies, active stress-activated protein kinases p38 and JNK were also detected after 4 hours treatment with RB (FIG. 4B, second and third panel). Immunoblotting of 14-3-3 revealed a clipped form after 4 hours of RB treatment (FIG. 4B, bottom panel) probably associated with caspase cleavage as 14-3-3 proteins have previously been shown to be susceptible.

These analyses indicate that the activation of apoptosis in response to the RB compounds is rapid, occurring by 4 hrs of treatment. Additionally, over-expression of Bcl-2 completely protected the Jurkat cells from the RB compounds (FIG. 4C) as determined by analysis of viability and caspase activation after 24 hrs treatment, confirming that the compounds initiate mitochondrial-mediated apoptosis.

Example 4—RB Compounds Cause Rapid Inhibition of PI3K-AKT and MAPK Signalling

Figure 5A:
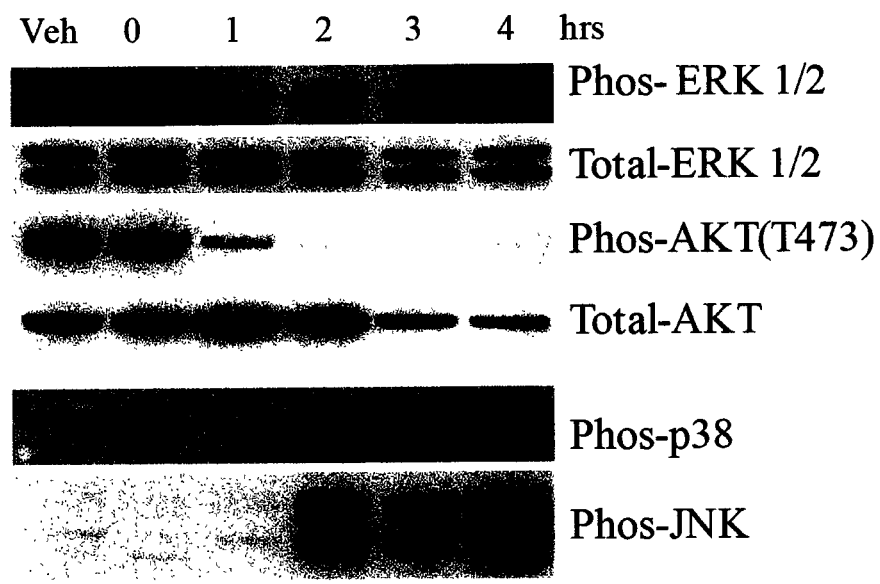
FIGS. 5A-5B show the effect of 7.5 µM RB-012 on signalling and apoptosis in Jurkat cells.

To more closely characterise the signalling changes associated with RB treatment of Jurkat cells we carried out time course studies using RB-012 and prepared cytosolic extracts for immunoblotting. Strikingly, phospho-specific antibodies revealed rapid dephosphorylation of both ERK and AKT (within 1 hour) upon RB-012 treatment (FIG. 5A first and third panel), indicating down-regulation of the MAPK and PI3K signalling pathways respectively. Activation of SAPKs p38 and JNK however was not detected until 2 hours post RB-012 treatment (FIG. 5A fourth and fifth panels), after ERK and AKT inactivation.

Figure 5B:
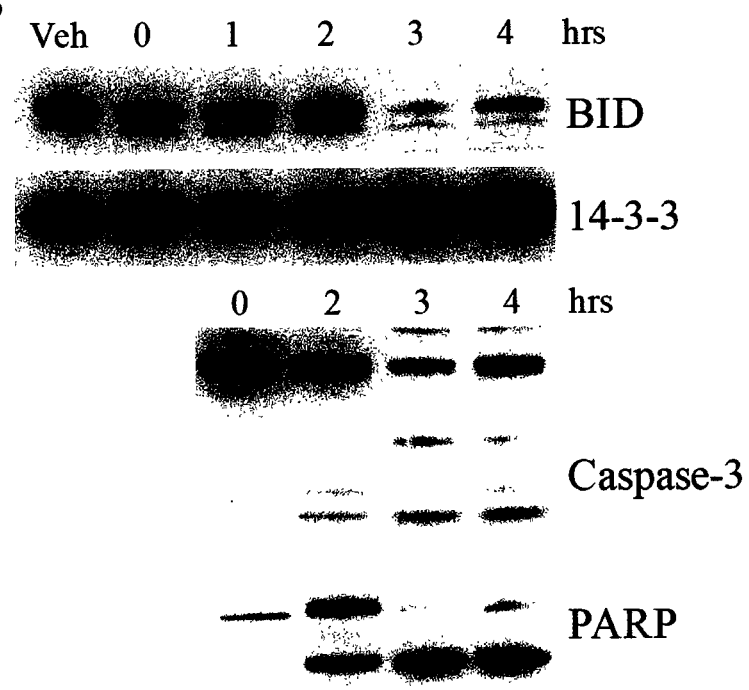

In the same time course studies apoptotic markers were analysed by immunoblotting. BID cleavage is associated with diverse apoptotic stimuli and has been shown to occur after mitochondrial de-permeablisation and apoptotic commitment via a caspase-3 mediated process in Jurkat cells. We analysed BID processing after RB-12 treatment and found that BID cleavage is detected at 3 hours of RB-012 treatment (FIG. 5B, first panel). Immunoblotting for 14-3-3 over the time course revealed that clipping of 14-3-3 protein is detectable at 2 hours (FIG. 5B, second panel), consistent with activation of pro-caspase-3 (FIG. 5B, third panel). Additionally, PARP cleavage was detectable at 2 hours (FIG. 5B, fourth panel). Thus commitment to apoptosis in response to RB-012 occurs within 2-3 hours of treatment, after the initial effects on MAPK, PI3K and SAPK signalling.

Example 5—RB Compounds Reduce A549 Lung Cancer Cell Growth

RB-011 and -012 exhibit apoptotic activity on Jurkat cells. Their effect is mediated at least in part by disruption of functional 14-3-3 dimers and inactivation of AKT and MAPK signalling pathways. These characteristics are desirable for a new anti-cancer therapy. We therefore sought to validate these compounds on human cancer cells where 14-3-3 over-expression has been implicated in tumour aggression. Non-small cell lung cancer (NSCLC) has been identified as a cancer in which the degree of 14-3-3 over-expression correlates strongly with poor patient survival and disease severity. We therefore assessed the effect of the RB-011 and -012 molecules on the NSCLC line A549 (FIG. 6).

Figure 6A:
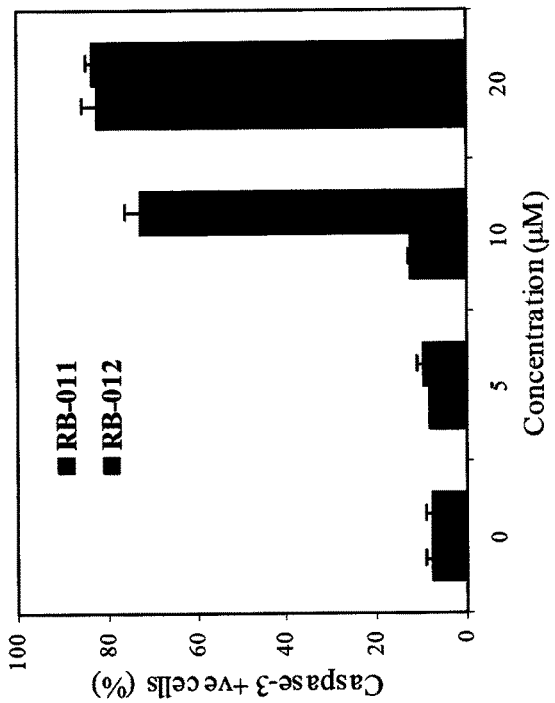
FIGS. 6A-6D show the effect of RB-011 and RB-012 on cancer cells and on a cancer xenograft.
Figure 6B:
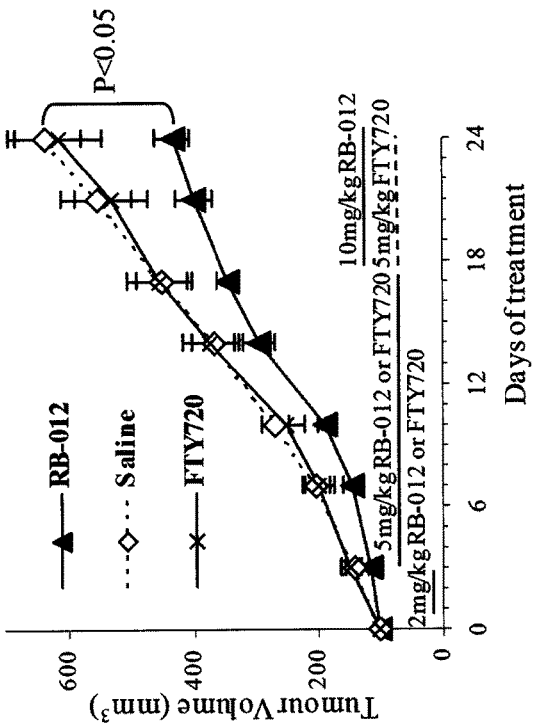
Figure 6C:
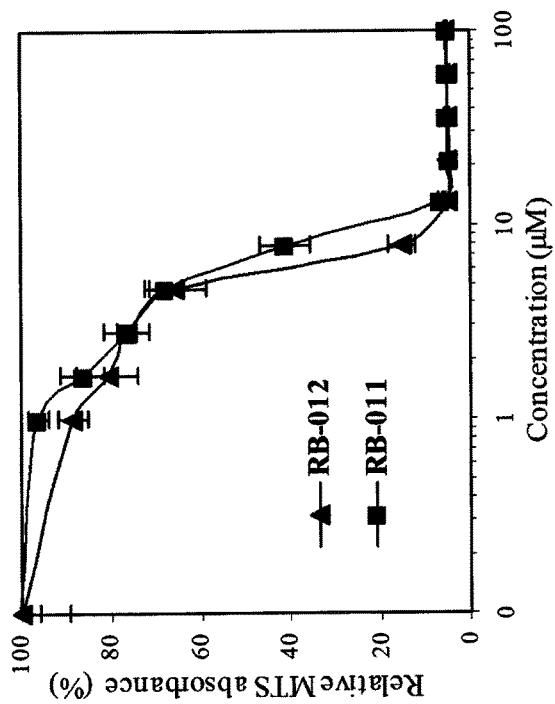
Figure 6D:
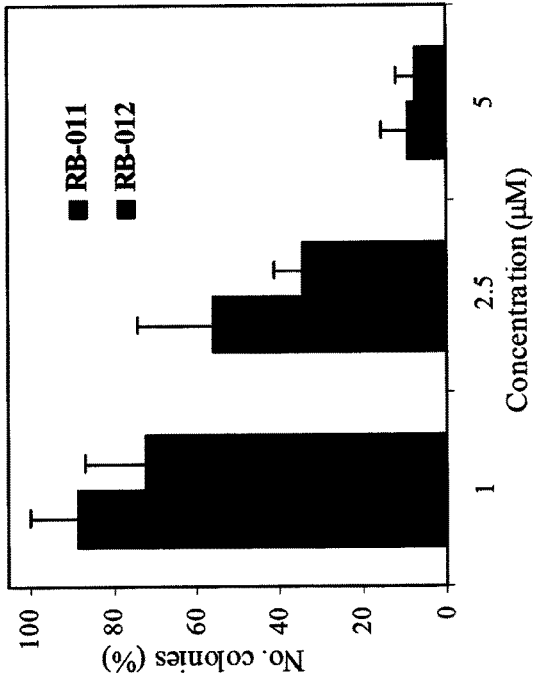

Firstly, we performed survival assays using MTS and found that after 48 hrs treatment the RB compounds reduced cell viability in a dose dependent manner (FIG. 6A). As with the Jurkat cells, RB-012 was slightly more potent than RB-011 with an IC50 of 5.5 µM compared with 7 µM for RB-011 (FIG. 6A). We assessed the ability of the RB compounds to induce A549 cells apoptosis by monitoring caspase-3 activation (FIG. 6B). Both compounds induced caspase-3 activation with RB-012 exhibiting showing greater potency. The compounds were then tested for their effect on A549 colony formation in soft agar, a measure of their neoplastic state. Both compounds reduced colony formation in a dose dependent manner with RB-012 again showing slightly greater potency (FIG. 6C). The ability of the RB compounds to reduce growth and induce apoptosis of the A549 cells is encouraging and suggests potential anti-cancer activity.

Finally, we studied the effects of RB-012 in vivo. To assess any potential toxic effects, Balb/C nude mice were administered RB-012, delivered in saline, daily by intraperitoneal injection at 5 mg/kg. Over a course of 28 days no adverse effects were noted with the exception of minor cramping immediately after injection that subsided within 10-20 minutes. There was no pathology associated with the cramping suggesting a physiological response and over the course of the treatment the mice developed a tolerance to this response. The body weight of the mice was unaltered suggesting that the compound had no major toxic effects. Blood and bone marrow samples were analysed at the end of the treatment period to look for alterations in steady state haemopoiesis and no changes were observed (data not shown).

To assess the effect of RB-012 on human lung cancer growth in vivo, A549 cells were implanted subcutaneously on the flanks of Balb/C nude mice and tumours allowed to develop until they had reached a volume of 100 mm$^3$. RB-012 or saline was then administered daily to assess the effect on tumour growth. Initially, to reduce the cramping and encourage tolerance, 2 mg/kg RB-012 was administered for two days and then the dose was increased to 5 mg/kg daily for two weeks. Tumour volume was monitored twice a week and after two weeks of treatment mice administered RB-012 had tumours that were 20% smaller than mice receiving saline. The RB-012 dose was then increased to 10 mg/kg for a further week which was well tolerated without adverse effects. The tumours on the RB-012 treated mice continued to grow more slowly and after the third week were 30% smaller than those of saline-treated mice (P<0.05). Interestingly, this was in contrast to mice receiving FTY720 at 5 mg/kg which showed no reduction in tumour size. In contrast to other reports FTY720 was not tolerated at 10 mg/kg and caused severe cramping with cardiac arrhythmia, with fatality in some cases. Therefore we were unable to increase FTY720 dosing to match RB-012.

Discussion

The widespread over-expression of 14-3-3 proteins in human tumours has highlighted the significance of 14-3-3 proteins in cancer development. Increased 14-3-3 expression provides cancer cells with enhanced protection against apoptotic mediators and thus 14-3-3 proteins are an attractive target for anti-cancer drug development. There is considerable effort identifying molecules with the ability to interfere or block the binding of 14-3-3 proteins to client proteins, but these studies involve identifying molecules that compete with client proteins for binding in the amphipathic groove. Our approach is entirely different in that it exploits discrete sphingolipid binding site(s) on 14-3-3 that once occupied, cause dimer disruption.

Figure 2C:
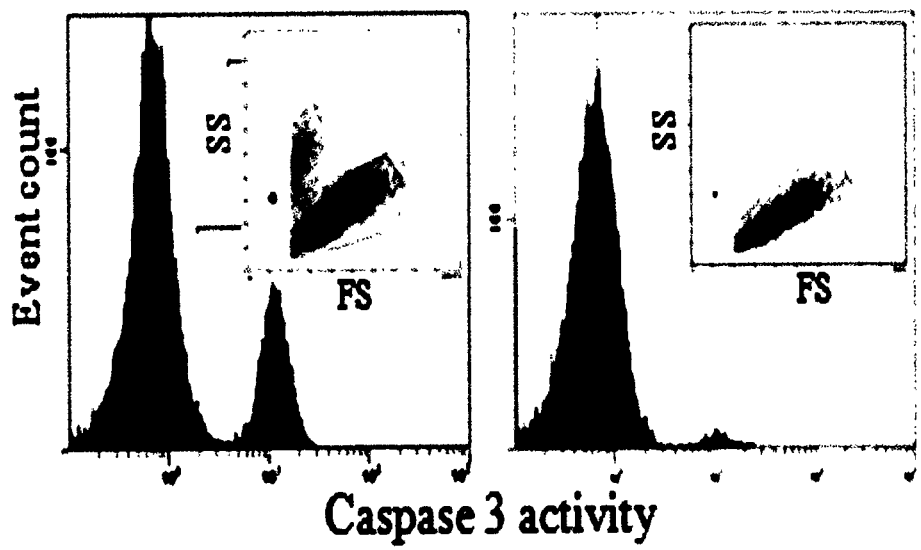

We identified alkylated trimethylammonium (TMA) molecules as modulators of 14-3-3 in vitro and correspondingly capable of inducing apoptosis of Jurkat cells. From a chemical series of trimethylammonium compounds we determined that the length of the alkyl chain was an important factor in determining the effect on 14-3-3 modulation and Jurkat cell apoptosis. Long chain TMAs have the greatest potency both in in vitro 14-3-3 phosphorylation assay and inducing Jurkat cell apoptosis (FIG. 1). Additionally, the long-chain TMAs induce apoptosis in Jurkat cells at concentrations well below CMC which is mediated by the mitochondrial pathway (FIG. 2). Taken together these data support the notion that long-chain TMAs induce apoptosis by interfering with dimeric 14-3-3 in the cell. Analytical ultracentrifugation supports this idea, showing that long chain TMAs disrupt 14-3-3 dimers to release monomeric forms of 14-3-3 (FIG. 2C).

The compounds tested in this study exhibit varying ability to render 14-3-3 phosphorylatable in vitro and this coincides with their ability to induce apoptosis of Jurkat cells (FIG. 3). In particular RB-011 and RB-012 have potent ability to induce apoptosis of Jurkat cells within 4 hours of treatment and have $ED_{50}$s in the low micromolar range (FIG. 4). Time course studies revealed rapid inactivation of ERK and AKT signalling within one hour of treatment of Jurkat cells with RB-012 followed by activation of SAPKs, JNK and p38 by 2 hours. The apoptotic cascade then proceeds with caspase-3 processing, PARP and BID cleavage. These are important findings as they reveal the cellular effects of RB-012 occurring in a time-dependent manner with primary effects on cell signalling occurring prior to apoptotic commitment.

We have tested RB-011 and -012 for anti-cancer effects on NSCLC cells. We have shown that our compounds inhibited A549 cell survival and colony formation in soft-agar and induced apoptosis (FIG. 5). We have also demonstrated the therapeutic potential of RB-012 in an in vivo A5-(9-xenograft model and shown that RB-012 reduces tumour growth by up to 30% over a three week course of treatment. The compound was well tolerated with less side effects than FTY720 which did not elicit a reduction in tumour growth in our study. FTY720 has been demonstrated to reduce tumour growth in other experimental cancer models but at higher doses (10 mg/kg/day), suggesting that the RB-012 compound is more potent. FTY720 is readily converted to a phospho-form by endogenous sphingosine kinases (SK) (and in this form acts as a sphingosine-1-phosphate analogue which mediates the drug's immunosuppressive action). RB-012 cannot be phosphorylated (it lacks a phosphate accepting hydroxyl moiety) and unlike FTY720, does not affect SK activity (data not shown) and therefore compared with FTY720, our RB-012 compound is more selective in action. Compared with other 14-3-3-directed small molecules, our RB compounds are non-competitive in that they do not compete with endogenous phospho-clients for binding in the amphipathic groove. Taken together, this data provides valuable proof-of-principle for our 14-3-3 dimer disruption approach to cancer drug discovery. Furthermore, the compounds we have identified are potential leads for future anti-cancer drug development.

Example 6—Treatment of Breast Cancer

Subjects suffering from breast cancer may be identified by known clinical characteristics.

Treatment of human patients with breast cancer may be undertaken by either oral administration twice daily of a formulation including RB-011 and/or RB-012 (eg 50-500 mg) or by iv administration in isotonic saline (eg 50-500 mg).

Treatment with the compound(s) may be for a defined intervention period (for example 8-12 weeks) or be maintained indefinitely. Serum and/or plasma levels of the compound may be determined at various intervals and any adverse effects monitored. Dose or frequency adjustments can be made based on the serum concentrations, clinical symptoms and any adverse effects.

It is envisaged that treatment with the compound(s) will provide significant improvement in the clinical characteristics of the patients compared with a placebo, including reduced growth of the primary tumor and reduced metastasis.

In some circumstances, the level of 14-3-3 (eg protein, mRNA) and/or miR-451 can also be assessed as markers for identifying a patient suitable for treatment and/or for assessment of the prognosis of the patient.

Example 7—Murine Model of Wound Healing/Materials and Methods

A murine model of wound healing was utilised. In this model, 2×1 cm full thickness wounds were created in the dorsal skin. Wound healing was monitored using cohorts of mice humanely killed at 3, 5, 7 and 14 days post-wounding. Re-epithelialization was quantified histologically, by measuring the distance between epithelial margins sectioned in the transverse plane (Ansell D. M. et al. (2014) *Wound Rep Reg* 22: 281-287).

Mice

All procedures were performed under appropriate licenses and with the oversight of the relevant institutional animal ethics committees constituted according to the Animal Welfare Act 1985 of South Australia. Generation of 14-3-3ζ deficient mice (Cheah et al. (2012) *Mol Psychiatry* 17, 451-466 have been previously described.

Incisional Wounding

Incisional wounding was carried out as we have previously detailed (Lees et al. (2013) *The Journal of investigative dermatology* 133, 1330-1339). Briefly, two full-thickness 1 cm incisions were created on the dorsal skin of 12 week old female mice and allowed to heal. RB-11 (10 μg per mouse), 4-hydroxytamoxifen (50 μg per mouse) or vehicle was applied in a total volume of 20 μl to the edge of each wound using a micropipette and allowed to absorb into the skin. At the appropriate time point (2, 5, 7, 14 and 21 days) following incisional wounding, mice were humanely killed and tissues harvested. From each mouse, one wound was completed excised and fixed in 4% formalin overnight at 4° C. Following fixation, the wound was carefully bisected at the middle across the wound, processed and embedded in paraffin for histological and immunofluorescence analysis. Wound widths were measured on scanned images of H&E stained sections using NDPView slide scanning and image quantification software. The remaining wound was bisected across the wound, snap-frozen and processed for gene expression analysis.

Human Tissue Samples

For human wound samples, informed consent was obtained from each patient and the study protocols conformed to the ethical guidelines of the 1975 Declaration of Helsinki as reflected in approvals by the Health Service Human Research Ethics Committee and Central Northern Adelaide Health Service Ethics of Human Research Committee HREC/12/TQEHLMH/107, CNAH 11-CHREC-F007 and RAH 120113.

2-Photon Second Harmonic Generation (SHG) Microscopy

Histological samples were imaged using a 20×1.0 NA water immersion objective on an upright fixed-stage two-photon laser scanning microscope system (Zeiss). The excitation source was a Ti:Sapphire femto-second laser cavity (Newport Mai Tai), coupled into a LSM 710 scan module. An excitation wavelength of 890 nm was used to collect SHG signal (435±20 nm) from collagen. Signal was acquired from three separate areas measuring 320×320 μm² across each sample. Immunofluorescence and transmission images were co-acquired with SHG data.

Histological, Immunohistochemical and Immunofluorescence Analyses

Histology and immunohistochemistry were performed utilizing protocols as previously established (Ibbetson et al. (2013) *Am J Pathol* 183, 930-937; Samuel et al. (2011) *Cancer Cell* 19, 776-791; Samuel et al. (2011) PLoS One 6, e17143; Samuel et al. (2009) *Gastroenterology* 137, 902-913, 913 e901-911). Antigen retrieval buffer, method and antibody dilutions used appear in Table 51. Histology slides were imaged using a Hamamatsu Nanozoomer NDP slide scanner (Hamamatsu Photonics) and Digital Slide Server (Slidepath) software. Transmission and SHG images were acquired simultaneously using an LSM 710 two-photon excitation microscope (Zeiss). Immunofluorescence images were acquired using an LSM 700 confocal microscope (Zeiss).

In all images of sectioned wounds, we have adhered to the following convention. Dotted lines indicate wound edges (Figure S2A). Wound margin tissue is immediately to the left of each dotted line.

Cells

Primary dermal fibroblasts and keratinocytes were derived from murine skin. Dermal fibroblasts were transfected with a plasmid encoding eGFP-labeled paxillin (item 15223, Addgene) using Lipofectamine 2000 (Thermo Fisher Scientific) according to the manufacturer's instructions, or infected with lentivirus encoding eGFP (LMP-puro-eGFP) (Dickins et al., 2005) or mCherry (LMP-puro-mCherry) for live cell imaging. Fibroblasts were starved for 18-24 hours in serum-free DMEM. All immunoprecipitations were carried out using standard methods from RIPA buffer lysates containing 50 μg total protein, supplemented with phosphatase inhibitor cocktail (Roche) on Protein A magnetic beads (Bio-Rad). For the immunoprecipitations in the presence of phosphatase, the phosphatase inhibitor was omitted and 10 U alkaline phosphatase (New England Biolabs) was added per 50 μg immunoprecipitation.

Live Cell Imaging

Collagen organotypic matrices that had been remodeled by fibroblasts were imaged on day 5 of the collagen remodeling assay on an inverted Leica SP8 confocal microscope equipped with a femto-second pulsed multiphoton laser (Coherent Vision). A 20×0.4 NA water immersion objective was used. The samples were placed in a humidified heated chamber at 37° C. and imaged overnight. 512×512 pixel 8-bit image stacks were acquired at 30 min intervals. SHG was generated at 920 nm excitation and eGFP and SHG emission were co-acquired on external RLD HyDs. A 525/50 nm BP filter was used to selectively detect eGFP emission; the SHG signal was collected with a 460/40 nm BP filter. Image stack time-series were reconstructed with Imaris 8 (Bitplane) and presented as maximum intensity projections.

Dermal fibroblasts expressing eGFP-labeled paxillin were plated on collagen and imaged using a CV1000 spinning disk confocal system (Yokogawa) in a humidified, heated chamber at 37° C. Excitation was at 488 nm and eGFP fluorescence was acquired as 512×512 pixel 8-bit live cell image stacks from 3-4 fields per experiment using an electron multiplying charge-coupled device (EMCCD) camera at 3 min intervals. Image stack time-series were reconstructed using Cell Voyager software (Yokogawa) and presented as maximum intensity projections. Videos were exported as AVI files and processed in ImageJ to determine adhesion foci counts and area coverage measurements.

Quantitative Reverse-Transcription PCR Analyses

Wound margins samples for qPCR analyses were harvested, snap frozen in liquid nitrogen and ground while frozen using a pestle and mortar. RNA was extracted from pulverized tissue using TRIzol (Thermo Fisher Scientific) following the manufacturer's instructions and first strand cDNA synthesis and qPCR amplification carried out using the QuantiTect system and QuantiTect primer assays using the SYBR green method. Qiagen catalog numbers for primer assays used were:

| Species | Primer Assay |
| --- | --- |
| Col1a1 | QT00162204 |
| Col3a1 | QT01055516, QT02331301 |
| Ywhab | QT00126133 |
| Ywhaz | QT00105350 |
| Ywhah | QT01776012 |
| Ywhag | QT00288575 |
| Ywhae | QT00150738 |
| Ywhaq | QT01061165 |
| Sfn | QT02243605 |

Mammalian 18s rRNA-derived cDNA was amplified using specific primers known in the art. SYBR green signal from each test amplicon was normalized to that obtained from the 18s amplicon from the same samples and the results expressed as a fold-differences relative to 18s. All assays were carried out in triplicate on each sample.

Quantification of SHG Signal from Collagen or Immunofluorescence

ImageJ was used to calculate percentage area covered by SHG signal per image, after conversion to a binary image based upon a single manually determined threshold value applied across all images as previously described (Ibbetson et al., 2013; Samuel et al., 2011a). Results were expressed as medians, ranges and quartiles across all data sets for each histological type.

Gray Level Co-Occurrence Matrix (GLCM) Analysis

Collagen SHG signal captured from day 7 wounds as described above was processed using the procedure we have previously reported (Huo et al., 2015), to determine the correlation of the intensity of the SHG signal across the analyzed regions. Briefly, five 74×74 μm regions of interest from a maximum projection image were passed to the GLCM plugin (UMB GLCM features, Norwegian University for Life Sciences) modified to permit the testing of multiple directions and distances of comparison. The output of the plugin for each region of interest was 100 rows of the 5 texture parameters (contrast, uniformity, correlation, homogeneity and entropy) over each of 4 directions, a total of 2000 parameter values. These were saved as a text data file for each region of interest. Once all the images in the directory were analyzed, the data files were processed using a MATLAB (MathWorks) script that outputs the mean (with S.E.M.) value of each texture parameter for each image. A double exponential decay model was fitted to the data and the weighted mean decay distance for each sample was calculated.

Collagen Remodeling Assay and Determination of Cell Morphology

Rat-tail tendon collagen was prepared by extraction with 0.5 M acetic acid to a concentration of ~2 mg/ml. $8 \times 10^4$ cells/ml WT or 14-3-3ζ KO dermal fibroblasts (labeled with either eGFP or mCherry) were embedded in this three-dimensional collagen 1 matrix and incubated in DMEM with 10% FCS and 10 mM L-Glutamine at 37° C. and 5% $CO_2$. Detached polymerized matrix (2.5 ml) was allowed to contract for 11 days. During contraction, matrices were either left untreated or incubated with 10 µM RB-11. Media was changed on day 1 and on day 6. To calculate contraction rates and obtain information on cell morphology matrices were imaged every second day in phase contrast on a Leica DMIL LED inverted microscope with either a 4×/NA0.10 HI PLAN or a 10×/NA0.22 HI PLAN I air objective.

Measuring the mean diameter of three matrices and normalizing the diameter to day 1 determined contraction rates. Cell morphology was described by manually counting the number of cell protrusions/cell and the number of blebbing cells.

To determine the circularity of cells images were processed in ImageJ (NIH) according to following routine. Images were converted to 8 Bit images and cropped to an image size equivalent to 1800 nm$^2$. Grey values were thresholded to select cells. The 'analyze particles' function was used to determine circularity of cells. Circularity values range from 0 to 1 with '0' representing rod-shaped cells and '1' representing perfectly circular cells.

Data was plotted in GraphPad Prism 6 software and statistical differences were determined by one-way ANOVA with Tukey's post-test.

Bone Marrow Chimeric Mice

Recipient female BALB/c mice at least 8 weeks of age were given 750 cGy gamma irradiation using a linear accelerator. 20-24 hours post irradiation mice were engrafted with female bone marrow cells (WT donor into WT recipient as irradiation control; KO donor into WT recipient or WT donor into KO recipient) using the CD45.1 and CD45.2 markers to distinguish donor from recipient cells at harvest. Cells from donor mice were combined within the group and then injected into the tail vein of recipients with the equivalent of each donor mouse repopulating 3 recipient animals. Mice were housed for 4 weeks, in sterile conditions with prophylactic antibiotics, with daily health checks and then wounded as outlined above.

Statistical Analyses

Box and whisker plots show medians and quartiles or inter-quartile ranges of non-parametric data, with P-values calculated using either the Kruskal-Wallis (>3 groups) or Mann-Whitney (2 groups) test together with Dunnet's post hoc test to compare the spread of values unless otherwise indicated. Histograms show means and standard errors of data exhibiting a normal distribution and were analyzed using Student's t-test or ANOVA. In all cases, P<0.05 was used as the significance cut-off.

Example 8—14-3-3ζ Deficient Skin (KO) Heals Faster than Wild-Type (WT) Skin 14-3-3ζ-deficient mice were generated as described previously (Mol Psychiatry. 2012 April; 17(4):451-66). Briefly, 14-3-3ζ Gt(OST062)Lex mutant mice carrying gene trap constructs that contain the βGeo reporter gene (referred to here as 14-3-3ζ-deficient mice) were derived from Lexicon Genetics ES cell line OST062. The gene trap vector in 14-3-3ζ Gt(OST062)Lex mice resides within the first intron of the Ywhaz gene, which encodes 14-3-3ζ. ES cell lines were amplified and injected into 129 Sv/J blastocysts. Resulting germ line transmitting males were backcrossed onto the BALB/c background and maintained by heterozygous matings.

Figure 7A:
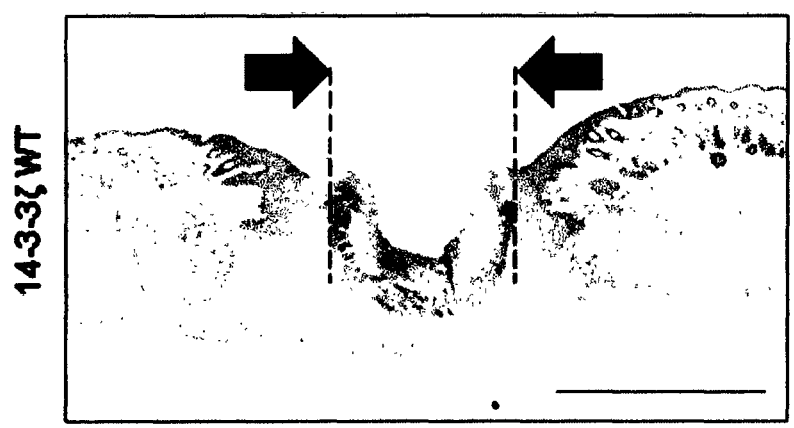
FIGS. 7A-7C show photomicrographs of histological sections used to measure wound width (distance between the black arrows) at day 7 post wounding in normal wild-type mice (14-3-3ζ WT, FIG. 7A) and 14-3-3ζ-deficient (14-3-3ζ KO, FIG. 7B) mice.
Figure 7B:
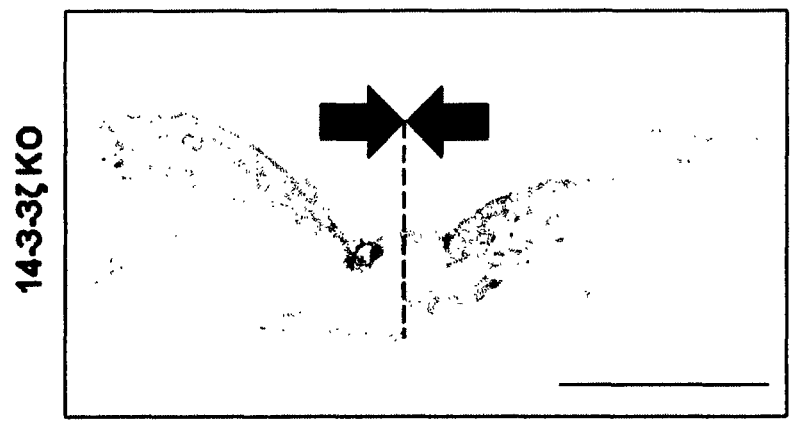
Figure 7C:
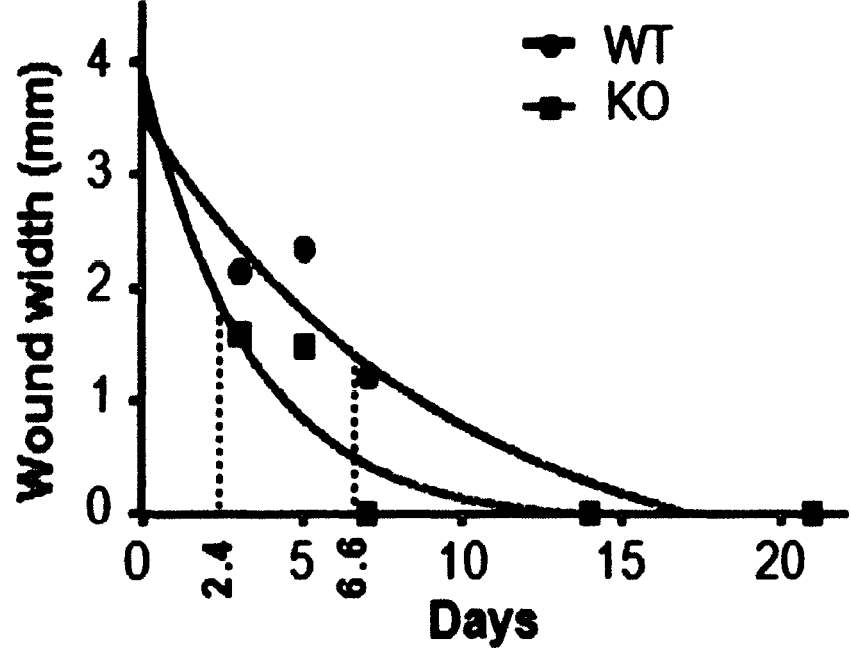

The data is shown in FIG. 7. The data shows that 14-3-3ζ deficient skin (KO) heals faster than wild-type (WT) skin.

Figure 8:
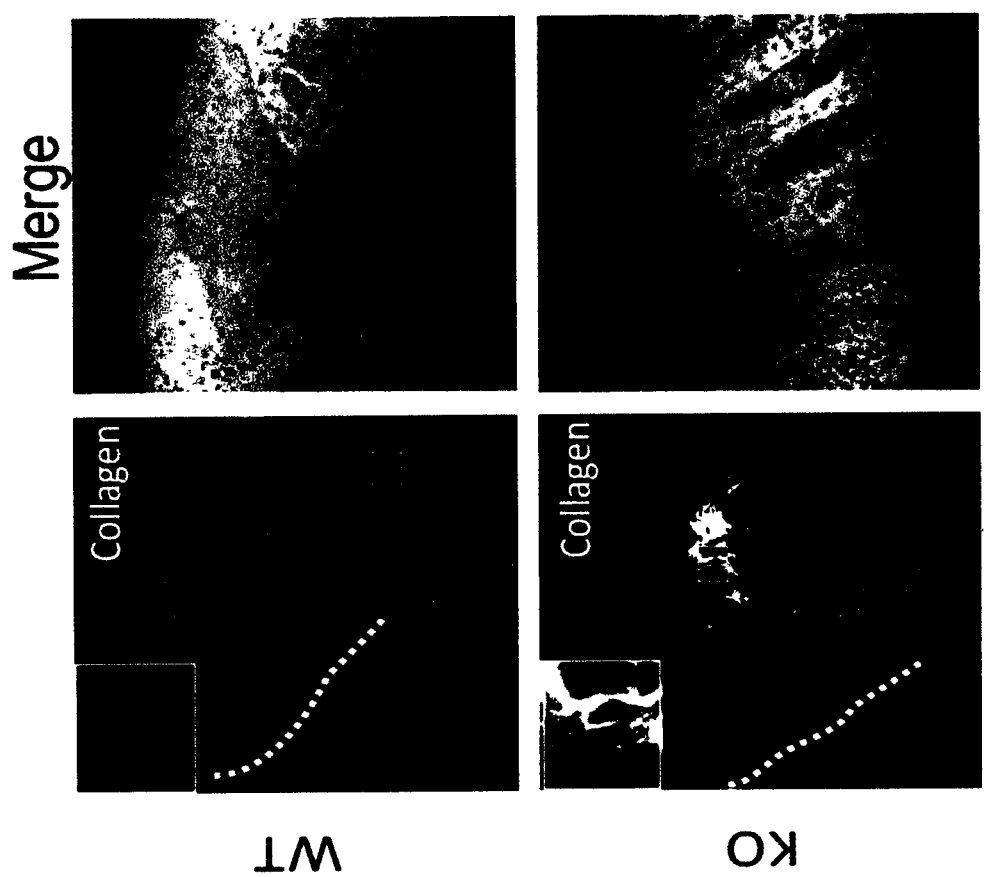
FIG. 8 shows second harmonic generation (SHG) and transmission 2-photon signal obtained adjacent to wound margins (indicated by dotted lines) in wild-type and 14-3-3ζ-deficient mice. The SHG signal is specific for collagen and indicated an increased amount and decreased remodelling of collagen in 14-3-3ζ-deficient wounds compared to that in wild-type wounds. The two lower left panels are higher power magnifications of the areas bounded by yellow boxes. The panel to the right shows quantification of the imaging data, revealing higher levels of unremodelled collagen at the margins of 14-3-3ζ-deficient wounds compared to wild-type counterparts.
Figure 9:
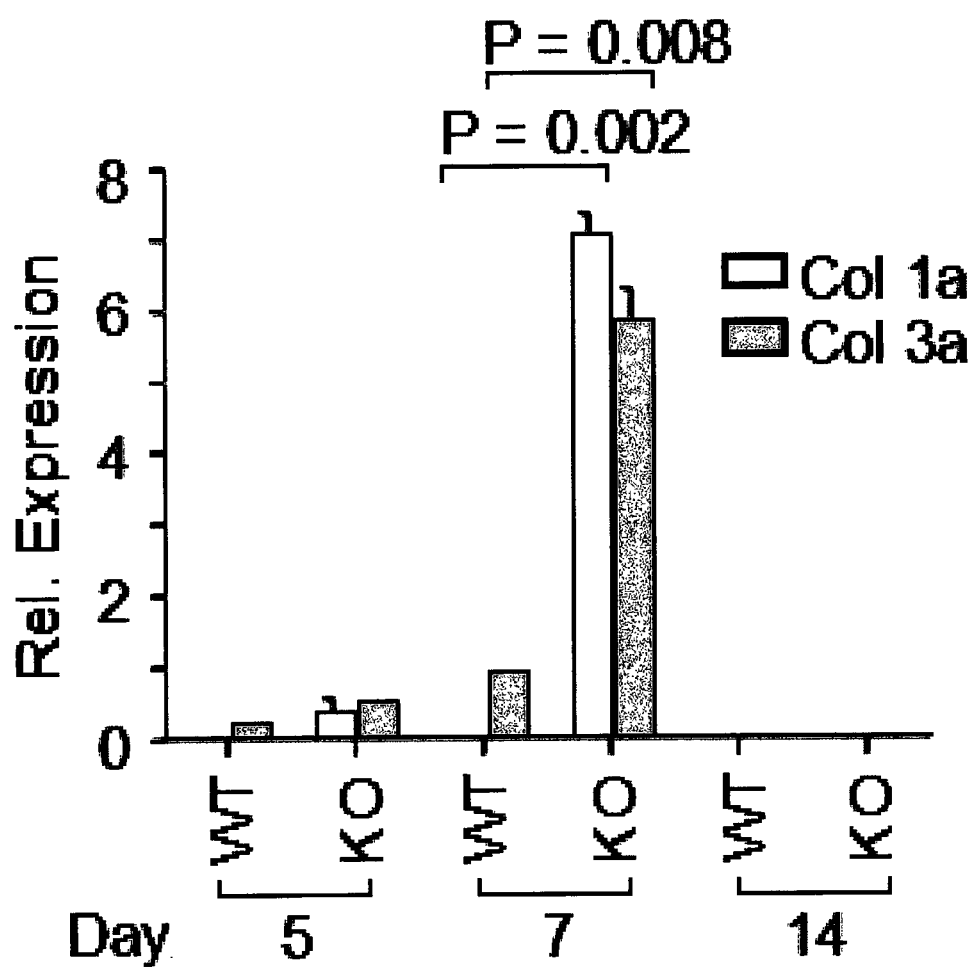
FIG. 9 shows data from quantitative reverse transcriptase polymerase chain reactions carried out to measure the levels of Collagen 1a and 3a-specific messenger RNA expressed at wound margins 5, 7 and 14 days following wounding. The data indicated that both isoforms were elevated in 14-3-3ζ-deficient wounds compared to that in wild-type skin, particularly at day 7.

Example 9—Collagen Levels are Up-Regulated at the Margins of 14-3-3-Deficient Wounds The data is shown in FIG. 8 and FIG. 9.

Histological sections (4-10 µm) of formalin fixed and paraffin embedded tissue derived from wild-type and 14-3-3ζ-deficient wounds were stained using the standard protocol with haematoxylin and eosin, washed dehydrated and mounted in DPX. SHG signal (435±20 nm) from collagen was captured using 890 nm excitation wavelength while simultaneously acquiring a transmission image. Images were quantified using a custom plug-in developed for ImageJ image analysis software as described in Samuel et al. (2011) Cancer Cell, 19, 776-791). The analysis indicated an increased amount and decreased remodelling of collagen in 14-3-3ζ-deficient wounds compared to that in wild-type wounds.

Figure 10:
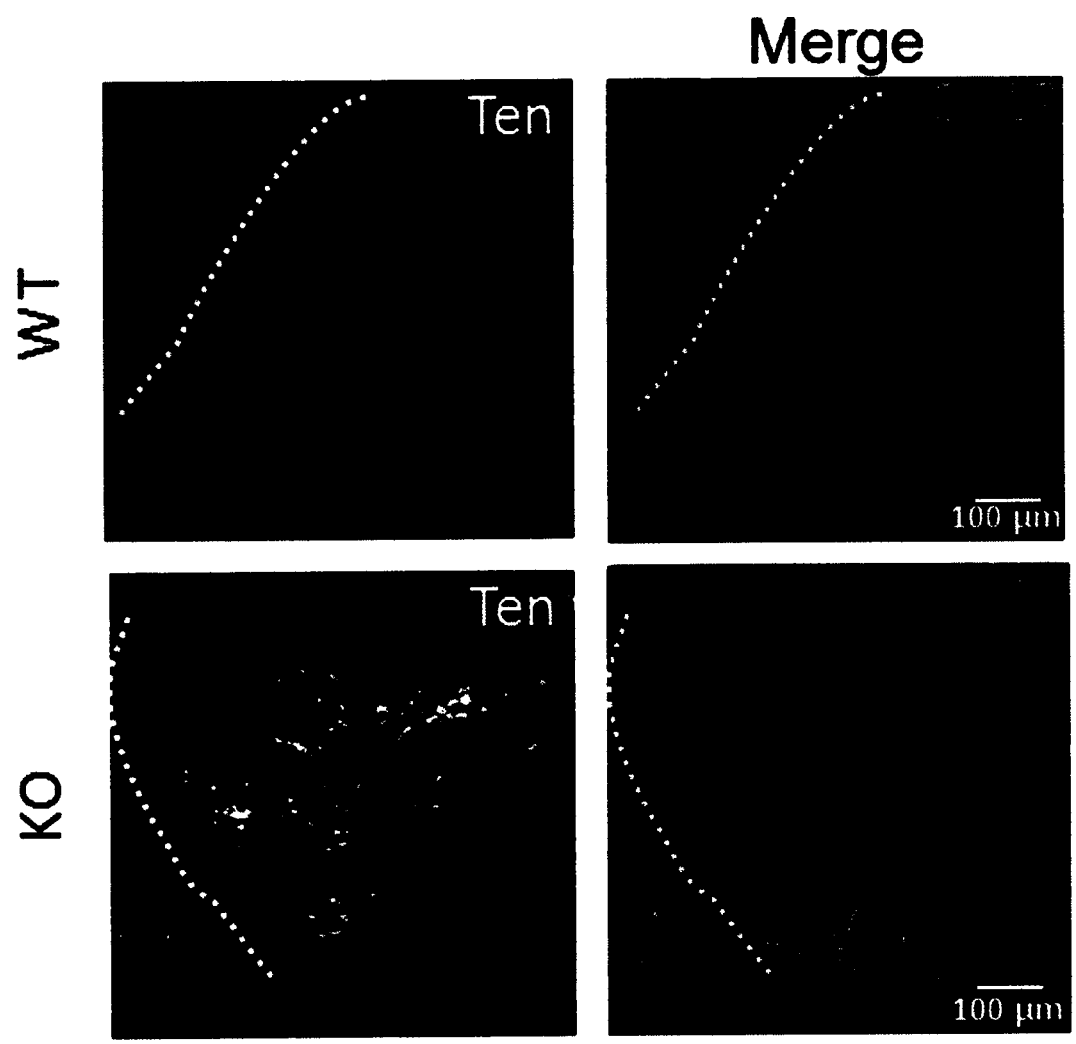
FIG. 10 shows immunofluorescence analysis of tenascin C in wild-type and 14-3-3ζ-deficient wound margins (dotted lines). Cytokeratin 17 labelling (green) marks the epidermal cells. The data showed that tenascin C levels were elevated at 14-3-3ζ-deficient wound margins compared to that at wild-type wound margins.
Figure 11A:
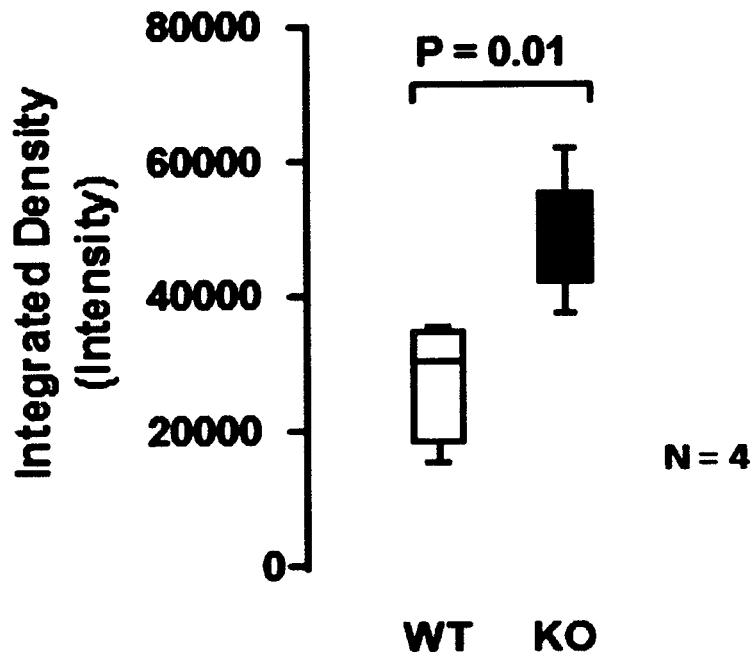
FIGS. 11A-11B show area coverage analysis of periostin (FIG. 11A) and tenascin C (FIG. 11B) levels at wild-type and 14-3-3ζ-deficient wound margins derived from immunofluorescence analysis as described in FIG. 4. The data showed that both periostin and tenascin C were elevated at 14-3-3ζ-deficient wound margins compared to that at wild-type wound margins
Figure 11B:
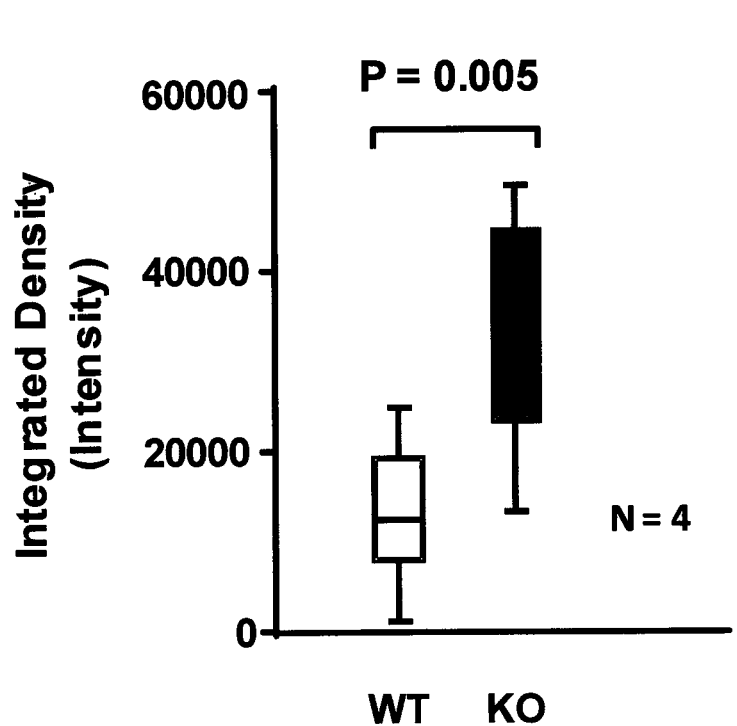

Example 10—the Dermal Extra-Cellular Matrix is Denser and Un-Remodelled in 14-3-3ζ-Deficient Wounds The data is shown in FIGS. 10 and 11.

Histological sections of wounds derived from wild-type and 14-3-3ζ-deficient mice were subjected to immunofluorescence analysis using antibodies specific for periostin (Sigma-Aldrich, SAB4200197, 1:500) and tenascin-C(Ten, Merci-Millipore AB19013, 1:100) following antigen retrieval for 15 minutes in a microwave pressure cooker in 10 mmol/L citrate buffer, pH 6.0. The data indicated elevated levels of periostin and tenascin-C in 14-3-3ζ wound margins compared to those observed in wild-type wounds.

Example 11—14-3-3ζ-Deficient Mice Exhibit Perturbed Epidermal Homeostasis and Faster Wound Healing Kinetics We conducted histological analysis of skin biopsies taken from 14-3-3ζ wild-type (WT) and 14-3-3ζ deficient (KO) mice and found that 14-3-3ζ KO mice exhibited a ~15% thinner epidermal layer than 14-3-3ζ WT mice and this phenomenon was enhanced to >30% when epidermal hyperproliferation was elicited by topical treatment with 12-O-Tetradecanoylphorbol-13-acetate (TPA), an activator of Protein Kinase C. We also confirmed that 14-3-3ζ gene-targeted mice did not express 14-3-3ζ in the skin at the protein or mRNA levels. Expression analysis also revealed that other 14-3-3 family members were not differentially regulated in 14-3-3ζ-deficient skin Taken together, these data suggest that 14-3-3ζ has a non-redundant function in regulating epidermal homeostasis.

Given the phenotype reminiscent of impaired mechanical signaling in 14-3-3ζ KO skin, we next sought to determine whether 14-3-3ζ has a role in the re-establishment of normal mechano-reciprocity during in wound repair, using a well-established model of incisional wound healing to assess the kinetics and mechanisms of wound healing in 14-3-3ζ KO mice compared to 14-3-3ζ WT littermates. 14-3-3ζ KO mice exhibited faster wound healing kinetics compared to 14-3-3ζ WT mice. Regression analysis carried out on healing times showed that the median wound healing time was 2.4 days in 14-3-3ζ KO mice compared to 6.6 days in 14-3-3ζ WT littermates, a >2.5-fold increase in the speed of re-epithelialization. In 14-3-3ζ WT mice, wound healing was accompanied by elevated 14-3-3ζ mRNA and protein levels compared to those observed in WT skin. No other 14-3-3 family member was upregulated at wound margins. To determine whether wound closure in KO mice was promoted by an increased number of dermal fibroblasts, a heterogeneous cell type that is crucial for the re-establishment of the dermal ECM and provides the contractile force for wound closure, we carried out immunofluorescence analysis for the broad-based fibroblast marker S100A4/Fsp1 and the transient myofibroblast-specific marker α-smooth muscle actin in wounded and unwounded skin, but found no differences in the numbers of these cells in the two genotypes at all time points. Also, SMA levels were comparable in primary dermal fibroblasts derived from 14-3-3ζ KO or WT mice. This observation suggested that rapid wound healing in 14-3-3ζ KO skin was not mediated either by an increased total number of dermal fibroblasts or an increased population of myofibroblasts during wound healing.

Example 12—Rapid Wound Healing Kinetics in 14-3-3ζ Deficient Mice are Associated with Changes in ECM Composition Normal re-epithelialization following wounding is critically dependent on the re-establishment of the dermis, which is mainly composed of an extra-cellular matrix (ECM) populated by dermal fibroblasts and immune cells. The ECM also exerts the extra-cellular force required to maintain tissue integrity. Dermal fibroblasts produce and remodel the fibrillar proteins that constitute the ECM. We hypothesized that differences in the composition of the ECM and resulting difference in extra-cellular force generation may influence wound healing kinetics in 14-3-3ζ KO skin. We therefore analyzed collagen composition and remodeling at the margins of wounds using second harmonic generation (SHG) microscopy. Area coverage analysis of the SHG signal from collagen fibers revealed a significantly higher level of collagen at wound margins in 14-3-3ζ KO skin compared to WT skin following incisional wounding at both the protein and mRNA levels. Furthermore, collagen fibers at 14-3-3ζ KO wound margins appeared less organized than those in WT wounds and lacked the uniformly bundled, parallel structures that are usually the result of normal ECM remodeling observed in wild-type skin. Accordingly, Gray Level Co-occurrence Matrix analysis (GLCM) performed on SHG images of both 14-3-3ζ WT and KO mice 7 days post wound incision showed that collagen fibers at 14-3-3ζ KO wound margins have a significantly slower decay than 14-3-3ζ WT, suggesting that 14-3-3ζ KO wounds have a denser collagen matrix with a high level of crosslinking during wound healing compared to WT wounds. These data strongly suggest that collagen remodeling was impaired at 14-3-3ζ KO wound margins. Similarly, increased levels of two other ECM proteins, periostin and tenascin-C, were also observed in 14-3-3ζ KO skin compared to WT skin. All three proteins have established functions in tissue regeneration, including in the skin Interestingly, the levels of collagen and periostin were similar in unwounded 14-3-3ζ KO and WT skin, and tenascin-C was undetectable in unwounded skin of either genotype. Taken together, these results strongly suggest that 14-3-3ζ deficiency caused increased production and impaired remodeling of the extra-cellular matrix at wound margins.

Example 13—14-3-3ζ in Inflammatory Cells does not Influence Wound Healing

Inflammation has an important role in the wound healing process, for fighting infection and clearing tissue debris from the wound site. To ascertain whether the absence of 14-3-3ζ in the immune cell infiltrate of 14-3-3ζ KO mice plays a role in the accelerated healing observed in 14-3-3ζ KO wounds, we generated bone marrow chimeric mice by iso-grafting primary bone marrow cells into sub-lethally irradiated syngeneic mice as follows: 14-3-3ζ WT bone marrow cells into WT mice as an engraftment control, 14-3-3ζ KO bone marrow cells into WT mice and conversely 14-3-3ζ WT bone marrow cells into KO mice. After allowing 4 weeks for the engrafted bone marrow cells to reconstitute the immune system, we carried out incisional wounding on these mice and measured the widths of wounds harvested at day 5 post wounding. Wound healing in 14-3-3ζ KO mice engrafted with WT bone marrow was significantly accelerated when compared with that in 14-3-3ζ WT mice engrafted with KO bone marrow or 14-3-3ζ WT mice engrafted with WT bone marrow. Successful engraftment was verified at the end of the wound healing procedure, by flow cytometry and it was observed that 14-3-3ζ KO inflammatory cells are recruited to wounds at comparable rates to WT inflammatory cells. These data strongly suggest that the 14-3-3ζ deficiency within the immune system plays no role in the accelerated wound healing observed in 14-3-3ζ KO mice.

Example 14—14-3-3ζ-Deficient Dermal Fibroblasts Exhibit Impaired Matrix Remodeling Capabilities To determine why impaired collagen remodeling was observed during the healing of 14-3-3ζ KO wounds compared to WT, we used primary dermal fibroblasts derived from 14-3-3ζ KO mice and their WT littermates in an in vitro collagen remodeling assay. WT dermal fibroblasts embedded into a collagen matrix were able to rapidly remodel the collagen fibers, resulting in a significant reduction in matrix size within 5 days, whereas 14-3-3ζ KO dermal fibroblasts could not. 14-3-3ζ KO fibroblasts plated onto a collagen matrix exhibited more stress fibers than WT dermal fibroblasts reminiscent of 14-3-3ζ KO keratinocytes, but also exhibited larger focal adhesions that persist under conditions of serum starvation than those observed in WT dermal fibroblasts. However, total levels of paxillin were similar in dermal fibroblasts of both genotypes. Persistent focal adhesion dynamics in the absence of 14-3-3ζ were confirmed using live cell imaging of 14-3-3ζ KO and WT dermal fibroblasts expressing Paxillin labeled with enhanced green fluorescent protein (eGFP). Dynamic regulation of focal adhesions such that they are assembled and disassembled in a coordinated fashion is essential to fibroblast motility and their ECM remodeling. Accordingly, cell motility on a collagen coated surface as determined by the movement of cells into a scratch wound was significantly lower in 14-3-3ζ KO fibroblasts compared to WT fibroblasts. Consistent with these observations, dual live-cell imaging of GFP-labelled dermal fibroblasts with corresponding SHG imaging of 3D organotypic collagen matrices within which the cells had been embedded revealed that whereas WT cells exhibited an elongated, fibroblast-like morphology and actively interacted with the collagen matrix consistent with their good collagen remodeling capacity, 14-3-3ζ KO dermal fibroblasts exhibited a contracted morphology with blebbing and were relatively immotile consistent with their poor ECM remodeling capacity. Circularity analysis of cells within the 3D organotypic collagen matrices carried out to establish a quantitative basis for cell morphology (i.e. to quantify the extent to which 14-3-3ζ KO fibroblasts exhibited a more circular cross section, see Methods) revealed that 14-3-3ζ KO fibroblasts were approximately 40% less elongated that WT fibroblasts. 14-3-3ζ KO fibroblasts adopted a more elongated morphology similar.

These results demonstrate that 14-3-3ζ deficiency in dermal fibroblasts mediates persistent focal adhesion dynamics associated with a contracted morphology, reduced capacity to migrate on collagen and an impaired ability to remodel 3D collagen matrices.

Example 15—Inhibitors of 14-3-3 Activity Phenocopy 14-3-3ζ Deficiency

Figure 12:
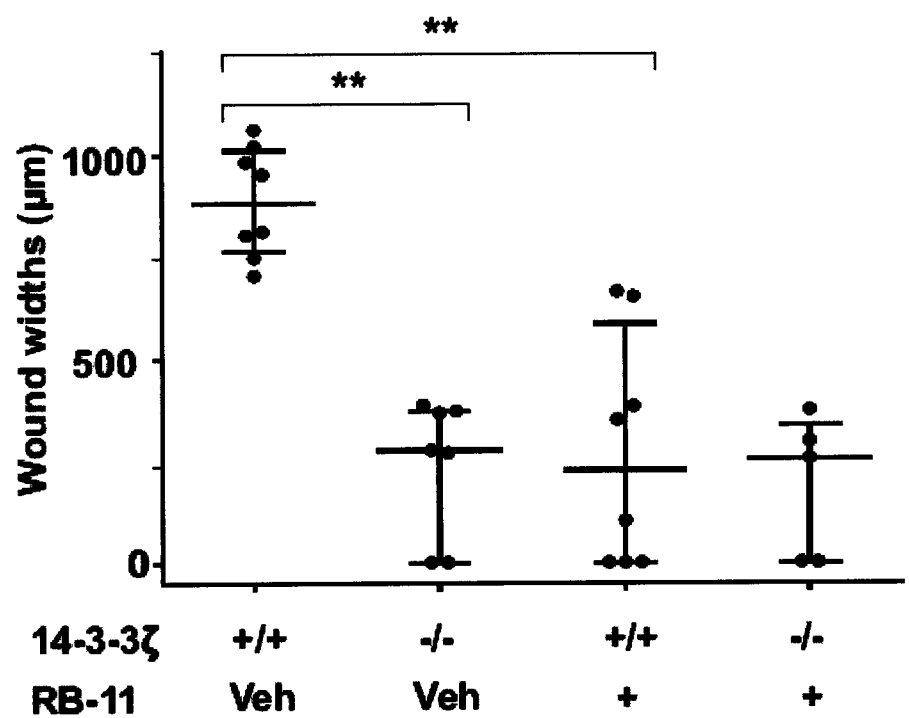
FIG. 12 shows box and whisker plots of wound width measurements in wild-type (+/+) and 14-3-3ζ-deficient (−/−) wounds, treated with vehicle or RB-11 (5× daily topical treatments of 11.5 µg) as indicated. P-values were derived from applying the Mann-Whitney test followed by the Dunnett's post hoc test. Data indicated that the application of RB-11 hastened wound healing to an extent comparable to that observed in 14-3-3ζ deficient wounds.

The data is shown in FIG. 12.

14-3-3ζ-deficient and wild-type mice were subjected to the incisional wounding protocol followed by treatment with vehicle or RB-11 (5× daily topical treatments of 11.5 μg). At day 5 following wounding, mice were humanely killed, the dorsal skin harvested, fixed for 16 hours in formalin, halved transversely and embedded in paraffin on the cut edge. Sections (4 μm) of paraffin embedded tissue were stained with haematoxylin and eosin, dehydrated and mounted in DPX. Slides were optically scanned using a Nanozoomer slide scanner (Hamamatsu, Japan) and the wound gap measured using Imagescope software (Leica Biosystems, Germany). Values were plotted on a box and whisker plot and statistical significant assessed using the Mann-Whitney test together with Dunnett's post hoc test. The data indicated that the application of RB-11 hastened wound healing to an extent comparable to that observed in 14-3-3ζ deficient wounds.

Figure 13A:
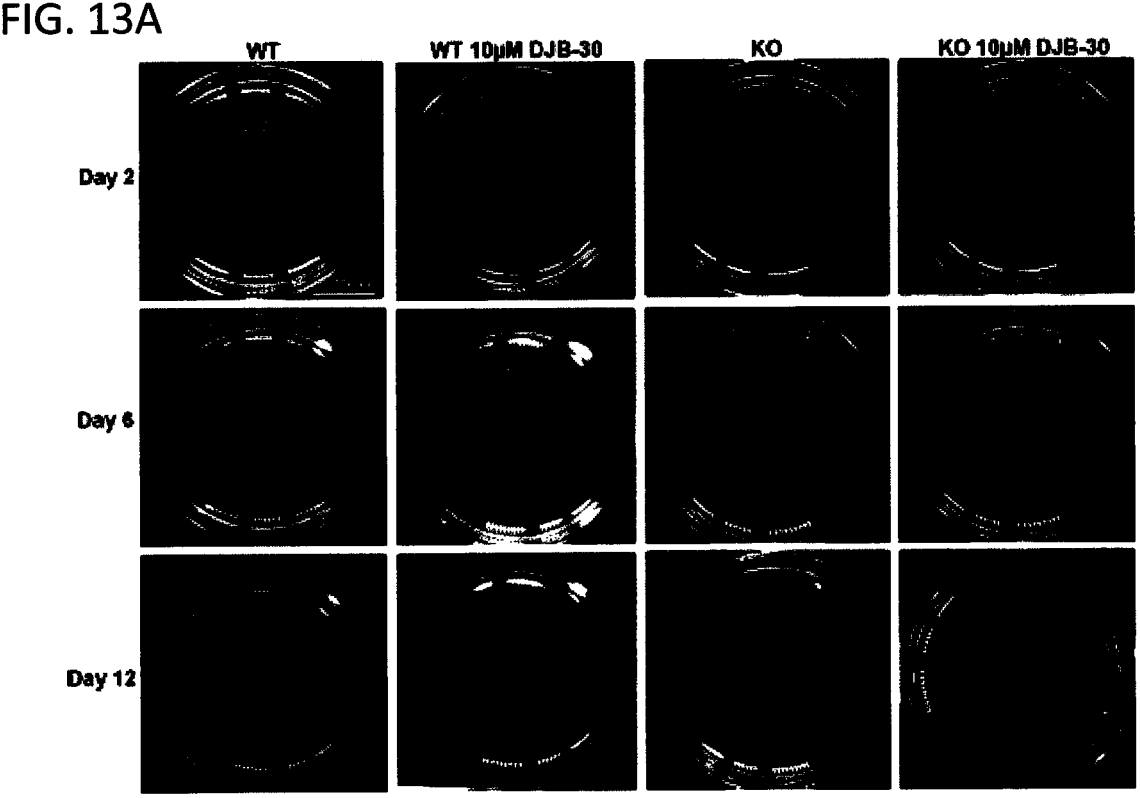
FIG. 13A shows collagen remodelling assay data, wherein dermal fibroblasts from wild-type and 14-3-3ζ-deficient mice were embedded in collagen gel plugs in the presence or absence of RB-11 (10 µM). The collagen remodelling ability of fibroblasts was assessed by their ability to contract the collagen plug. 14-3-3ζ-deficient fibroblasts or fibroblasts treated with RB-11 were unable to remodel the collagen plug, while collagen remodelling ability was unimpaired in wild-type fibroblasts in the absence of RB-11. These data are quantified in FIG. 13B.

Example 16—14-3-3ζ-Deficient Skin Fibroblasts Cells (KO) and Wild Type Fibroblast Cells Treated with a 14-3-3 Dimerization Inhibitor Show Reduced Ability to Remodel a Collagen Plug $10^6$ 14-3-3ζ-deficient or wild-type dermal fibroblasts were embedded in 2 mg/mL % rat tail collagen plugs made with or without 10 μM RB-11. The plugs were maintained in DMEM containing 10% foetal bovine serum in a humidified incubator at 37° C. Collagen plugs were photographed on days 2, 6 and 12 and the area of the image occupied by the collage plug measured. FIG. 13A shows that 14-3-3ζ deficient skin fibroblasts cells (KO) treated with a 14-3-3 dimerization inhibitor (RB-11/DJB-30; 10 μM) show a reduced ability to remodel a collagen plug as compared to wild type fibroblasts (WT).

Figure 13B:
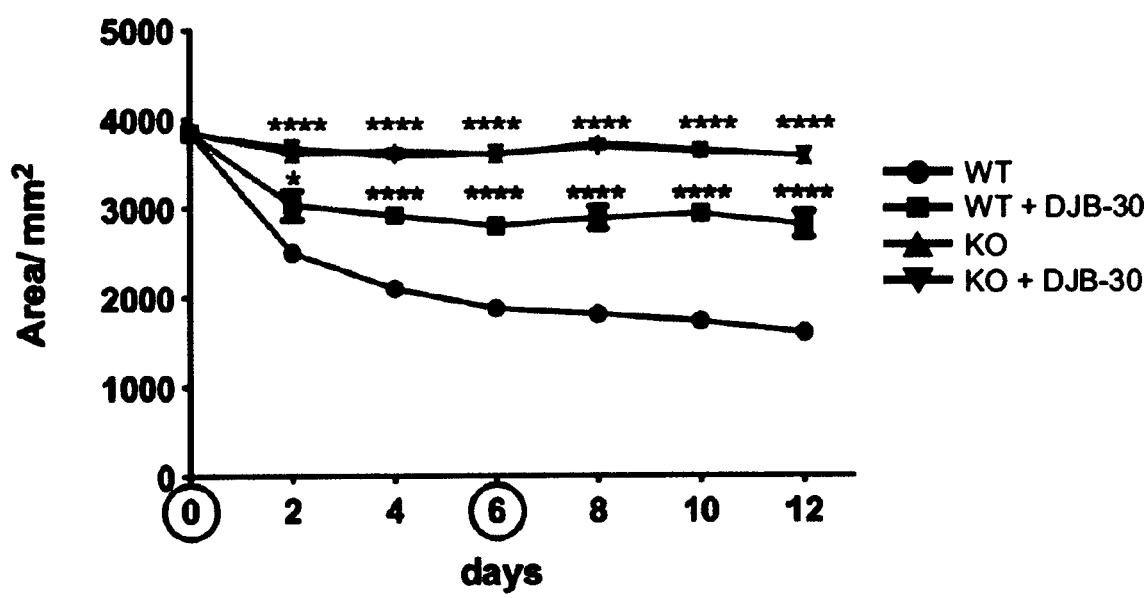

The data is quantified in FIG. 13B.

Example 17—Pharmacological Inhibition of 14-3-3 Function Accelerates Wound Healing and Phenocopies 14-3-3ζ Deficiency To determine whether pharmacological inhibition of 14-3-3 within the skin is able to phenocopy 14-3-3ζ deficiency and accelerate re-epithelialization during wound healing, we topically treated 14-3-3ζ WT and KO mice with RB-11 (10 μg [25 nmol] per application), once daily for 7 days following incisional wounding. Inhibition of 14-3-3 increased the rate of re-epithelialization (FIG. 12) and elevated collagen production in WT mice (FIG. 14A), in an identical manner to that observed in the corresponding wounds of 14-3-3ζ-deficient mice. Furthermore, WT dermal fibroblasts cultured in the presence of RB-11, exhibited significantly reduced collagen remodeling ability approaching that observed in 14-3-3ζ KO dermal fibroblasts (FIG. 14B). Live-cell images of GFP-labelled WT dermal fibroblasts within 3D collagen organotypic matrices treated with RB-11 exhibited a contracted morphology and interacted with the ECM and each other infrequently in a manner that was indistinguishable from 14-3-3ζ KO fibroblasts, whether treated with RB-11 or not. Accordingly circularity analysis revealed that WT dermal fibroblasts cultured in collagen 3D organotypic matrices containing RB-11 exhibited a rounded morphology similar to that observed in 14-3-3ζ KO dermal fibroblasts (FIG. 14C) and that treatment with RB-11 elicited no further change in the morphology of 14-3-3ζ KO dermal fibroblasts.

Taken together, these results demonstrate that pharmacological inhibition of 14-3-3 effectively phenocopies 14-3-3ζ deficiency, impairing the ability of dermal fibroblasts to remodel the ECM and accelerating wound healing.

Example 18—Expression of 14-3-3 in Diabetic Patients

Figures 15A, 15B:
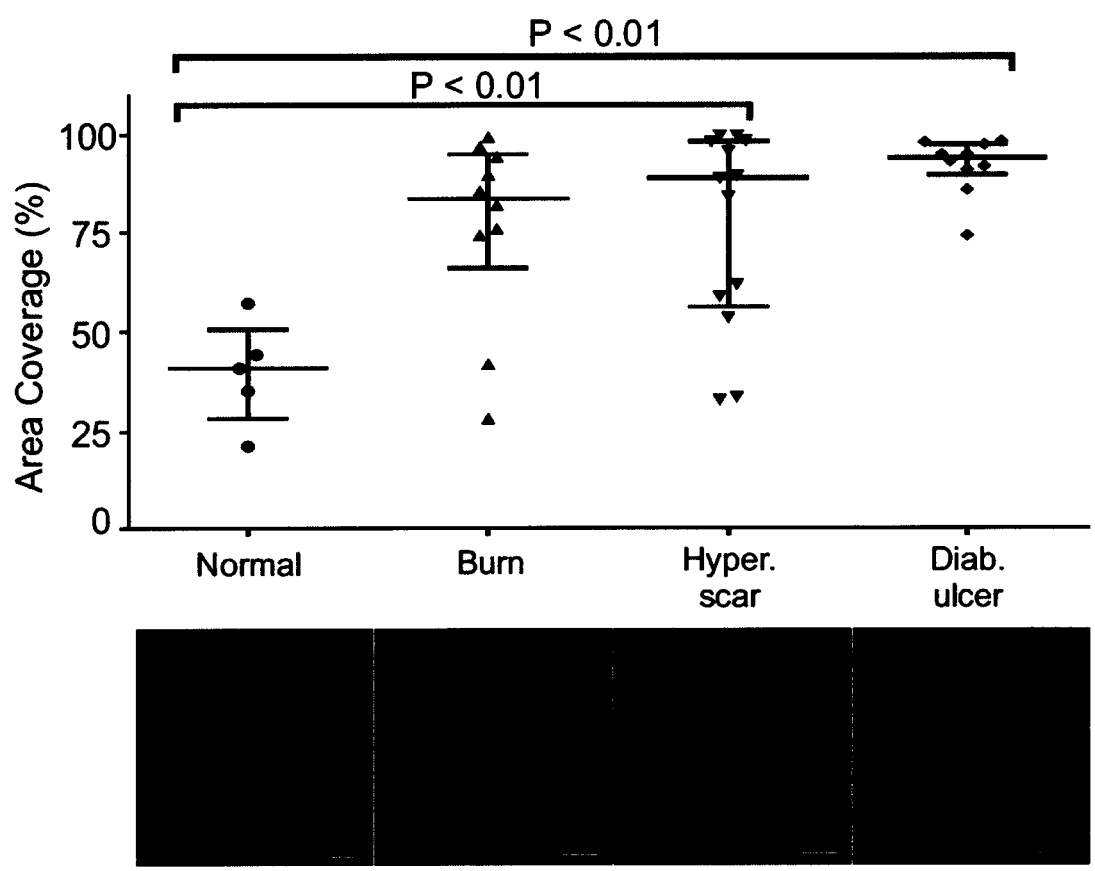
FIGS. 15A-15B show representative immunofluorescence analysis (FIG. 15B) showing 14-3-3ζ in normal human skin (N=5) and patient wound tissue together with area coverage analysis quantifying 14-3-3ζ expression in wound tissue compared to that in normal skin shown as medians and inter-quartile ranges (FIG. 15A). Burn: Burn wound (N=10); Hyper. scar: Hypertrophic scar (N=13); Diab. ulcer: Diabetic ulcer (N=10). Scale bar—100 µm.

Histological sections of wounds derived from diabetic and non-diabetic patients were subjected to immunofluorescence analysis using two 14-3-3ζ selective antibodies (Santa Cruz Biotechnology sc-1019; 1:100 and an in-house generated mouse monoclonal antibody; 1:100) following antigen retrieval for 15 minutes in a microwave pressure cooker in 10 mmol/L citrate buffer, pH 6.0. Representative images are shown in FIG. 15, indicating that 14-3-3ζ was unexpectedly upregulated in the wounds of diabetic patients, compared to those of unaffected individuals. These results, and the earlier results discussed herein, indicate that wounds in pre-diabetic or diabetic patients may be particularly suitable for treatment using agents that inhibit 14-3-3 functionality.

Example 19—14-3-3ζ is Upregulated in Chronic Wounds

Figure 16:
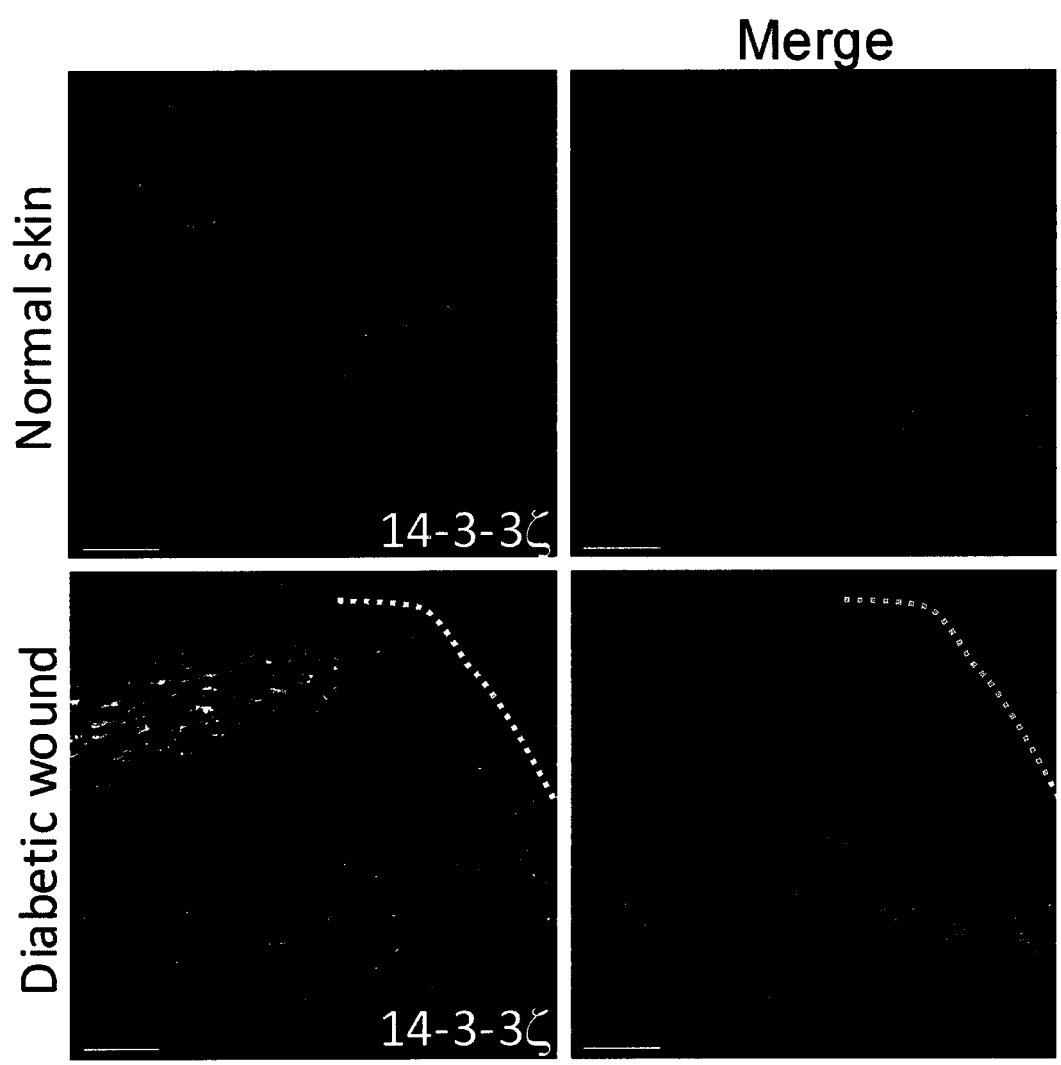
FIG. 16 shows representative images of histological sections of wounds derived from normal and diabetic patients subjected to immunofluorescence analysis using two 14-3-3ζ selective antibodies (Santa Cruz Biotechnology sc-1019 and an in-house generated mouse monoclonal antibody). The analysis revealed that the wounds of diabetic patients expressed elevated levels of 14-3-3ζ protein compared to those of non-diabetic subjects.

We used histological samples of three different categories of wounds with long healing times; burn, hypertrophic scar and diabetic ulcer, for confocal immunofluorescence analysis of 14-3-3ζ expression and compared these results to those from normal skin biopsies. Area coverage analysis of 14-3-3ζ immunofluorescence within the healing wound epidermis revealed that diabetic ulcers and hypertrophic scars exhibited a statistically significant >2-fold higher median expression of 14-3-3ζ compared to normal unwounded skin (FIG. 16A). Whereas the majority of burn biopsies expressed high levels of 14-3-3ζ compared to normal skin, the difference was not statistically significant as a proportion of burn samples analyzed exhibited levels of 14-3-3ζ that were comparable to those observed in normal unwounded skin (FIG. 16B). Chronic wounds usually exhibit long healing times and some may persist for several months or years. These data suggest that the long healing times usually exhibited by at least two types of chronic wounds, hypertrophic scar forming and diabetic ulcers, may arise from increased expression of 14-3-3ζ, and that patients with these wounds may therefore benefit from therapy to inhibit 14-3-3 activity to promote faster re-epithelialization.

Taken together with our observations on wound healing in 14-3-3ζ deficient mice and mice in which 14-3-3 has been pharmacologically inhibited, these observations strongly suggest that 14-3-3ζ-mediated moderation of mechano-reciprocity has an important function in maintaining epidermal homeostasis, by moderating the speed of wound healing.

Example 20—Topical Formulation and Use for Promoting Wound Healing

A topical cream formulation of RB-11 or RB-12 may be prepared by mixing aqueous hypoallergenic sorbolene cream (cetomacrogel cream without glycerol) with RB-11 and/or RB-12 at a concentration of 10-1000 µg/ml. The sorbolene cream is well absorbed into the skin, contains no active ingredients, and is suitable for preparation of a dermatological treatment.

The cream may be applied daily to an open wound and the treatment continued for 8-10 days until wound re-epithelialization is evident.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

Although the present disclosure has been described with reference to particular examples, it will be appreciated by those skilled in the art that the disclosure may be embodied in many other forms.

The invention claimed is:

1. A method of treating a disease, condition or state in a human subject associated with increased 14-3-3 protein functionality, wherein the disease, condition or state is a lung cancer, a leukemia or a wound, the method comprising administering to the human subject an effective amount of an agent which inhibits dimerization of the 14-3-3 protein, wherein the agent comprises a compound of the following formula:

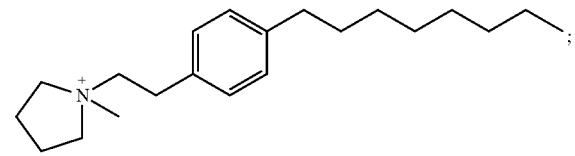

and/or

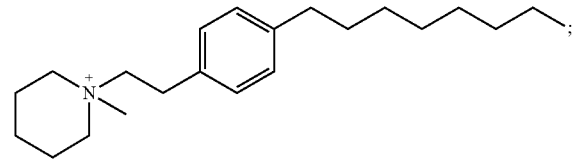

and/or a pharmaceutically acceptable salt or solvate thereof, thereby treating the disease, condition or state in the subject.

2. The method according to claim 1, wherein the agent is administered to the subject at a concentration of 0.5-50 mg/kg body weight.

3. The method according to claim 1, wherein the disease, condition or state is a lung cancer or a leukemia and the method further comprises administration of an anti-cancer agent.

4. The method according to claim 1, wherein the disease, condition or state comprises a wound and the administering of the agent comprises topical administration to the wound.

5. The method according to claim 4, wherein the subject is suffering from, or susceptible to, diabetes.

6. The method according to claim 1, wherein the lung cancer is non-small cell lung cancer.

7. The method according to claim 1, wherein the leukemia is T-cell leukemia.

* * * * *